US00RE34722E

United States Patent [19]

Uchida et al.

[11] E Patent Number: Re. 34,722

[45] Reissued Date of Patent: Sep. 6, 1994

[54] QUINOLINE AMINO ACID DERIVATIVES OF CARBOSTYRIL COMPOUNDS

[75] Inventors: Minoru Uchida, Komatsujima; Makoto Komastu; Kazuyuki Nakagawa, both of Tokushima, all of Japan

[73] Assignee: Otsuka Pharmaceutical Co., Ltd., Japan

[21] Appl. No.: 937,382

[22] Filed: Aug. 31, 1992

Related U.S. Patent Documents

Reissue of:

[64] Patent No.: 4,578,381
Issued: Mar. 25, 1986
Appl. No.: 510,241
Filed: Jul. 1, 1983

[30] Foreign Application Priority Data

Jul. 5, 1982 [JP] Japan ..... 57-117311
Jul. 5, 1982 [JP] Japan ..... 57-117312

[51] Int. Cl.[5] ..... A61K 31/47; C07D 215/22

[52] U.S. Cl. ..... 514/312; 546/157; 546/158; 514/228.8; 514/233.5; 514/253; 514/256; 544/99; 544/128; 544/238; 544/333; 544/405

[58] Field of Search ..... 514/312, 253, 233.5, 514/236.5; 546/157, 158; 544/238, 333, 405

[56] References Cited

U.S. PATENT DOCUMENTS

| | | | |
|---|---|---|---|
| 3,632,628 | 1/1972 | Suh | 546/158 |
| 4,065,572 | 12/1977 | Atkinson et al. | 548/486 |
| 4,070,470 | 1/1978 | Nakagawa et al. | 546/157 |
| 4,156,734 | 5/1979 | Stone . | |
| 4,216,220 | 8/1980 | Nakagawa et al. . | |
| 4,298,739 | 11/1981 | Nishi et al. | 546/158 |
| 4,313,947 | 2/1982 | Nakagawa et al. . | |
| 4,435,404 | 3/1984 | Nishi et al. | 546/158 |
| 4,460,593 | 7/1984 | Banno et al. | 546/157 |

(List continued on next page.)

FOREIGN PATENT DOCUMENTS

| | | | |
|---|---|---|---|
| 2927534 | 8/1981 | Fed. Rep. of Germany . | |
| 5297933 | 8/1977 | Japan . | |
| 0087368 | 8/1978 | Japan | 514/312 |

(List continued on next page.)

OTHER PUBLICATIONS

Uchida et al. Chem. Abstr. vol. 101 entry 54936g (1984).
Uchida et al., Chem. Abstr. vol. 105 entry 97287w (1985).

(List continued on next page.)

*Primary Examiner*—Donald G. Daus
*Attorney, Agent, or Firm*—Finnegan, Henderson, Farabow, Garrett & Dunner

[57] ABSTRACT

Disclosed are carbostyril derivatives and their salts of the formulas

The compounds have anti-peptic ulcer effects, and are useful as a treating agent for curing peptic ulcers in the digestive system, such as ulcers in the stomach and in the duodenum. The compounds particularly have prophylaxis and curing effects for treating chronic ulcers, for example experimental acetic acid-induced ulcers and cautery ulcers, with both low toxicity and few side-effects. Also disclosed are processes for preparing the compounds and for preparing pharmaceutical compositions containing them.

39 Claims, No Drawings

U.S. PATENT DOCUMENTS

| | | | |
|---|---|---|---|
| 4,468,402 | 8/1984 | Tominaga et al. | 514/253 |
| 4,619,932 | 10/1986 | Banno et al. | 514/253 |
| 5,225,402 | 6/1993 | Ogawa | 514/312 |

FOREIGN PATENT DOCUMENTS

| | | |
|---|---|---|
| 55-35018 | 3/1980 | Japan . |
| 55-83749 | 6/1980 | Japan . |
| 55-85520 | 6/1980 | Japan . |
| 56-12368 | 2/1981 | Japan . |
| 57-4974 | 1/1982 | Japan . |

OTHER PUBLICATIONS

Otsuka, Chem. Abstr. vol. 106 entry 50063a (1987).

Ye et al. Chem. Abstr. vol. 114 entry 121998n.

Shah et al., "Synthesis of β-(2-Hydroxy-4-Quinolyl-)-Alanine", Current Science (India), 1972, vol. 41, No. 24, p. 876.

Uchida et al., Chem. Phar. Bull. 33(9)3775-3786(1985) "Studies on 2(1H)-Quinolinone Derivatives as Gastric Antiulcer Active Agents. 2-(4-Chlorobenzoylamino)-3-[2(1H)-quinolinon-4-yl]propionic Acid and Related Compound".

Chemical Abstracts, vol. 78, No. 11, 72547s (1973).

QUINOLINE AMINO ACID DERIVATIVES OF CARBOSTYRIL COMPOUNDS

Matter enclosed in heavy brackets [ ] appears in the original patent but forms no part of this reissue specification; matter printed in italics indicates the additions made by reissue.

The present invention relates to a novel carbostyril derivative having anti-peptic ulcer action, processes for preparing the same and a pharmaceutical composition for treating peptic ulcers containing said carbostyril derivative as the active ingredient.

A novel carbostyril derivative and its salt of the present invention is represented by the general formula (1),

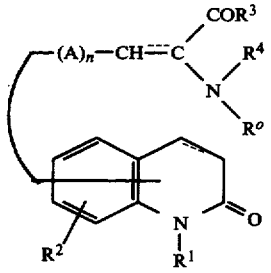

(1)

wherein, $R^1$ is a hydrogen atom, a lower alkyl group, a lower alkenyl group, a lower alkynyl group or a phenyl-lower alkyl group;

$R^2$ is a hydrogen atom, a halogen atom, a benzoloxy group (which may have halogen atoms as the substituents), a hydroxyl group, a lower alkyl group or a lower alkoxy group;

$R^3$ is a hydroxyl group, an amino group [which may have, as the substituent, a cycloalkyl-lower alkyl group (which may have, as the substituent, a carboxy group or a lower alkoxycarbonyl group on the cycloalkyl ring)], a lower alkoxy group, a lower alkoxycarbonyl-lower alkoxy group, a benzoyl-lower alkoxy group or a lower alkanoyloxy-lower alkoxy group;

$R^4$ is a hydrogen stom, a phenylsulfonyl group (which may have, as the substituents, lower alkyl groups or halogen atoms), a lower alkyl group, a phenyl-lower alkyl group (which may have, as the substituent, a halogen atom on the phenyl ring), or a group of the formula —$COR^5$ [wherein $R^5$ is a lower alkyl group (which may have, as the substituents, an amino group or a phenyl-lower alkoxycarbonylamino group), a cycloalkyl group (which may have, as the substituent, an amino-lower alkyl group or a phenyl-lower akloxycarbonylamino-lower alkyl group, on the cycloalkyl ring), a phenyl group (which may have 1 to 3 substituents selected from the group consisting of a halogen atom, a lower alkyl group a lower alkoxy group, a nitro group, an amino group and a hydroxyl group, on the phenyl ring), a phenyl-lower alkyl group (which may have, as the substituent, a halogen atom on the phenyl ring), or a 5- or 6-membered unsaturated heterocyclic ring having 1 to 2 hereto atoms selected from the group consisting of a nitrogen atom, an oxygen atom and a sulfur atom (said heterocyclic ring may have a lower alkyl group as the substituent)];

$R^o$ is a hydrogen atom or a phenylsulfonyl group (which may have, as the substituents, lower alkyl groups or halogen atoms);

A ia s lower alkylene group;

n is 0 or 1;

the carbon-carbon bond indicated as —C---C<, in the side-chain of the formula

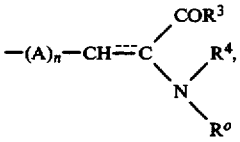

means a single or double carbon-carbon bond;

the carbon-carbon bond between 3- and 4-positions in the carbostyril skeleton is a single or double bond;

the substitution position of the side-chain of the formula

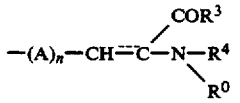

is any one of 3-, 4-, 5-, 6-, 7- or 8-position in the carbostyril skeleton.

A novel carbostyril derivative and its salt of the present invention represented by the general formula (1) has anti-peptic ulcer effects, and is useful as a treating agent for curing peptic ulcers in the digestive system, such as ulcers in the stomic and in the duodenum.

The carbostyril derivative of the present invention particularly has prophylaxis and curing effects for treating chronic ulcers for example, experimental acetic acid-induced ulcer and cautery ulcer, with both less toxicity and side-effects, thus the carbostyril derivative of the present invention is useful agent for curing chronic ulcers.

The carbostyril derivative of the present invention also has effects for increasing endogenic-prostaglandin $E_2$, and thus the derivative is useful as prophylaxis and curing agents for treating diseases by increasing endogenic-prostaglandin $E_2$. For example, the carbostyril derivative of the present invention is useful as prophylaxis and curing agent for treating peptic ulcers by increasing endogenic-prostaglandin $E_2$ in the gastromucosa.

An object of the present invention is to provide a novel carbostyril derivative and its salt represented by the general formula (1), having anti-peptic ulcer effects.

Another object of the present invention is to provide processes for preparing said carbostyril derivative and its salt represented by the general formula (1).

Further object of the present invention is to provide a pharmaceutical composition for treating peptic ulcers containing said carbostyril derivative or its salt as the active ingredient.

As to the lower alkyl group mentioned in the present specification, a straight- or branched-chain alkyl group having 1 to 6 carbon atoms, such as methyl, ethyl, propyl, isopropyl, butyl, isobutyl, pentyl or hexyl group can be exemplified.

As to the lower alkenyl group mentioned in the present specification, a straight- or branched-chain alkenyl group having 2 to 6 carbon atoms, such as vinyl, allyl, 2-butenyl, 3-butenyl, 1-methylallyl, 2-pentenyl or 2-hexenyl group can be exemplified.

As to the lower alkynyl group mentioned in the present specification, a straight- or branched-chain alkynyl group having 2 to 6 carbon atoms, such as ethynyl, 2-propynyl, 2-butynyl, 3-butynyl, 1-methyl-2-propynyl, 2-pentynyl or 2-hexynyl group can be exemplified.

As to the lower alkylene group mentioned in the present specification, a straight-chain alkylene group having 1 to 6 carbon atoms, such as methylene, ethylene, trimethylene, methyl-methylene, ethylmethylene, tetramethylene, pentamethylene or hexamethylene group can be exemplified.

As to the phenyl-lower alkyl group mentioned in the present specification, a phenyl-alkyl group in which the alkyl moiety is a straight- or branched-chain alkyl group having 1 to 6 carbon atoms, such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl or 2-methyl-3-phenylpropyl group can be exemplified.

As to the cycloalkyl group mentioned in the present specification, a cycloalkyl group having 3 to 8 carbon atoms, such as cyclopropyl, cyclobutyl, cyclopentyl, cyclohexyl, cycloheptyl or cyclooctyl group can be exemplified.

As to the lower alkoxy group mentioned in the present specification, a straight- or branched-chain alkoxy group having 1 to 6 carbon atoms, such as methoxy, ethoxy, propoxy, isopropoxy, butoxy, tertbutoxy, pentyloxy or hexyloxy group can be exemplified.

As to the halogen atom mentioned in the present specification, fluorine, chlorine, bromine or iodine atom can be exemplified.

As to the phenyl-lower alkoxycarbonylamino group mentioned in the present specification, a phenylalkoxycarbonylamino group in which the alkoxy moiety is a straight- or branched-chain alkoxy group having 1 to 6 carbon atoms, such as benzyloxycarbonylamino, 2-phenylethoxycarbonylamino, 1-phenylethoxycarbonylamino, 3-phenylpropoxycarbonylamino, 4-phenylbutoxycarbonylamino, 1,1-dimethyl-2-phenylethoxycarbonylamino, 5-phenylpentyloxycarbonylamino, 6-phenylhexyloxycarbonylamino or 2-methyl-3-phenylpropoxycarbonylamino group can be exemplified.

As to the lower alkyl group (which may have, as the substituents, an amino group or a phenyl-lower alkoxycarbonylamino group) mentioned in the present specification, in case that the alkyl group has no substituent, the above-mentioned lower alkyl group can be exemplified, while in case that the alkyl group has substituents, a straight- or branched-chain alkyl group having 1 to 6 carbon atoms (having a phenylakoxycarbonylamino group in which the amino group or alkoxy moiety having 1 to 6 carbon atoms), such as aminomethyl, 2-aminoethyl, 2- or 3-aminopropyl, 1-methyl-2-aminoethyl, 2-, 3- or 4-aminobutyl, 1,1-dimethyl-2-aminobutyl, 2- or 3-aminopentyl, 4-aminohexyl, benzyloxy carbonylaminomethyl, 2-benzyloxycarbonylaminoethyl, 2-benzyloxycarbonylaminopropyl, 3-benzyloxycarbonylaminopropyl, 4-benzyloxycarbonylaminobutyl, 3-benzyloxyaminocarbonylbutyl, 5-benzyloxycarbonylaminopentyl, 6-benzyloxycarbonylaminohexyl, 2-phenylethoxycarbonylaminomethyl, 1-phenylethoxycaronylaminomethyl, 2-(2-phenylethoxycarbonylamino)ethyl, 3-(1-phenylethoxycarbonylamino)-propyl, 2-(3-phenylpropoxycarbonylamino)ethyl, 4-(4-phenylbutoxycarbonylamino)butyl, 2-(5-phenylpentyloxycarbonylamino)ethyl, 2-(6-phenylhexyloxycarbonylamino)ethyl, 1,1-dimethyl-2-(benzyloxycarbonylamino)ethyl or (1,1-dimethyl-2-phenylethoxycarbonylamino)methyl group can be exemplified.

As to the phenyl group (which may have 1 to 3 substituents selected from the group consisting of a halogen atom, a lower alkyl group, a lower alkoxy group, a nitro group, an amino group and a hydroxyl group, on the phenyl ring), a phenyl group (which may have 1 to 3 substituents selected from the group consisting of a halogen atom, an alkyl group having 1 to 6 carbon atoms, an alkoxy group having 1 to 6 carbon atoms, a nitro group, an amino group and a hydroxyl group, on the phenyl ring), such as a phenyl, 2-, 3- or 4-chlorophenyl, 2-, 3- or 4-fluorophenyl, 2-, 3- or 4-bromophenyl, 2-, 3- or 4-iodophenyl, 3,5-dichlorophenyl, 2,6-dichlorophenyl, 3,4-dichlorophenyl, 3,4-difluorophenyl, 3,5-dibromophenyl, 2-, 3- or 4-methylphenyl, 2-, 3- or 4-ethylphenyl, 4-propylphenyl, 3-isopropylphenyl, 2-butylphenyl, 4-hexylphenyl, 3-pentylphenyl, 4-tert-butylphenyl, 3,4-dimethylphenyl, 2,5-dimethylphenyl, 2-, 3- or 4-methoxyphenyl, 2-, 3- or 4-ethoxyphenyl, 3-propoxyphenyl, 4-isopropoxyphenyl, 3-butoxyphenyl, 2-pentyoxyphenyl, 4-tert-butoxyphenyl, 4-hexyloxyphenyl, 3,4-dimethoxyphenyl, 3,4-diethoxyphenyl, 2,5-dimethoxyphenyl, 2-, 3- or 4-nitrophenyl, 2,4-dinitrophenyl, 2-, 3- or 4-aminophenyl, 2,4-diaminophenyl, 3-methyl-4-chlorophenyl, 2-chloro-6-methylphenyl, 2-methoxy-3-chlorophenyl, 3,4,5-trimethoxyphenyl, 3,4,5-trimethylphenyl, 3,4,5-trichlorophenyl, 2-, 3- or 4-hydroxyphenyl, 3,4-dihydroxyphenyl or 2,6-dihydroxyphenyl group can be exemplified.

As to the phenyl-lower alkyl group (which may have, as the substituents, halogen atoms on the phenyl ring) mentioned in the present specification, in case that no substituent on the phenyl ring, the above-mentioned phenyl-lower alkyl group can be exemplified, while in case that the phenyl ring has the substituents, a phenylalkyl group (having 1 to 3 halogen atoms are substituted on the phenyl ring, and the alkyl moiety having 1 to 6 carbon atoms), such as 2-, 3- or 4-chlorobenzyl, 2-, 3- or 4-fluorobenzyl, 2-, 3- or 4-bromobenzyl, 2-, 3- or 4-iodobenzyl, 3,5-dichlorobenzyl, 2,6-dichlorobenzyl, 3,4-dichlorobenzyl, 3,4-difluorobenzyl, 3,5-dibromobenzyl, 3,4,5-trichlorobenzyl, 2-(3-chlorophenyl)ethyl, 2-(3,4-dibromophenyl)ethyl, 2-(4-iodophenyl)ethyl, 1-(2-bromophenyl)ethyl, 1-(3,5-dichlorophenyl)ethyl, 1-(4-chlorophenyl)ethyl, 3-(2-fluorophenyl)propyl, 3-(3,4,5-trichlorophenyl)propyl, 4-(4-chlorophenyl)butyl, 1,1-dimethyl-2-(3-bromophenyl)ethyl, 5-(2,4-dichlorophenyl)benzyl, 5-(2-iodophenyl)pentyl, 6-(4-fluorophenyl)hexyl, 6-(2,6-dichlorophenyl)hexyl or 2-methyl-3-(4-chlorophenyl)propyl group can be exemplified.

As to the cycloalkyl group (which may have, as the substituents, an amino-lower alkyl group or a phenyl-lower alkoxy-carbonylamino-lower alkyl group, on the cycloalkyl ring) mentioned in the present specification, in case that the cycloalkyl group has no substituent, the above-mentioned cycloalkyl group can be exemplified, while in case that the cycloalkyl group has substituents, a substituted-cycloalkyl group having 3 to 8 carbon atoms in the cycloalkyl moiety, (having an aminoalkyl group having 1 to 6 carbon atoms in the alkyl moiety, or a phenyl-lower alkoxy-carbonylamino-lower alkyl group having 1 to 6 carbon atoms in the alkoxy moiety and 1 to 6 carbon atoms in the alkyl moiety, on the cycloalkyl ring), such as 3-aminoaminocyclopropyl, 3-(2-aminoethyl)cyclobutyl, 4-(1-aminoethyl)cyclopentyl, 2-(3-aminopropyl)cyclohexyl, 3-(4-aminobutyl)cyclohexyl, 4-aminomethylcyclohexyl, 3-(5-aminopentyl)-cycloheptyl, 2-benzyloxycabonylaminomethycylopropyl, 3-(2-benzyloxycarbonylaminoethyl)cyclobutyl, 3-(2-benzyloxycarbonylaminopropyl)cyclopentyl, 2-(3-benzyloxycarbonylaminopropyl)cyclopentyl, 3-(4-benzyloxycarbonylaminobutyl)cyclohexyl, 4-(3-benzyloxycarbonylaminobuty)cyclohexyl, 2-(5-benzyloxycarbonylaminopentyl)cyclohexyl, 3-(6-benzyloxycarbonylaminohexyl)cycloheptyl, 4-(6-benzyloxycarbonylaminohexyl)cycloheptyl, 5-(2-phenylethoxycarbonylaminomethyl)cycloheptyl, 4-(1-phenylethoxycarbonylaminomethyl)cyclooctyl, 2-[2-(2-phenylethoxycarbonylamino)ethyl]cyclooctyl, 2-[3-(1-phenylethoxycarbonylamino)propyl]cyclopropyl, 3-[2-(3-phenylpropoxycarbonylamino)ethyl]cyclobutyl, 3-[4-(4-phenylbutoxycarbonylamino)butyl]cyclopentyl, 4-[2-(5-phenylpentyloxycarbonylamino)ethyl]hexyl, 2-[2-(6-phenylhexyloxycarbonylamino)ethyl]cyclohexyl, 3-[1,1-dimethyl-2-(benzyloxycarbonylamino)ethyl]cyclohexyl, 4-[1,1-dimethyl-2-phenylethoxycarbonyl]cyclohexyl, 2-benzyloxycarbonylmethycyclooctyl, 4-benzyloxycarbonylmethylcyclohexyl or 3-(6-aminohexy)-cyclooctyl group can be exemplified.

As to the lower alkoxycarbonyl group mentioned in the present specification, a straight- or branched-chain alkoxycarbonyl group having 1 to 6 carbon atoms in the alkoxy moiety, such as methoxycarbonyl, ethoxycarbonyl, propoxycarbonyl, isopropoxycarbonyl, butoxycarbonyl, tert-butoxycarbonyl, pentyloxycarbonyl or hexyloxycarbonyl group can be exemplified.

As to the amino-lower alkyl group mentioned in the present specification, a straight- or branched-chain alkylamino group having 1 to 6 carbon atoms in the alkyl moiety, such as aminomethyl, 2-aminoethyl, 1-aminoethyl, 3-aminopropyl, 4-aminobutyl, 1,1-dimethyl-2-aminoethyl, 5-aminopentyl, 6-aminohexyl or 2-methyl-3-aminopropyl group can be exemplified.

As to the amino group [which may have, as the substituents, a cycloalkyl-lower alkyl group (which may have, as the substituents, a carboxy group or a lower alkoxycarbonyl group on the cycloalkyl ring)] mentioned in the present specification, a substituted-amino group [having a cycloalkyl-lower alkyl group, in which the alkyl moiety is a straight- or branched-chain alkylene group having 1 to 6 carbon atoms, and the cycloalkyl moiety is a cycloalkyl group having 3 to 8 carbon atoms (on said cycloalkyl ring, carboxy group or an alkoxy-carbonyl group having 1 to 6 carbon atoms in the alkoxy moiety may be substitued thereon)], such as amino, cyclopropylmethyl amino, 2-cyclobutylethylamino, 1-cyclopentylethylamino, 3-cyclohexylpropylamino, 4-cycloheptylbutylamino, 5-cyclooctylpentylamino, 6-cyclohexylhexylamino, cyclohexylmethylamino, 2-methyl-3-cyclohexylpropylamino, (2-carboxycyclopropyl)methylamino, 2-(3-carboxycyclobutyl)ethylamino, 1-(3-carboxycyclopentyl)ethylamino, 3-(2-carboxycyclopentyl)propylamino, 4-(3-carboxycyclohexyl)butylamino, 5-(4-carboxycyclohexyl)penthylamino, 6-(2-carboxycyclohexyl)hexylamino, (3-carboxycycloheptyl)methylamino, 2-(4-carboxycycloheptyl)ethylamino, 1-(5-carboxycyclohepty)ethylamino, 3-(4-carboxycyclooctyl)propylamino, 4-(2-carboxycyclooctyl)butylamino, (4-carboxycyclohexyl)-methylamino, 6-(2-methoxycarbonylcyclopropyl)hexylamino, 5-(3-ethoxycarbonylcyclobutyl)pentylamino, 4-(3-propoxycarbonylcyclopentyl)butylamino, 3-(4-methoxycarbonylcyclohexyl)propylamino, 2-(2-n-butoxycarbonylcyclohexyl)ethylamino, 1-(3-hexyloxycarbonylcyclohexyl)ehtylamino, (3-ethoxycarbonylcyclohexyl)methylamino, 2-methyl-3-(2-propoxycarbonylcyclohepty)propylamino, (5-methoxycarbonylcyclooctyl)methylamino or (4-methoxycarbonylcyclohexyl)methylamino group can be exemplified.

As to the lower alkoxycarbonyl-lower alkoxy group mentioned in the present specification, an alkoxycarbonylalkoxy group in which the alkoxy moieties are straight- or branched-chains having 1 to 6 carbon atoms, such as methoxycarbonylmethoxy, 2-methoxycarbonylethoxy, 1-methoxycarbonylethoxy, 3-methoxycarbonylpropoxy, 4-methoxycarbonylbutoxy, 1,1-dimenthyl-2-methoxycarbonylethoxy, 5-methoxycarbonylpentyloxy, 6-methoxycarbonylhexyloxy, 2-methyl-3-methoxycarbonylpropoxy, ethoxycarbonylmethoxy, 3-ethoxycarbonylpropoxy, 6-ethoxycarbonylhexyloxy, 2-propoxycarbonylethoxy, 4-propoxycarbonylbutoxy, 5-butoxycarbonylpentyloxy, pentyloxycarbonylmethoxy, 1-pentyloxycarbonylethoxy, 1,1-dimethyl-2-hexyloxycarbonylethoxy or 3-hexyloxycarbonylpropoxy group can be exemplified.

As to the benzoyl-lower alkoxy group mentioned in the present specification, a benzoylalkoxy group in which the alkoxy moiety is a straight- or branched-chain alkoxy group having 1 to 6 carbon atoms, such as benzoylmethoxy, 2-benzoylethoxy, 1-benzoylethoxy, 3-benzoylpropoxy, 4-benzoylbutoxy, 1,1-dimenthyl-2-benzoylethoxy, 5-benzoylpentyloxy, 6-benzoylhexyoxy or 2-methyl-3-benzoylpropoxy group can be exemplified.

As to the lower alkanoyloxy-lower alkoxy group mentioned in the present specification, an alkanoyloxyalkoxy group in which the alkoxy moiety is a straight- or branched-chain alkoxy group having 1 to 6 carbon atoms, and the alkanoyloxy moiety is a straight- or branched-chain alkanoyloxy group having 1 to 6 carbon atoms, such as acetyloxymethoxy, 2-acetyloxyethoxy, 1-acetyloxyethoxy, 3-acetyloxypropoxy, 4-acetyloxybutoxy, 1,1-dimethyl-2-acetyloxyethoxy, 5-acetyloxypentyloxy, 6-acyteyloxyhexyloxy, 2-methyl-3-acetyloxypropoxy, propinoyloxymethoxy, 3-propionyloxypropoxy, 6-propionyloxyhexyloxy, 2-butyryloxyethoxy, 4-butyryloxybutoxy, 5-pentanoyloxypentyloxy, pentanoyloxymethoxy, tert-butylcarbonyloxymethoxy, 2-(tert-butylcarbonyloxy)ethoxy, 1-(tert-butylcarbonyloxy)ethoxy, 3-(tert-butylcarbonyloxy)propoxy, 4-(tert-butylcarbonyloxy)butoxy, 1,1-dimethyl-2-(tert-butylcarbonyloxy)ethoxy, hexanoyloxymethoxy, 3-hexanoyloxypropoxy or 6-(tert-butylcarbonyloxy)hexyloxy group can be exemplified.

As to the lower alkanoyl group mentioned in the present specification, a straight- or branched-chain alkanoyl group having 1 to 6 carbon atoms, such as formyl, acetyl, propionyl, butyryl, isobutyryl, pentanoyl, tert-butylcarbonyl or hexanoyl group can be exemplified.

As to the phenylsulfonyl group (which may have, as the substituents, lower alkyl groups or halogen atoms) mentioned in the present specification, a phenylsulfonyl group (which may have, as the substituents, alkyl groups having 1 to 6 carbon atoms or halogen atoms), such as a phenylsulfonyl, 4-methylphenylsulfonyl, 3-methylphenylsulfonyl, 2-methylphenylsulfonyl, 2l -ethylphenylsulfonyl, 3-ethylphenylsulfonyl, 4-ethylphenylsulfonyl, 3-isopropylphenylsulfonyl, 4-hexyl-phenylsulfonyl, 2-n-butylphenylsulfonyl, 4-pentylphenylsulfonyl, 2-, 3- or 4-chlorophenylsulfonyl, 2-, 3- or 4-bromophenylsulfonyl, 2-, 3- or 4-iodophenylsulfonyl group or 2-, 3- or 4-fluorophenylsulfonyl group can be exemplified.

As to the benzoyloxy group (which may have halogen atoms as the substituents) mentioned in the present specification, 2-, 3- or 4-chlorobenzoyloxy, 2-, 3- or 4-fluorobenzoloxy, 2-, 3- or 4-bromobenzoyloxy, or 2-, 3- or 4-iodobenzoyloxy group can be exemplified.

As to the halogen atom mentioned in the present specification, a fluorine atom, a chlorine atom, a bromine atom or a iodine atom can be exemplified.

As to the 5- or 6-membered unsaturated heterocyclic ring having 1 to 2 hetero atoms selected from the group consisting of a nitrogen atom, an oxygen atom and a sulfur atom (said heterocyclic ring may have a lower alkyl group having 1 to 6 carbon atoms as the substituent) mentioned in the present specification, example include pyridyl, 2-methylpyridyl, 3-ethylpyridyl, 4-butylpyridyl, thienyl, 2-methylthienyl, 3-propylthienyl, pyrimidyl, 2-pentylpyrimidinyl, pyrrolyl, 3-methylpyrrolyl, 1-pyrazinyl, 4-pentyl-1-pyrazinyl, pyrazoylyl, 3-methylpyrazolyl, 4-ethylpyrazolyl, imidazolyl, 2-propylimidazolyl, 4-pentylimidazolyl, pyridazinyl, 4-methylpyridazinyl, pyrazinyl, 2-ehtylpyrazinyl, oxazolyl, 4-butyloxazolyl, isoxazolyl, 4H-1,4-oxazinyl, thiazolyl, 4-methylthiazolyl, 2-ethylthiazolyl, 5-propylthiazolyl, isothiazolyl, 3-methylisothiazolyl, furyl, 3-methylfuryl, 2-ethylfuryl, 2-methylthianyl, 4-methylthianyl and 4-methylthianyl groups.

The substitution position of the side-chain of the formula

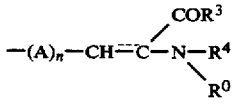

is any one of 3-, 4-, 5-, 6-, 7- or 8-position in the carbostyril skeleton.

Novel carbostyril derivatives of the present invention also including their optical isomers.

Novel carbostyril derivatives of the present invention can be prepared by various methods, for example, by reaction process formula-I as shown in the following reaction scheme.

[Reaction process formula-I]

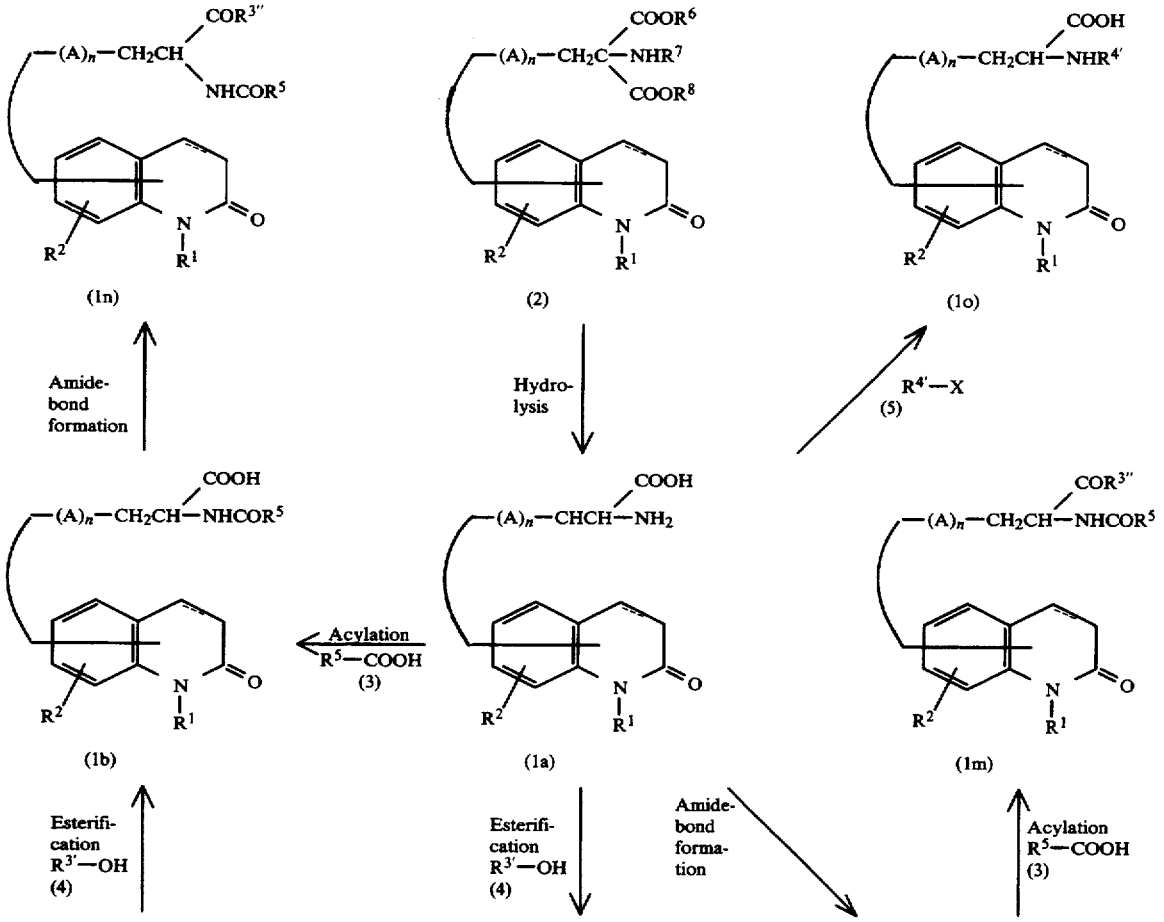

-continued

[Reaction process formula-I]

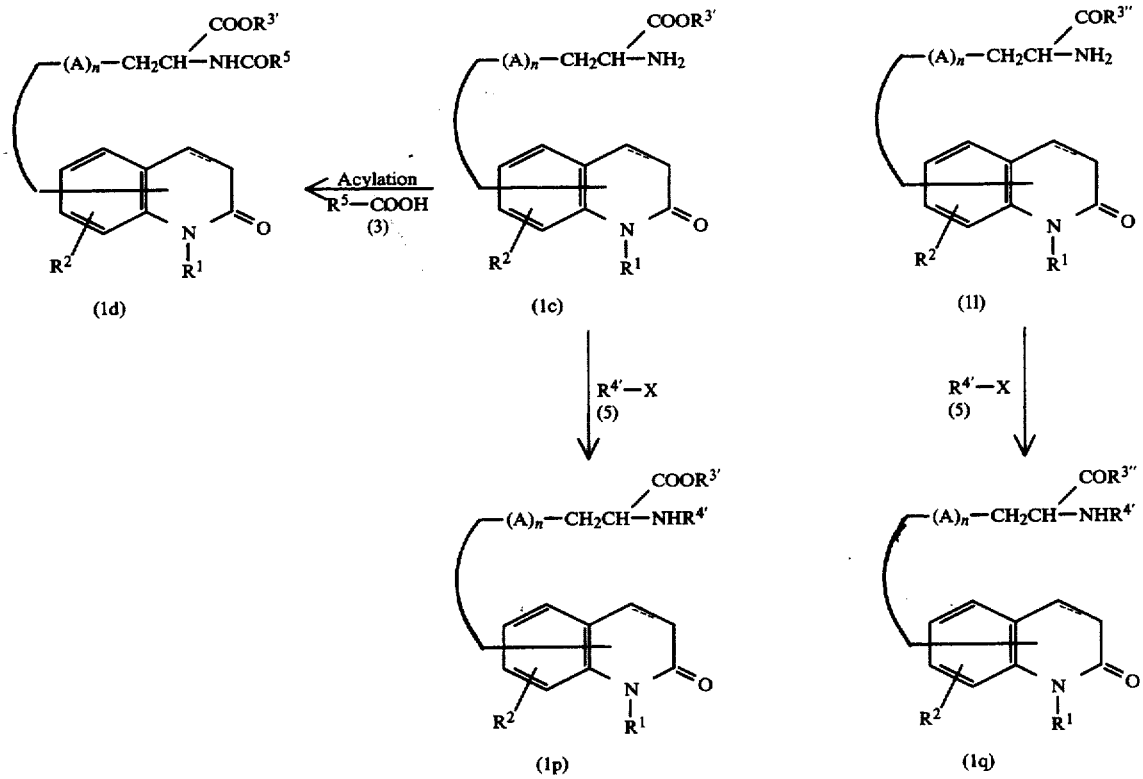

wherein $R^1$, $R^2$, $R^5$, A, n and the carbon-carbon bond between 3- and 4-positions in the carbostyril skeleton are the same as defined above; $R^{3'}$ is a lower alkyl group, a lower alkoxycarbonyl-lower alkyl group, a benzoyl-lower alkyl group or a lower alkanoyloxy-lower alkyl group; $R^{4'}$ is a phenylsulfonyl group (which may have, as the substituents, lower alkyl groups or halogen atoms), a lower alkyl group or a phenyl-lower alkyl group (which may have halogen atoms as the substituents on the phenyl ring); $R^6$ and $R^8$ are each a lower alkyl group respectively; $R^7$ is a lower alkanoyl group; $R^{3''}$ is an amino group [which may have, as the substituent, a cycloalkyl-lower alkyl group (which may have, as the substituent, a carboxy group or a lower alkoxycarbonyl group on the cycloalkyl ring)]; and X is a halogen atom.

Thus, the desired carbostyril derivative can be prepared by hydrolyzing a compound of the formula (2), and if desired the obtained product may be acylated, alkylated, amidated, esterified or treated by combination of these processes.

The reaction for preparing compound of the formula (1a) which is one of the desired compounds of the present invention by hydrolyzing a compound of the formula (2) can be carried out in the presence of a suitable hydrolyzing catalyst, for example a hydrohalogenic acid such as hydrochloric acid or hydrobromic acid; a mineral acid such as sulfuric acid or phosphoric acid; an inorganic alkaline compound for example, an alkaline metal hydroxide such as sodium hydroxide or potassium hydroxide; an alkaline metal carbonate or hydrogencarbonate, such as sodium carbonate, potassium carbonate or sodium hydrogencarbonate, in the absence or presence of a suitable solvent (for example, water or a mixed solvent of water with a lower alcohol such as methanol or ethanol), at 50°-150° C., preferably at 70°-100° C., for 3-24 hours.

Compound of the formula (1a), (1c) or (1l) can be acylated by using a carboxylic acid of the formula (3) to obtain the corresponding desired compound of the formula (1b), (1d), or (1m), said acylation can be achieved by carrying out a common amide-bond formation reaction. In this instance, said carboxylic acid of the formula (3) may be of an activated carboxylic acid.

The amide-bond formation reaction can be carried out by applying reaction conditions for a common amide-bond formation reaction. For example (a) a mixed acid anhydride method, that is a method by reacting a carboxylic acid (3) with an alkylhalocarboxylic acid to obtain a mixed acid anhydride, then reacting said mixed acid anhydride with a compound (1a), (1c), or (1l); (b) an activated ester method or activated amide method, that is a method by converting a carboxylic acid (3) into an activated ester for example p-nitrophenyl ester, N-hydroxysuccinimide ester or 1-hydroxybenzotriazole ester; or into an activated amide for example benzoxazolin-2-thione, then reacting said activated ester or activated amide with a compound of the formula (1a), (1c) or (1l); (c) a carbodiimide method, that is a method by dehydrocondensing a carboxylic acid (3) with a compound of the general formula (1a), (1c) or (1l) in the presence of a dehydrating agent such as dicyclohexylcarbodiimide or carbonyldiimidazole; (d) a carboxylic acid halide method, that is a method by converting a carboxylic acid (3) into a carboxylic acid halide, then reacting said halide with a compound of the general formula (1a), (1c) or (1l); (e) as to other methods, for example, a method by converting a carboxylic acid (3) into a carboxylic acid anhydride by using for example acetic anhydride as a dehydrating agent, then reacting said carboxylic acid anhydride with a compound of the general formula (1a), (1c) or (1l); or a method by reacting an ester of a carboxylic acid (3) and a lower alcohol with a compound of the general formula (1a), (1c), or (1l) under a high pressure and at an elevated temperature. Further, a method in which a carboxylic acid is activated with a phosphorus compound such as triphenylphosphine or diethyl chlorophosphate, then reacting said activated carboxylic acid (3) with a compound of the general formula (1a), (1c) or (1l) can be applied.

As to the alkylhalocarboxylic acid used in the mixed acid anhydride method, there can be exemplified methyl chloroformate, methyl bromoformate, ethyl chloroformate, ethyl bromoformate or isobutyl chloroformate. The mixed acid anhydride is prepared by a conventional Schotten-Baumann reaction, said mixed acid anhydride is reacted, without separated from the reaction system, with a compound of the general formula (1a), (1c), or (1l) to obtain a compound of the general formula (1b), (1d) or (1m) of the present invention. The Schotten-Baumann reaction is generally carried out in the presence of a basic compound. As to the basic compound to be used any compound usually used in Schotten-Baumann reaction can be also used, for example an organic base such as triethylamine, trimethylamine, pyridine, dimethylaniline, N-methylmorpholine, 4-dimethylaminopyridine, 1,5-diazabicyclo[4,3,0-]nonene-5 (DBN), 1,5-diazabicyclo[5,4,0]undecene-5 (DBU or 1,4-diazabicycle[2,2,2]octane (DABCO); an inorganic basic compound such as potassium carbonate, sodium carbonate, potassium hydrogencarbonate or sodium hydrogencarbonate. Said reaction is carried out at a temperature of −20° to 100° C., preferably at 0° to 50° C., and the reaction time is about 5 minutes to 10 hours, preferably 5 minutes to 2 hours. A reaction of a mixed acid anhydride thus obtained with a compound of the general formula (1a), (1c) or (1l) is carried out at about −20° to 150° C., preferably at 10° to 50° C. for about 5 minutes to 10 hours, preferably about 5 minutes to 5 hours. The mixed acid anhydride method can be carried out without a solvent, but is generally carried out in a solvent. As to the solvent used in the reaction, any solvent conventionally used in a mixed acid anhydride method can also be used, specifically, a halogenated hydrocarbon such as methylene chloride, chloroform, dichloroethane; an aromtic hydrocarbon such as benzene, toluene or xylene; an ether such as diethyl ether, tetrahydrofuran or dimethoxyethane; an ester such as methyl acetate or ethyl acetate; an aprotic polar solvent such as dimethylformamide, dimethyl sulfoxide or hexamethylphosphoryl triamide, are exemplified.

In carrying out the reaction the ratio of the amount of a carboxylic acid (3), to the amount of an alkylhalocarboxylic acid and to the amount of a compound of the general formula (1a), (1c) or (1l) is not specifically restricted, and generally at least an equimolar amount each of these reactants are used, preferably 1 to 2 times the molar quantity of the alkylhalocarboxylic acid and of a compound of the general formula (1a), (1c), or (1l) may be used to the carboxylic acid (3).

In carrying out the above-mentioned method of (b) an activated ester method or an activated amide method, for example in using benzoxazolin-2-thionamide, the reaction can be carried out in a suitable inert solvent which does not give any adverse effect to the reaction, such as a solvent similar to that may be used in the above-mentioned mixed acid anhydride method or other solvent such as 1-methyl-2-pyrrolidone, at a temperature of 0° to 150° C., preferably at a temperature of 10° to 100° l C., for 0.5 to 75 hours. As to a ratio of the amount of a compound of general formula (1a), (1c) or (1l) to the amount of benzoxazolin-2-thionamide is generally at least an equimolar amount, preferably an equimolar to 2 times the molar quantity of the latter is used to the former. In using N-hydroxysuccinimide ester, a suitable basic compound for example a basic compound which can be used in the above-mentioned (d) carboxylic acid halide method can also be used to proceed the reaction advantageously.

In carrying out the above-mentioned method of (d) a carboxylic acid halide method, a carboxylic acid (3) is reacted with a halogenating agent to prepare a carboxylic acid halide, then said carboxylic acid halide is reacted with a compound of the general formula (1a), (1c) or (1l), said carboxylic acid halide may be used with or without separated from the reaction system. The reaction of said carboxylic acid halide with a compound of the general formula (1a), (1c), or (1l) can be carried out in the presence of a dehydrohalogenating agent in a solvent. As to the dehydrohalogenating agent, a common basic compound may be used, thus other than a basic compound used in Schotten-Baumann reaction, sodium hydroxide, potassium hydroxide, sodium hydride, potassium hydride, silver carbonate, an alkali metal alkolate such as sodium methylate or sodium ethylate, can be exemplified. An excess amount of compound of the formula (1a), (1c) or (1l) can also be used as the dehydrohalogenating agent. As to the solvent, other than the solvent used in the above-mentioned Schotten-Baumann reaction, water; an alcohol such as methanol, ethanol, propanol, butanol, 3-methoxy-1-butanol, ethyl cellosolve or methyl cellosolve; pyridine; acetone; or acetonitrile; or a mixed solvent consisting of two or more of the above-mentioned solvents can be exemplified. The ratio of the amount of compound of the formula (1a), (1c) or (1l) to the amount of the carboxylic acid halide is not specifically restricted, and can be selected from a wide range, and generally, at least an equimolar quantity, preferably, an equimolar to 2 times the molar quantity of the latter can be used to the former. The reaction temperature is generally at −30° to 180° C., preferably, about 0° to 150° C., and generally, the reaction is completed for about 5 minutes to 30 hours.

The carboxylic acid halide is prepared by reacting a carboxylic acid (3) with a halogenating agent in the presence or absence of a solvent. As to the solvent, any solvent which does not give any adverse effect to the reaction can be used, for example, an aromatic hydrocarbon such as benzene, toluene or xylene; a halogenated hydrocarbon such as chloroform, methylene chloride or carbon tetrachloride; an ether such as dioxane, tetrahydrofuran or diethyl ether; or an aprotic polar solvent such as dimethylformamide or dimethyl sulfoxide, can be exemplified. As to the halogenating agent, a common halogenating agent which can be able to convert the hydroxyl group of the carboxylic acid can be used, for example thionyl chloride, phosphorus oxychloride, phosphorus oxybromide, phosphorus pentachloride or phosphorus pentabromide, can be exemplified. The ratio of the amount of the carboxylic acid (3) to the amount of the halogenating agent is not specifically restricted and can be selected from a wide range, in case that the reaction is carried out in the absence of a solvent, the latter is used in a large excess amount to the former, while in the presence of a solvent, the latter is used in at least about an equimolar, preferably 2 to 4 times the molar quantity to the former. The reaction temperature and the reaction time are not specifically restricted, and generally, the reaction is carried out at about a room temperature to 100° C., preferably 50° to 80° C., for 30 minutes to 6 hours.

Above-mentioned method in which a carboxylic acid (3) is activated with a phosphorus compound such as triphenylphosphine or diethyl chlorophosphate, then reacting said activated carboxylic acid (3) with a compound of the formula (1a), (1c) or (1l), the reaction is carried out in a suitable solvent. As to the solvent, any solvent which does not give any adverse effect to the reaction can be used, and specifically, a halogenated hydrocarbon such as methylene chloride, chloroform or dichloroethane; an aromatic hydrocarbon such as benzene, toluene or xylene; an ether such as diethyl ether, tetrahydrofuran or dimethoxyethane; an ester such as methyl acetate or ethyl acetate; an aprotic polar solvent such as dimethylformamide, dimethyl sulfoxide or hexamethylphosphoryl triamide; can be exemplified. In this reaction, compound of the formula (1a), (1c) or (1l) per se can be act as the basic compound, the reaction can be carried out preferably when the compound of the formula (1a), (1c), or (1l) used in an excess amount. If necessary, other basic compound, for example an organic basic compound such as triethylamine, trimethylamine, pyridine, dimethylaniline, N-methylmorpholine, 4-dimethylaminopyridine, 1,5-diazabicyclo[4,3,0]nonene-5 (DBN), 1,5-diazabicyclo[5,4,0]undecene-5 (DBU) or 1,4-diazabicyclo[2,2,2]octane (DABCO); an inorganic basic compound such as potassium carbonate, sodium carbonate, potassium hydrogencarbonate or sodium hydrogencarbonate, can be exemplified. The reaction can be achieved at about 0° to 150° C., preferably about 0° to 100° C., for about 1 to 30 hours. The ratio of the amount of a compound of the formula (1a), (1c) or (1l) to the amount of the phosphorus compound and a carboxylic acid of the formula (3), generally, at least an equimolar amount, preferably 1 to 3 times the molar quantity of the latter can be used to the former.

In the above-mentioned Reaction process formula-1, a compound of the formula (1a) or (1b) may be esterified with an alcohol (4) to obtain the corresponding objective compound of the formula (1c) or (1d).

This esterification reaction can be carried out under reaction conditions similar to those in a conventional esterification reaction, for example (i) by dehydrocondensing in the presence of a dehydrating agent in a solvent; or (ii) by reacting in the presence of an acidic or basic catalyst in a suitable solvent. As to the solvent used in method (i), a halogenated hydrocarbon such as methylene chloride, chloroform or dichloroethane; an aromatic hydrocarbon such as benzene, toluene or xylene; an ether such as diethyl ether, tetrahydrofuran or dimethoxyethane; an aprotic polar solvent such as dimethylformamide, dimethyl sulfoxide of hexamethylphosphoryl triamide; can be exemplified.

As to the dehydrating agent, for example dicyclohexylcarbodiimide or carbonyldiimidazole can be exemplified. The ratio of the amount of a compound of the formula (1a) or (1b) used to the amount of an alcohol of the formula (4) may be at least an equimolar amount, preferably an equimolar to 1.5 times the molar quantity of the latter to the former. The ratio of the amount of the dehydrating agent used to the amount of a compound of the formula (1a) or (1b) is at least an equimolar amount, preferably an equimolar to 1.5 times the molar quantity of the former to the latter. The reaction temperature is generally from a room temperature to 150° C., preferably 50° to 100° C., and the reaction is generally completed in 1 to 10 hours. As to the acidic catalyst used in the method of (ii), an inorganic acid such as hydrogenchloride gas, concentrated sulfuric acid, a phosphoric acid, a polyphosphoric acid, boron trifluoride or perchloric acid; an organic acid such as trifluoroacetic acid, trifluoromethanesulfonic acid, naphthalenesulfonic acid, p-toluenesulfonic acid, benzenesulfonic acid or ethanesulfornic acid; an acid anhydride such as trichloromethanesulfonic acid anhydride or trifluoromethanesulfornic acid anhydride; thionyl chloride; or acetone dimethyl acetal, can be exemplified. Further, an acidic ion-exchange resin can also be used as the catalyst in the present invention. As to the basic catalyst, any basic catalyst which is known in the art can be used, for example an inorganic basic compound such as sodium hydroxide, potassium hydroxide, sodium carbonate, potassium carbonate, sodium hydrogencarbonate, potassium hydrogencarbonate or silver carbonate; an alcoholate such as sodium methylate or sodium ethylate; can be exemplified. This reaction can be carried out in the absence or presence of a solvent. As to the solvent to be used in the reaction, any solvent used in a common esterification reaction can advantageously be used, specifically, an aromatic hydrocarbon such as benzene, toluene or xylene; a halogenated hydrocarbon such as dichloromethane, dichloroethane, chloroform or carbon tetrachloride; an ether such as diethyl ether, tetrahydrofuran, dioxane or ethylene glycol monomethyl ether; can be exemplified. Further, the reaction can advantageously be carried out by using a drying agent such as anhydrous calcium chloride, anhydrous copper sulfate, anhydrous calcium sulfate or phosphorus pentoxide. The ratio of the amount of a compound of the formula (1a) or (1b) to the amount of an alcohol (4) is not specifically restricted and may be selected from a wide range, in case that in the absence of a solvent, an alcohol (4) is used in a great excess amount, while in the presence of a solvent, an equimolar to 5 times the molar quantity, preferably an equimolar to 2 times the molar quantity of the alcohol (4) is used to the quantity of the compound of the formula (1a) or (1b). The reaction temperature is not specifically restricted, and generally from −20° to 200° C., preferably from 0° to 150° C., and the reaction is generally completed in 1 to 20 hours.

In the above-mentioned reaction process formula-1, a compound of the formula (1a) can be prepared by hydrolyzing a compound of the formula (1b), (1c), (1d), (1n), (1l) or (1m) under a condition similar to that in the hydrolyzing of a compound of the formula (2). The amide-bond formation reaction of a compound of the formula (1a) or (1b) can be carried out under a condition similar to that in the amide-bond formation reaction of a compound of the formula (1a), (1c), or (1l).

The reaction of a compound of the formula (1a), (1l) or (1c) with a compound of the formula (5) is completed in the absence of a solvent or generally in the presence of an inert solvent, generally under a temperature condition of at a room temperature to 200° C., preferably at a room temperature to 120° C. for several hours to 24 hours. As to the inert solvent, an ether such as dioxane, tetrahydrofuran or ethylene glycol dimethyl ether; an aromatic hydrocarbon such as benzene, toluene or xylene; a lower alcohol such as methanol, ethanol, or isopropanol; a polar solvent such as dimethylformamide, dimethyl sulfoxide, hexamethylphosphoryl triamide, acetone or acetonitrile, can be used. The reaction can advantageously be carried out by using a basic compound as a deacidifying agent. As to the basic compound, potassium carbonate, sodium carbonate, sodium hydroxide, sodium hydrogencarbonate, sodium amide, sodium hydride, a tertiary amine such as triethylamine, tripropylamine, pyridine or quinoline, can be exemplified. Furthermore, the reaction can be carried out, by adding an alkali metal iodide such as potassium iodide or sodium iodide; or hexamethylphosphoryl triamide as the reaciton accelarator, if necessary. The ratio of the amount of a compound of the formula (1a), (1l) or (1c) to the amount of a compound of the formula (5) is not specifically restricted, and may be selected from a wide range, generally, an equimolar quantity to an excess amount, preferably an equimolar to 5 times the molar quantity of the latter is used to the former.

By reaction conditions similar to those employed in the reaction of the compound (1a), (1c) or (1l) with the compound (5), the above-mentioned compound (1o), (1p) or (1q) can be sulfonylized to prepare a compound represented by the general formula (1r),

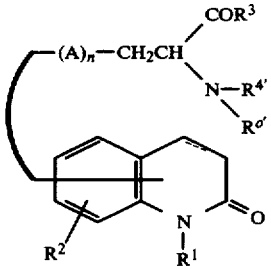

(1r)

wherein $R^1$, $R^2$, $R^3$, $R^{4'}$, A, n and the carbon-carbon bond between 3- and 4-positions in the carbostyril skeleton are the same as defined above; and $R^{o'}$ is a phenylsulfonyl group (which may have, as the substituents, lower alkyl groups or halogen atoms).

Furthermore, among the compounds of the general formula (1), compound having phenylsulfonyl group (which may have, as the substituents, lower alkyl groups or halogen atoms) as the $R^4$ can be introduced to a compound represented by the general formula

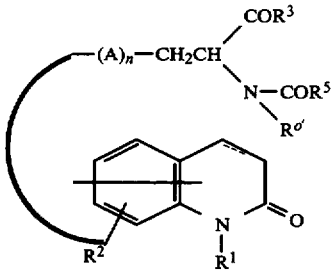

(1s)

wherein $R^1$, $R^2$, $R^3$, $R^5$, $R^{o'}$, A, n and the carbon-carbon bond between 3- and 4-positions in the carbostyril skeleton are the same as defined above, by a method under conditions similar to those employed in the acylation of the compound (1a) with the compound (3).

The compound (1r) thus prepared can be introduced to the compound (1o) by treating in water, a lower alcohol such as methanol ethanol or isopropanol, or with a mixed solvent consisting of water and a lower alcohol, in the presence of a mineral acid such as sulfuric acid, hydrochloric acid or hydrobromic acid, at a room temperature to 150° C., preferably at 60° to 120° C., for about 30 minutes to 15 hours.

Compound of the present invention can also be prepared by methods as shown in the following reaction process formula-II.

[Reaction process formula-II]

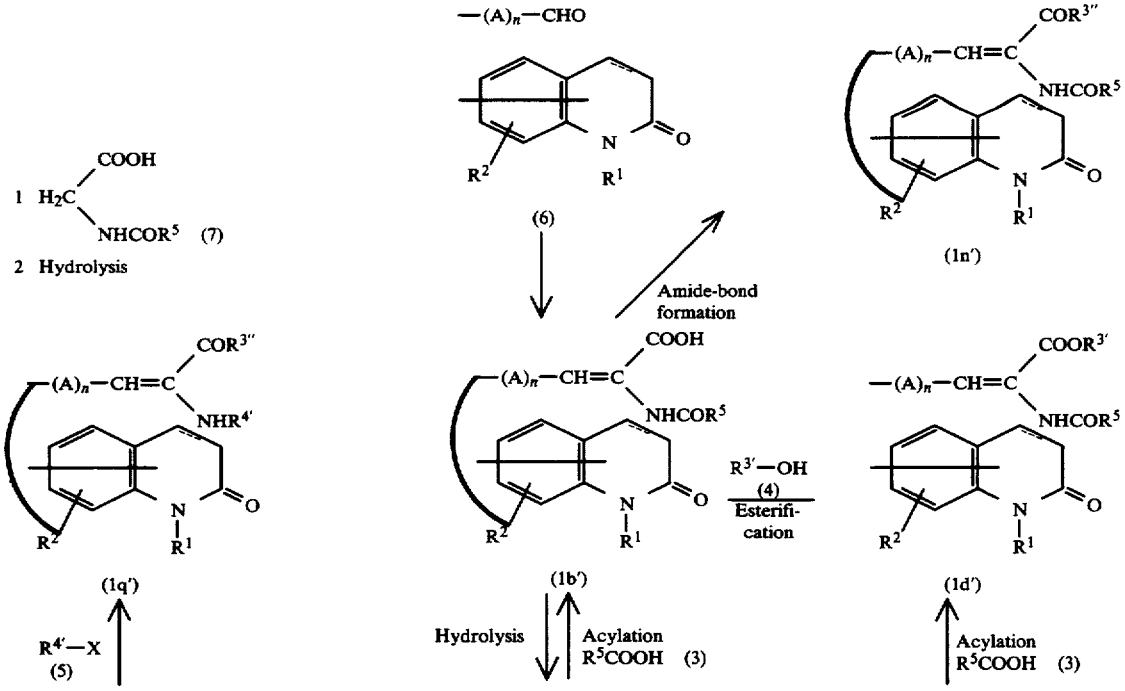

-continued

[Reaction process formula-II]

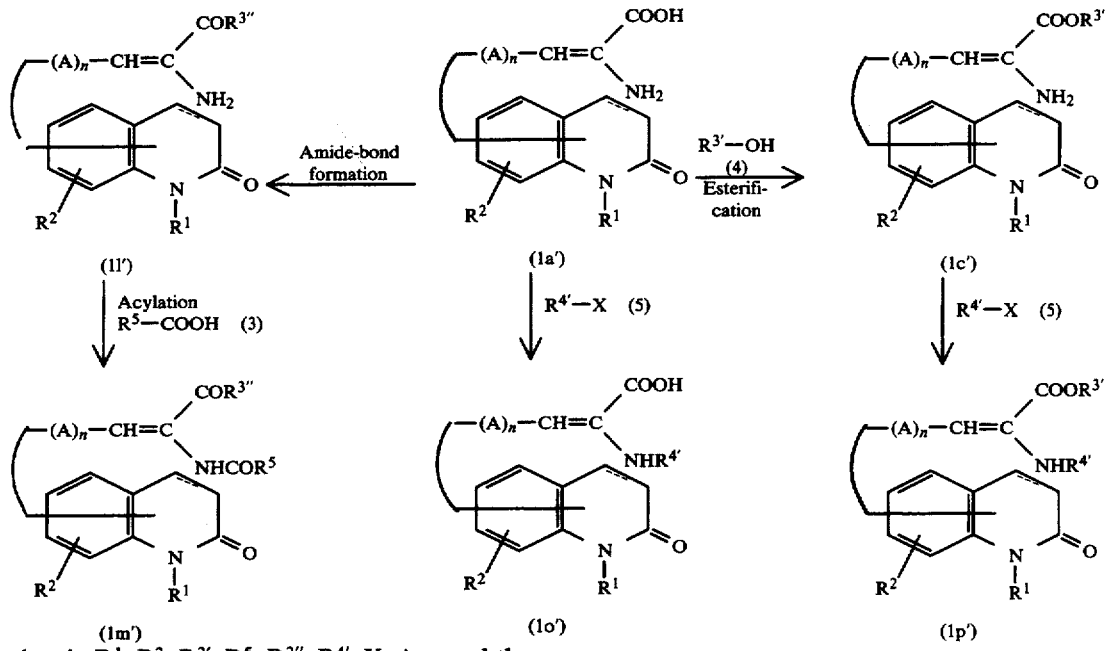

wherein $R^1$, $R^2$, $R^{3'}$, $R^5$, $R^{3''}$, $R^{4'}$, X, A, n and the carbon-carbon bond between 3- and 4-positions in the carbostyril skeleton are the same as defined above.

Thus, compound of the formula (6) is reacted with a compound of the formula (7), then the intermediate formed is hydrolyzed, further the obtained product is hydrolyzed, acylated, esterified or treated by a process of combination of these reactions to obtain the desired carbostyril derivative.

The reaction of a compound of the formula (6) with a compound of the formula (7) can be carried out in the presence of a basic compound in a suitable solvent. As to the basic compound used in the reaction, an organic amine such as triethylamine, trimethylamine, pyridine, piperidine, N-methylmorpholine or 4-dimethylaminopyridine; an inorganic basic compound such as potassium hydroxide, sodium hydroxide, sodium hydride, sodium amide, sodium carbonate, potassium carbonate, sodium hydrogencarbonate or potassium hydrogencarbonate; an alkali metal salt of aliphatic fatty acid such as sodium acetate potassium acetate or sodium propionate; an alkali metal alcoholate such as sodium methylate or sodium ethylate.

As to the solvent used in the reaction, an alcohol such as methanol, ethanol or isopropanol; a hydrocarbon such as hexane or cyclohexane; an ether such as diethylene glycol dimethyl ether, dioxane, tetrahydrofuran or diethyl ether; an ester such as ethyl acetate or methyl acetate; an aromatic hydrocarbon such as benzene, toluene or xylene; as well as water, acetic acid, acetic anhydride and pyridine can be exemplified.

The ratio of the amount of a compound of the formula (6) to the amount of a compound of the formula (7) is at least an equimolar quantity, preferably an equimolar to 2 times the molar quantity of the latter to the former. The reaction is generally carried out at 50° to 200° C., preferably 80° to 150° C. for about 30 minutes to 50 hours.

By a reaction of a compound of the formula (6) with a compound of the formula (7), an intermediate product of the following formula is obtained:

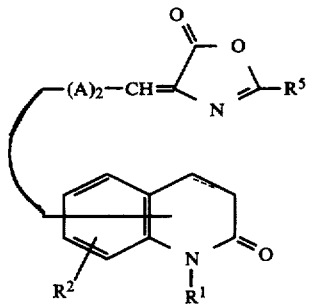

[wherein $R^1$, $R^2$, $R^5$, A, n and the carbon-carbon bond between 3- and 4-positions in the carbosyril skeleton are the same as defined above]. This intermediate product can easily be hydrolyzed, under a condition for example, by refluxing in water-acetone to obtain a compound of the formula (1b'). Thus obtained compound of the formula (1b') can easily be converted into a compound of the formula (1a') under a condition similar to that in the hydrolysis of a compound of the formula (2) in the above-mentioned reaction process formula-I.

Furthermore, a compound of the formula (1b') or (1a') can also be esterified by a method similar to that described in the esterifidation reaction in the above-mentioned reaction process formula-I, by using a compound of the formula (4), to prepare corresponding compound of the formula (1d') or (1c') respectively. Additionally, a compound of the formula (1a'), (1c') or (11') can also be acylated by a method similar to that described in the acylation reaction in the above-mentioned reaction process formula-I, by using a compound of the formula (3), to prepare corresponding compound of the formula (1b'), (1d') or (1m') respectively.

A compound of the formula (1b') or (1a') can be treated by a method similar to that described in the amidation reaction in the above-mentioned reaction process formula-I to prepare a compound of the formula (11') or (1n') respectively.

The reaction of a compound of the formula (1a'), (1l') or (1c') with a compound of the formula (5) can be carried out under a condition similar to that described in the reaction of a compound of the formula (1a), (1l) or (1c) with a compound of the formula (5) in the above-mentioned reaction process formula-I.

Further, a compound of the formula (1c'), (1d'), (1l'), (1m') or (1n') can easily be hydrolyzed to introduced a compound of the formula (1a') by a method under conditions similar to those employed in the hydrolysis reaction of a compound of the formula (2) in the reaction process formula-I.

The compound of the general formula (1o'), (1p'), or (1q') can be introduced to a compound of the general formula

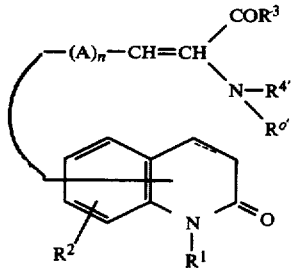

(1r')

wherein $R^1$, $R^2$, $R^3$, $R^{4'}$, $R^{o'}$, A, n and the carbon-carbon bond between 3- and 4-positions in the carbostyril skeleton are the same as defined above, by sulfolating under conditions similar to those employed in the reaction of (1a'), (1c') or (1l') with a compound of the formula (5).

Among the compound of the general formula (1), compounds having a phenylsulfonyl group (which may have, as the substituents, lower alkyl groups or halogen atoms) as well as the carbon-carbon bond of —CH C< in the side-chain of the formula

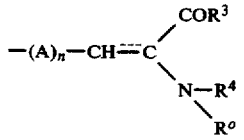

is a double bond, can be introduced to a compound, of the general formula,

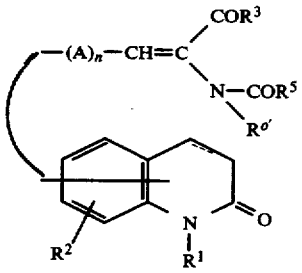

(1s')

wherein $R^1$, $R^2$, $R^3$, $R^5$, $R^{o'}$, A, n and the carbon-carbon bond between 3- and 4-positions in the carbostyril skeleton are the same as defined above, by acylating under conditions similar to those employed in the reaction of the compound of the general formula (1a) with the compound of the formula (3).

The compound of the formula (1r') can be introduced to a compound of the formula (1o') by reaction conditions similar to those employed in the reaction of the compound of the general formula (1r).

Among the compounds of the present invention, those having a single bond in the carbon-carbon bond of —CH C< in the side-chain of the formula

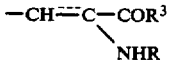

can be prepared by reducing a corresponding compound in which the carbon-carbon bond is a double bond, as shown in the following reaction process formula-III.

[Reaction process formula-III]

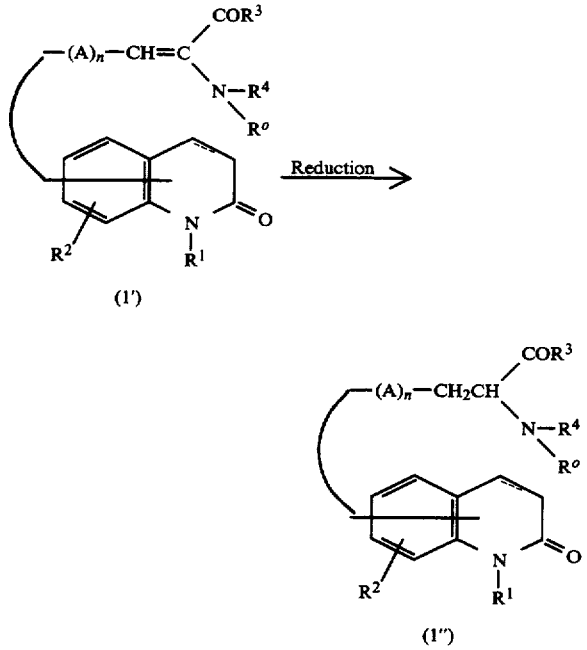

(1')

(1'')

wherein $R^o$, $R^1$, $R^2$, $R^3$, $R^4$, A, n and the carbon-carbon bond between 3- and 4-positions in the carbosyril skeleton are the same as defined above.

The reduction reaction is generally carried out by conducting catalytic reduction in the presence of a suitable reducing catalyst. As to the catalyst to be used, usual catalytic reducing catalysts, for example platinum, platinum oxide, palladium black, palladium carbon or Raney nickel are included. The amount of the catalyst used in generally in the range about 0.2 to 0.5 times by weight to the amount of a compound of (1'). The catalytic reduction is carried out in a solvent, for example water, methanol, ethanol, isopropanol, tetrahydrofuran or diethyl ether, under 1 to 10 atmospheric pressure, preferably 1 to 3 atmospheric pressure of hydrogen gas, at −30° C. to the boiling point of the solvent preferably at 0° C. to around a room temperature, with well agitating condition.

Furthermore, a compound of the present invention can be converted into other compound of the present invention by methods shown in the following reaction process formulas-IV to VI.

[Reaction process formula-IV]

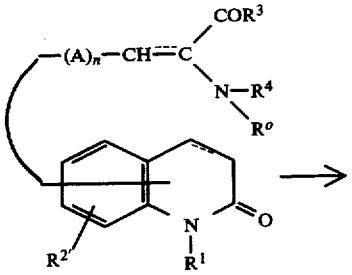

(1e)

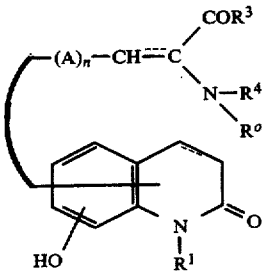

(1f)

wherein $R^o$, $R^1$, $R^3$, $R^4$, A, n and the carbon-carbon bond between 3- and 4-positions in the carbostyril skeleton are the same as defined above; and $R^{2'}$ is a lower alkoxy group.

The reaction to obtain a compound of the formula (1f) from a compound of the formula (1e) is carried out by treating a compound of the formula (1e) in a hydrobromic acid solution at 50° to 150° C. for about 5 to 10 hours.

[Reaction process formula-V]

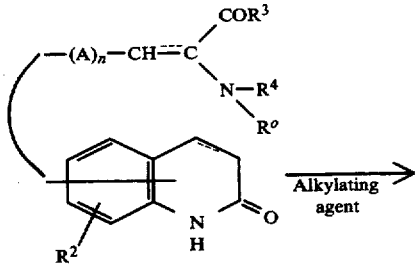

(1g)

-continued

[Reaction process formula-V]

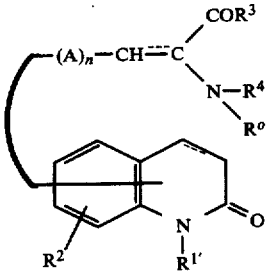

(1h)

wherein $R^o$, $R^2$, $R^3$, $R^4$, A, n and the carbon-carbon bond between 3- and 4-positions in the carbostyril skeleton are the same as defined above; $R^{1'}$ is a lower alkyl group, a lower alkenyl group, a lower alkynyl group or a phenyl-lower alkyl group.

The alkylating reaction of a compound of the formula (1g) is carried out in the presence of a basic compound such as sodium hydride, potassium hydride, potassium metal, sodium metal, sodium amide, potassium amide, sodium hydroxide, potassium hydroxide, sodium carbonate, potassium carbonate, sodium hydrogencarbonate or potassium hydrogencarbonate, in a suitable solvent.

As to the solvent used, there are exemplified an ether such as dioxane, tetrahydrofuran, diethyl ether or diethylene glycol dimethyl ether; an aromatic hydrocarbon such as benzene, toluene, xylene or chlorobenzene; a polar solvent such as dimethylformamide, dimethyl sulfoxide, hexamethylphosphoryl triamide or ammonia water; or a mixture of these solvents.

As to the alkylating agent, a halogenated alkyl of the formula $R^{1'}$-X (wherein $R^{1'}$ is the same as defined above; X is a halogen atom); a dialkyl sulfate such as dimethyl sulfate or diethyl sulfate; a toluenesulfonate such as benzyl p-toluenesulfonate or methyl p-toluenesulfonate. The ratio of the amount of the alkylating agent to the amount of a compound of the formula (1g) is not specifically restricted, and generally at least an equimolar quantity, preferably an equimolar to 2 times the molar quantity of the former is used to the latter. The reaction is carried out generally about at 0° to 70° C., preferably at 0° C. to a room temperature, and generally completed in 30 minutes to 12 hours.

[Reaction process formula-VI]

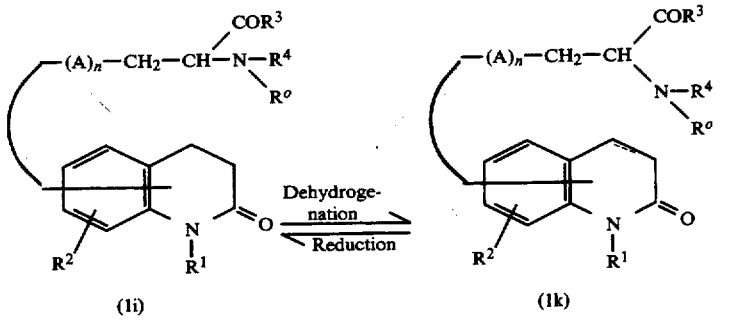

(1i) (1k)

wherein $R^1$, $R^2$, $R^3$, $R^4$, A and n are the same as defined above.

The dehydrogenation of a compound of the formula (1i) to obtain a compound of the formula (1k) is carried out in a suitable solvent in the presence of a dehydrogenating agent. As to the dehydrogenating agent used, there are exemplified a benzoquinone such as 2,3-dichloro-5,6-dicyanobenzoquinone or 2,3,5,6-tetrachlorobenzoquinone (a common name is chloranil); a halogenating agent such as N-bromosuccinimide, N-chlorosuccinimide or bromine; a dehydrogenating catalyst such as selenium dioxide, palladium-carbon, palladium black, palladium oxide or Raney nickel. The ratio of the amount of the dehydrogenating agent used is not specifically restricted, in case of the halogenating agent, 1 to 5 times the molar quantity, preferably 1 to 2 times the molar quantity of the halogenating agent is used to the compound of (1i); in case of the dehydrogenating catalyst, generally an excess amount thereof is used preferably; in case of other types of the dehydrogenating agent, generally an equimolar quantity to an excess amount thereof is used. As to the solvent, an ether such as dioxane, tetrahydrofuran, methoxyethane or dimethoxythane; an aromatic hydrocarbon such as benzene, toluene, xylene, or cumene; a halogenated hydrocarbon such as dichloroethane, dichloromethane, chloroform or carbon tetrachloride; an alcohol such as butanol, amyl alcohol or hexanol; a polar protic solvent such as acetic acid, aprotic polar solvent such as dimethylformamide, dimethyl sulfoxide or hexamethylphosphoryl triamide, can be exemplified. The reaction is generally carried out at a room temperature to 300° C., preferably at a room temperature to 200° C., and the reaction is completed in about 1 to 40 hours.

Further, the reduction of the compound of the formula (1k) to prepare a compound of the formula (1i) is carried out under a condition of usual catalytic reduction in a suitable solvent in the presence of a metallic catalyst. As to the catalyst used, there are exemplified a metallic catalyst such as palladium, palladium carbon, platinum and Raney nickel. As to the solvent used, examples are water, methanol, ethanol, isopropanol, dioxane, tetrahydrofuran, hexane, cyclohexane, ethyl acetate, and a mixture of these solvents.

The catalytic reduction may be carried out under normal hydrogen pressure or under pressure, usually under a normal hydrogen pressure to 20 kg/cm$^2$, preferably under a normal hydrogen pressure to 10 kg/cm$^2$, at 0° to 150° C., preferably at a room temperature to 100° C.

Among the compound of the general formula (1), those having hydroxyl group as the symbol $R^2$, can also be prepared by dealkylating a compound in which $R^2$ is a lower alkoxy group with an aqueous solution of hydrobromic acid under heating condition.

Further, the compound of the general formula (1), having hydroxyl group as the symbol $R^2$ can also be prepared by hydrolysing a compound of the general formula (1) in which $R^2$ is a benzoyloxy group (which may have, as the substituents, halogen atoms). The hydrolysis can be carried out in a suitable solvent in the presence of an acid or basic compound. As to the solvent used, examples include water; lower alcohol such as methanol, ethanol or isopropanol, ethers such as dioxane or tetrahydrofuran; or a mixture of these solvents. As to the acid used, examples include mineral acids such as hydrochloric acid, hydrobromic acid or sulfuric acid. As to the basic compounds used, examples include metal hydroxide such as sodium hydroxide, potassium hydroxide or calcium hydroxide. The reaction is generally carried out at a room temperature to 150° C., preferably at 80° to 120° C., and is completed generally in 1 to 50 hours.

Among the compound of the general formula (1), those having lower alkoxy group as the symbol $R^2$ can be prepared by alkylating a corresponding compound having hydroxyl group as the symbol $R^2$. As to the alkylating agent used in the alkylation reaction, examples include lower alkyl halide such as methyl iodide, ethyl chloride and tert-butyl bromide; dimethyl sulfate and diethyl sulfate. Further other types of alkylating agent such as diazomethane, can also be used. The reaction is carried out in an inert solvent for example, a ketone such as acetone or methyl ethyl ketons; an ether such as diethyl ether or dioxane; an aromatic hydrocarbon such as benzene, toluene or xylene; water; pyridine; dimethlformamide; dimethyl sulfoxide, or hexamethylphosphoryl triamide.

The alkylation can also be carried out by using the basic compound used in the following acylating reaction. Further, the alkylation can be carried out by using silver oxide as the catalyst. The reaction is carried out at a temperature of ranging from 0° C. to the boiling point of the solvent used. The ratio of the amount of the alkylating agent to the amount of the compound of the formula (1), having hydroxyl group as the symbol $R^2$ is usually in the range of 1 to 3 times the molar quantity. The reaction is generally completed in 1 to 15 hours.

Among the compound of the general formula (1), those having benzoyloxy group (which may have, as the substituents, halogen atoms) can be preapred by acylating, i.e., benzoylating a corresponding compound in which $R^2$ is hydroxyl group. As to the benzoylating agent used, examples include benzoyl halide such as p-chlorobenzoyl chloride and benzoyl chloride; benzoic anhydride and benzoic acid. In using the acid anhydride or acid halide as the acylating agent, the acylating reaction is carried out in the presence of a basic compound. As to the basic compound used, an alkali metal such as sodium metal or potassium metal; an alkali metal hydroxide, carbonate or hydrogencarbonate; an aromatic amine such as pyridine, or piperidine. The reaction can be carried out in the absence or presence of a solvent. As to the solvent used, examples include ketones such as acetone and methyl ethyl ketone; ethers such as diethyl ether and dioxane; aromatic hydrocarbons such as benzene, toluene and xylene, water and pyridine.

The ratio of the acylating agent used to the amount of the starting material is at least an equimolar quantity, and generally an equimolar to a large excess amount of the former to the latter. The reaction is carried out at 0° to 150° C., and generally at 0° to 80° C. The reaction is completed in 0.5 to 10 hours. In using an acid such as benzoic acid as the acylating agent, the reaction is advantageously proceeded by adding a mineral acid such as sulfuric acid, or hydrochloric acid; and sulfonic acid such as p-toluenesulfonic acid, benzenesulfonic acid or ethanesulfonic acid, in the reaction system, and keeping the reaction system at a temperature of 50° to 120° C.

Among the compound of the present invention represented by the general formula (1), these having a hydrogen atom for the symbol $R^1$, and also having a double carbon-carbon bond between 3- and 4-positions in the carbostyril skeleton may exist as lactam-latim tautomeric forms as shown in the following equation:

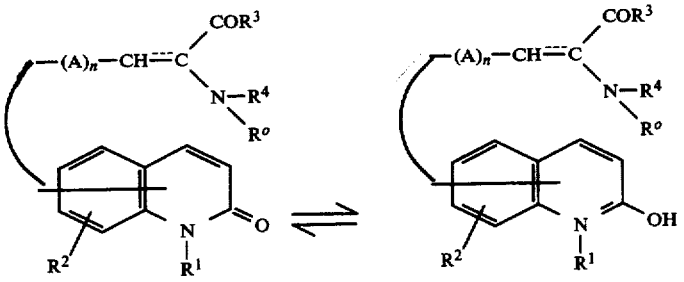

wherein $R^o$, $R^2$, $R^3$, $R^4$, A and n are the same as defined above.

Among the compounds represented by the general formula (1), the compounds having acidic group can easily from salts with pharmaceutically acceptable bases. Such bases include inorganic bases for example metallic hydroxides such as sodium hydroxide, potassium hydroxide, and calcium hydroxide; alkali metal carbonates and hydrogencarbonates such as sodium carbonate and sodium hydrogencarbonate; alkali metal alcoholates such as sodium methylate and potassium ethylate.

Alternatively, among the compounds represented by the general formula (1), the compounds having basic group can easily form salts with pharmaceutically acceptable acids. Such acids include inorganic acids for example sulfuric acid, nitric acid, hydrochloric acid, hydrobromic acid; organic acids for example acetic acid, p-toluenesulfonic acid, ethanesulfonic acid, oxalic acid, maleic acid, succinic acid and benzoic acid.

Compounds of the present invention as obtained by the above processes can easily be isolated and purified from the reaction system by the usual separation techniques such as distillation, recrystallization, column chromatography, preparative thin layer chromatography and solvent extraction.

The compound of the general formula (2) used as the starting material in the above-mentioned reaction process formula-I is a novel compound, and it can be prepared according to the process shown in the following reaction process formula-VII.

[Reaction process formula-VII]

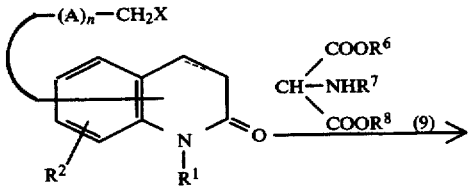

(8)

wherein $R^1$, $R^2$, $R^6$, $R^7$, $R^8$, A, n and the carbon-carbon bond between 3- and 4-positions in the carbostyril skeleton are the same as defined above; and X is a halogen atom.

The compound of the general formula (2) is prepared by reacting the compound of the general formula (8) with the compound of the general formula (9). This reaction is carried out in a suitable solvent, in the presence of a basic compound, at a room temperature to 200° C., preferably at 60° to 120° C., for 1 to 24 hours. As to the inert solvent used, there are exemplified ethers such as dioxane, tetrahydrofuran ethylene glycol dimethyl ether and diethyl ether; aromatic hydrocarbons such as benzene, toluene and xylene; lower alcohols such methanol, ethanol and isopropanol; polar solvents such dimethylformamide, and dimethyl sulfoxide. As to the basic compound used, there can be used inorganic basic compounds such as calcium carbonate, sodium carbonate, potassium carbonate, sodium hydrogencarbonate, sodium hydroxide, potassium hydroxide, sodium amide, sodium hydride, potassium hydride, sodium methylate and sodium ethylate; tertiary amines such as triethylamine, tripropylamine, pyridine and quinolinn; and other basic compounds selected from a wide range.

The above-mentioned reaction may be carried out by adding and alkali metal iodide such as potassium iodide or sodium iodide as the reaction accelerator.

The ratio of the amount of the compound (8) to the amount of the compound (9) is not specifically restricted, and usually an equimolar to large excess, preferably an equimolar to 5 times the molar quantity, more preferably an equimolar to 1.2 times the molar quantity of the latter is used to the former.

The compound represented by the other type of general formula (2) can be prepared from the compound (2) by processes according to the following reaction process formulas-VIII and IX.

[Reaction process formula-VIII]

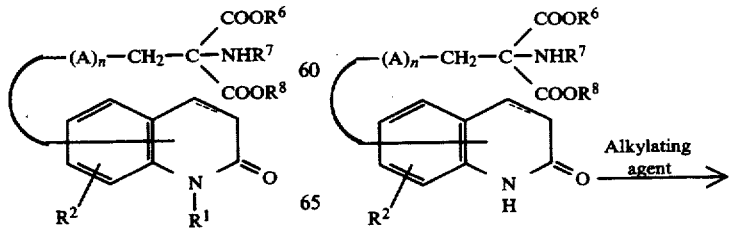

(2) (2a)

-continued

[Reaction process formula-VIII]

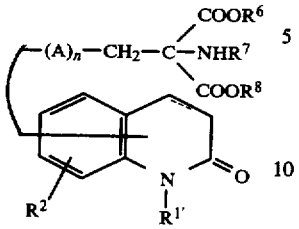

(2b)

wherein $R^2$, $R^6$, $R^7$, $R^8$, $R^{1'}$, A, n and the carbon-carbon bond between 3- and 4-positions in the carbostyril skeleton are the same as defined above.

In the above-mentioned reaction process formula-VIII, the reaction of the compound (2a) with the alkylating agent can be carried out under conditions similar to those mentioned in the reaction of the compound (1g) with the alkylating agent according to the reaction process formula-V.

[Reaction process formula-IX]

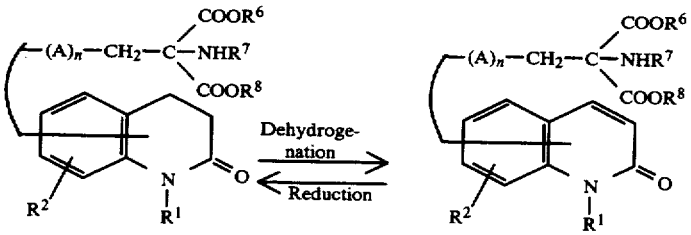

(2c) (2d)

wherein $R^1$, $R^2$, $R^6$, $R^7$, $R^8$, A, n and the carbon-carbon bond between 3- and 4-positions in the carbostyril skeleton are the same as defined above.

The dehydrogenation and reduction in the reaction process formula-IX can be carried out under conditions similar to those employed in the dehydrogenation of the compound (1i) and the reduction of the compound (1k) according to the reaction process formula-VI.

Some compounds represented by the general formula (5) used as the starting material in the reaction process formula-II are known, and further including novel compounds and such novel compounds can be prepared by a method as shown in the following reaction process formula-X.

[Reaction process formula-X]

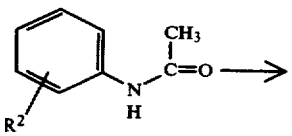

(10)

-continued

[Reaction process formula-X]

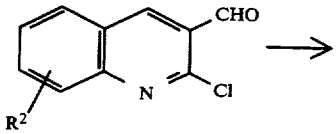

(11)

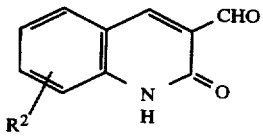

(6)

wherein $R^2$ is the same as defined above.

In the above-mentioned reaction process formula-X, the reaction to obtain the compound (11) by cyclizing the compound (10) can be carried out in the presence of N,N-substituted-formamide and an acid catalyst (which is generally called as Vilsmeier reagent), in a suitable solvent or without the solvent. As to the N,N-substituted-formamide used, there are exemplified N,N-dimethylformamide, N,N-diethylformamide, N-ethyl-N-methylformamide and N-methyl-N-phenylformamide. As to the acid catalyst used, there are exemplified phosphorus oxychloride, thionyl chloride and phosgene. As to the solvent used, there are exemplified halogenated hydrocarbons such as chloroform, 1,2-dichloroethane and 1,2-dichloroethylene; aromatic hydrocarbons such as chlorobenzene and 1,2-dichlorobenzene. The ratio of the amount of the N,N-substitued-formamide and the acid catalyst to the amount of the compound of the general formula (10) may be usually a large excess amount, preferably, 2 to 5 times the molar quantity of the former and 5 to 10 times the molar quantity of the latter to the compound of (10). The reaction temperature may be usually at 0° to 150° C., preferably around at 50° to 100° C., and the reaction is completed about in 3 to 24 hours.

The reaction for obtaining the compound (6a) from the compound (11) is achieved by heating the compound (11) in the presence of a hydrohalogenic acid such as hydrochloric acid or hydrobromic acid; an inorganic acid such as sulfuric acid or phosphoric acid; an alkali metal hydroxide such as potassium hydroxide or sodium hydroxide; or an inorganic alkaline compound such as sodium carbonate, potassium carbonate or potassium hydrogencarbonate; or an organic acid such as acetic acid, at a temperature of 50° to 150° C., preferably at a temperature of 70° to 120° C., for about 0.5 to 24 hours.

The compound (8) as used for the starting material in the reaction process formula-VII can be prepared by a method according to the reaction process formula-XI as follows:

[Reaction process formula-XI]

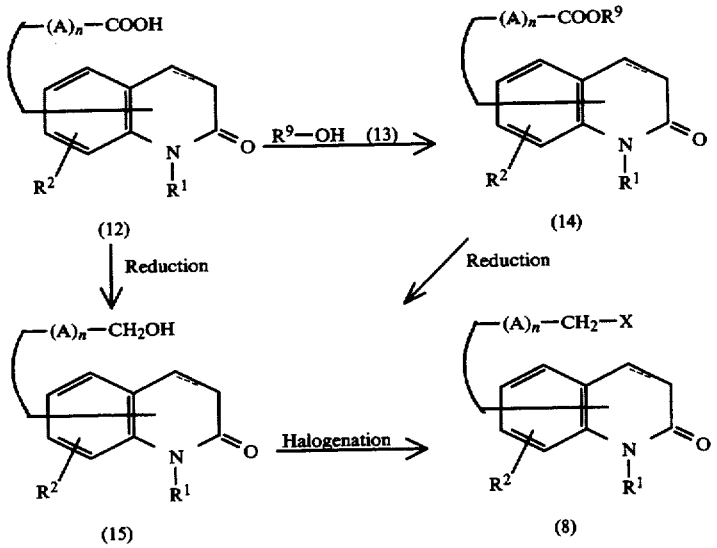

wherein $R^1$, $R^2$, A, n and the carbon-carbon bond between 3- and 4-positions in the carbostyril skeleton are the same as defined above; $R^9$ is a lower alkyl group or a group of the formula

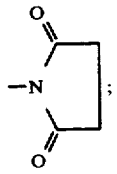

X is a halogen atom.

In the above-mentioned reaction process formula-XI, the reaction of the compound (12) with the compound (13) can be carried out under the conditions quite similar to those in the esterification reaction of the compound (1a) or (1b) with the compound (4) in the reaction process formula-I.

The compound (14) thus obtained by the esterification can be derived to the corresponding compound (15) by reducing the compound (14). Further, the compound (15) can also be prepared directly by reducing the compound (12). These reductions can be carried out by using usual hydrogenating-reducing agent. As to the hydrogenating-reducing agents used, sodium borohydride, lithium aluminium hydride and diborane are exemplified. The amount of the hydrogenating-reducing agent is usually at least an equimolar quantity, preferably an equimolar to 3 times the molar quantity thereof to the amounts of the compound (12) or (14). In case of using lithium aluminium hydride as the hydrogenating-reducing agent, the same amount by weight of the reducing agent is preferably used to the amount of the compound (12) or (14). The reduction is carried out usually in a suitable solvent such as water; a lower alcohol for example methanol, ethanol or isopropanol; an ether for example tetrahydrofuran, diethyl ether or diglyme, at about −60° to 50° C., preferably at −30° to a room temperature, for about 10 minutes to 5 hours. In case of using lithium aluminum hydride or diborane as the reducing agent, an anhydrous solvent such as diethyl ether, tetrahydrofuran or diglyme may preferably be used.

The reaction of halogenating the compound (15) to prepare the compound (8) can be carried out under the reaction conditions used in the usual halogenating reaction, for example, by reacting the compound (15) with a halogenating agent in an inert solvent or without the solvent.

As to the halogenating agent used, there are exemplified hydrohalogenic acids such as hydrochloric acid or hydrobromic acid; N,N-diethyl-1,2,2-trichlorovinylamide, phosphorus pentachloride, phosphorus pentabromide, phosphorus oxychloride or thionyl chloride. As to the inert solvent used, an ether such as dioxane or tetrahydrofuran; a halogenated hydrocarbon such as chloroform, methylene chloride or carbon tetrachloride. The ratio of the amount of the compound (15) to the amount of the halogenating agent may be at least an equimolar quantity, usually a large excess amount of the latter is used to the former. The reaction is usually carried out at a room temperature to about 150° C., preferably at a room temperature to 80° C., for about 1 to 6 hours.

Some of the carboxylic acid compounds (12) and their ester compounds (14) as used for the starting materials in the above-mentioned reaction process formula-XI including novel compounds, and these novel compounds can be prepared by methods as shown in the following reaction process formulas-XII to XVI.

[Reaction process formula-XIII]

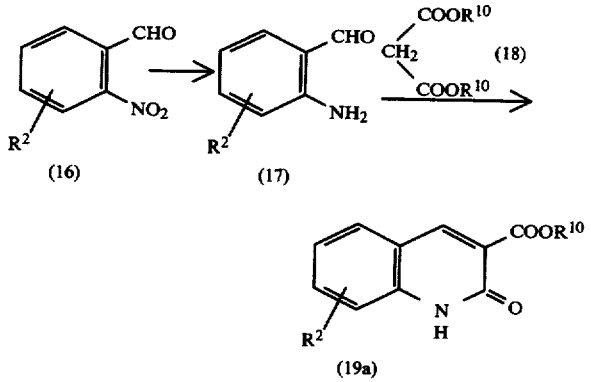

wherein $R^2$ is the same as defined above; $R^{10}$ is a hydrogen atom of a lower alkyl group.

In the above-mentioned reaction process formula-XII, the reduction of the nitro group in the compound (16) is carried out under conditions employed in usual reduction of nitro group, for example (a) by a method using a catalytic reduction catalyst in a suitable inert solvent, or (b) a method by using a mixture of metal or metal salt with an acid, or a metal or metal salt with an alkali metal hydroxide, sulfide or ammonium salt as the reducing agent, in an inert solvent.

In case of carrying out a method of (a) using the catalytic reduction, examples of the solvent used are water; acetic acid; alcohols such as methanol, ethanol, isopropanol, butanol and ethylene glycol; ethers such diethyl ether, dimethyl ether, tetrahydrofuran, dioxane, monoglyme and diglyme; hydrocarbons such as hexane and cyclohexane; esters such as methyl acetate, ethyl acetate, and aprotic solvents such as N,N-dimethylformamide. As to the catalytic reduction catalysts, examples are palladium, palladium black, palladium carbon, platinum, platinum oxide, copper chromite and Raney nickel.

The ratio of the amount of the catalyst to the amount of the compound (16) may be of 0.02 to 1.00 times (by weight) the quantity of the former to the latter. The reaction is usually carried out at −20° to 150° C., preferably at 0° C. to about room temerature, under hydrogen pressure of 1 to 10 atmospheric pressure for abiut 30 minutes to 10 hours. In case of using a method of (b), as to the readucing agent, a combination of iron, zinc, tin or stannic chloride with a mineral acid such as hydrochloric acid or sulfuric acid; or a combination of iron, ferrous sulfate, zinc or tin with an alkali metal hydroxide such as sodium hydroxide, a sulfide such as ammonium sulfide, ammonia water or ammonium salt such as ammonium chloride can be used. As to the inert solvent used, water, acetic acid, methanol, ethanol and dioxane can be exemplified. The reaction temperature and the reaction time may be selected according to the type of the catalyst used, for example, in case of using the combination of ferrous sulfate with ammonia water, the reduction is advantageously carried out at a temperature of about 50° to 150° C., for 30 minutes to 10 hours. The amount of the reducing agent used is generally about at least an equimolar quantity, preferably an equimolar quantity to 5 times the molar quantity to the amount of the compound (16). The reaction of the compound (17) with the compound (18) can be carried out in the presence of a basic compound, in a suitable solvent. As to the basic compound, an inorganic basic compound such as sodium hydroxide, potassium carbonate, sodium hydrogencarbonate, potassium hydrogencarbonate, sodium hydride, sodium methylate or sodium ethylate; or an amine such as triethylamine, pyridine, α-picoline, N,N,-dimethylaniline, N-methylmorpholine, piperidine or pyrolidine can be used. As to the solvent used, an ether such as dioxane, tetrahydrofuran, gylme or diglyme; an aromatic hydrocarbon such as toluene or xylene; a lower alcohol such as methanol, ethanol or isopropanol; a polar solvent such as dimethyl sulfoxide or dimethylformamide. The reaction is carried out at a room temperature to 150° C., preferably at 60° to 120° C., for about 1 to 24 hours. The ratio of the amount of the compound (17) to the amount of the compound (18) is not specifically restricted and usually an equimolar to a large excess quantity, preferably an equimolar to 5 times the molar quantity of the latter is used to the former.

[Reaction process formula-XIII]

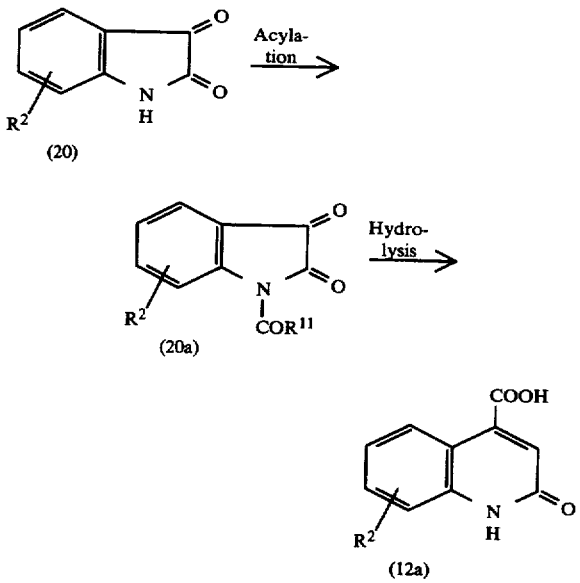

wherein $R^2$ is the same as defined above; and $R^{11}$ is a lower alkyl group.

The reaction as shown in the above-mentioned reaction process formula-XIII is carries out by reacting the compound (20) with an acylating agent represented by the general formula $R^{11}COX^1$ or $(R^{11}CO)_2O$ [wherein $R^{11}$ is the same as defined above; $X^1$ is a halogen atom], then the obtained compound (20a) is hydrolyses to prepare the compound (12a). The reaction of the compound (20) with the acylating agent represented by the formula $R^{11}COX^1$ or $(R^{11}CO)_2O$ is carried out in the presence of absence of a basic compound. As to the basic compound used, examples include alkali metals such as sodium metal and potassium metal; hydroxides, carbonates and hydrogencarbonates of these alkali metals; and aromatic amines such as pyridine and piperidine. The reaction is carries out in the absence or presence of a solvent. As to the solvent used, examples include ketones such as acetone and methyl ethyl ketone; ethers such as diethyl ether and dioxane; aromatic hydrocarbons such as benzene, toluene and xylene; water; and pyridine.

The ratio of the amount of the acylating agent represented by the general formula $R^{11}COX^1$ or $(R^{11}CO)_2O$ used to the amount of the compound represented by the general formula (20) is at least an equimolar quantity of the former to the latter, and usually an equimolar to a large excess quantity of the former to the latter. The reaction is completed in 0.5 to 10 hours.

The hydrolysis reaction of the compound (20a) is carries out in an aqueous solution, in the presence of a hydrolysis catalyst, for example hydroxide of alkali metals such potassium hydroxide and sodium hydroxide; alkali metal compounds such as sodium carbonate, potassium carbonate and sodium hydrogencarbonate, at 50° to 150° C., preferably at 70° to 100° C. for about 0.5 to 10 hours.

[Reaction process formula-XIV]

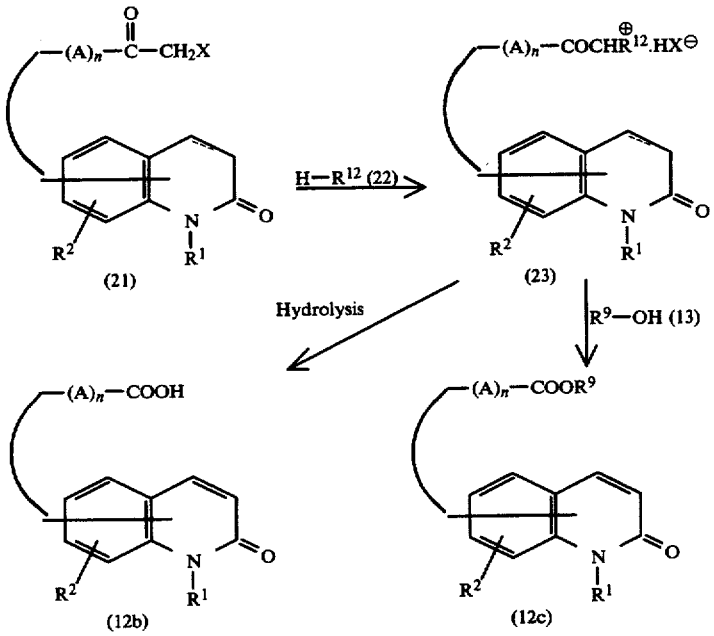

wherein $R^1$, $R^2$, $R^9$, A, n, X and the carbon-carbon bond between 3- and 4-positions in the carbostyril skeleton are the same as defined above; $R^{12}$ is an aromatic amine residue.

In the above-mentioned reaction process formula-XIV, the reaction of the compount (21) with the aromatic amine (22) is carried out in the absence or presence of a suitable solvent. As to the solvent used, any inert solvent which does not give adverse effect to the reaction is used, for example a halogenated hydrocarbon such as chloroform, methylene chloride, dichloromethane or carbon tetrachloride; an ether such as diethyl ether, tetrahydrofuran, dioxane or dimethoxyethane; an alcohol such as methanol, ethanol, isopropanol or butanol; an ester such as methyl acetate, ethyl acetate; an aprotic polar solvent such as N,N-dimethylformamide, dimethyl sulfoxide or hexamethylphosphoryl triamide. As to the aromatic amine, pyridine or quinoline can be exemplified. The amount of the aromatic amine used is at least an equimolar quantity, preferably a large excess quantity thereof to the amount of compound (21). The reaction is carries out at a temperature of 50° to 200° C., preferably at a temperature of 70° to 150° C., for about 3 to 10 hours.

The hydrolysis of the thus obtained compound (23) is carried out in water, in the presence of an inorganic basic compound such as sodium hydroxide or potassium hydroxide at a room temperature to 150° C., for 1 to 10 hours.

The esterification of the compound (23) with the compound (13) is carried out in the presence of a basic compound, in the presence of absence of a solvent. As to the solvent used, examples include a halogenated hydrocarbon such as methylene chloride, chloroform or dichloroethane; an aromatic hydrocarbon such as benzene, toluene or xylene; an ether such as diethyl ether, tetrahydrofuran, dioxane or dimethoxyethane; or an aprotic polar solvent such as N,N-dimethylformamide, dimethyl sulfoxide or hexamethylphosphoryl triamide. As to the basic catalyst used, examples include an organic basic compound such as triethylamine, trimethylamine, pyridine, dimethylaniline, N-methylmorpholine, 4-dimethylaminopyridine, 1,5-diazabicyclo[4,3,0]nonene-5 (DBN), 1,5-diazabicyclo[5,4,0]undecene-5 (DBU) or 1,4-diazabicyclo[2,2,2]octane (DABCO); or an inorganic basic compound such as potassium carbonate, sodium carbonate sodium hydrogencarbonate or potassium hydrogencarbonate.

The ratio of the amount of the basic compound to the amount of the compound (23) may be at least an equimolar, preferably an equimolar to 1.5 times the molar quantity of the former to the amount to the latter. The ratio of the amount of the compound (13) to the amount of the compound (23) may be at least an equimolar quantity, preferably a large excess amount of the former to the amount of the latter. The reaction is carried out usually at a room temperature to 150° C., preferably at about 50° to 100° C., for generally in 30 minutes to 10 hours.

[Reaction process formula-XV]

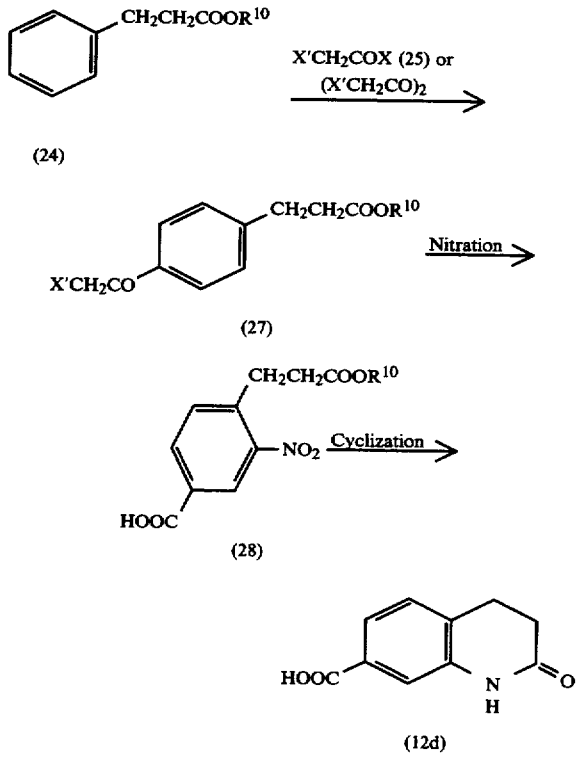

wherein $R^{10}$ and X are the same as defined above; X' is a hydrogen atom or a halogen atom.

In the above-mentioned reaction process formula-XV, the reaction of the compound (24) with the compound (25) or (26) is called as Friedel-Crafts reaction, and is generally carried out in a suitable solvent, in the presence of a Lewis acid. As to the solvent used, any solvent which is used in this type of reaction can also be used advantageously, and example include carbon disulfide, nitrobenzene, chlorobenzene, dichloromethane, dichloroethane, trichloroethane and carbon tetrachloride. As to the Lewis acid used, any Lewis acid which is used in this type of reaction can also be used, and examples include aluminium chloride, zinc chloride, iron chloride, tin chloride, boron tribromide, boron trifluoride and concentrated sulfuric acid. The amount of Lewis acid used may be determined any amount, and is usually about 2 to 6 times the molar quantity, preferably 3 to 4 times the molar quantity to the amount of the compound (24). The ratio of the amount of the compound (25) or (26) to the amount of the compound (24) is usually at least an equimolar quantity, preferably an equimolar to 3 times the molar quantity of the former to the latter. The reaction temperature is usually −50° to 120° C., preferably 0° to 70° C., and the reaction time varied depend on the type of the catalyst and on the reaction temperature, and usually 30 minutes to 24 hours. The nitration of the compound (27) times obtained is carried out under conditions similar to those of usual nitration of an aromatic hydrocarbon, for example by using a nitrating agent, in the absence or presence of a suitable inert solvent. As to the inert solvent, examples include acetic acid, acetic anhydride and concentrated sulfuric acid: As to the nitrating agent used, examples include fumig nitric acid, concentrated nitric acid, a mixed acid consisting of nitric acid and other acid (for example sulfuric acid, fuming sulfuric acid, phosphoric acid or acetic anhydride), a mixture of an alkali metal nitrate such as potassium nitrate, or sodium nitrate with a mineral acid such as fulfuric acid. The amount of the nitrating agent is an equimolar or more, and usually a large excess amount to the amount of the compound (27). The reaction is carried out preferably at −10° C. to a room temperature, for 5 minutes to 4 hours. The compound (28) thus obtained is then reduced and cyclized to introduce the compound (12d). This reaction is carried out under conditions similar to those of the reduction reaction of the compound (16) in the reaction process formula-XI. In case of carrying out this reduction by (a) method using catalytic reduction, the reaction is advantageously proceeded in the presence of a basic compound such as sodium hydroxide or potassium hydroxide. In case of carrying out the reduction by (b) method of using a mixture of metal or metal salt with an acid, the reaction is usually carried out at −50° to 100° C. for 0.5 to 10 hours. For example, in case that a mixture of stannous chloride with hydrochloric acid is used as the reducing agent, the reduction advantageously be carried out around at −20° to 50° C. The amount of the reducing agent used is at least an equimolar amount, usually an equimolar to 3 times the molar quantity to the amount of the starting material. According to the reaction as mentioned above, the nitro group in the compound (28) is reduced and at the same time the cyclization of the compound (28) is proceed to obtain the compound (12d). It should be noted the fact that, in case of carrying out method (a) by using the catalytic catalyst, there are some instances in which the carbonyl group is reduced to methylene group through the reduction, and the reaction conditions properly be selected for the purpose of to avoid such undesirable conversion of the carbonyl group.

[Reaction process formula-XVI]

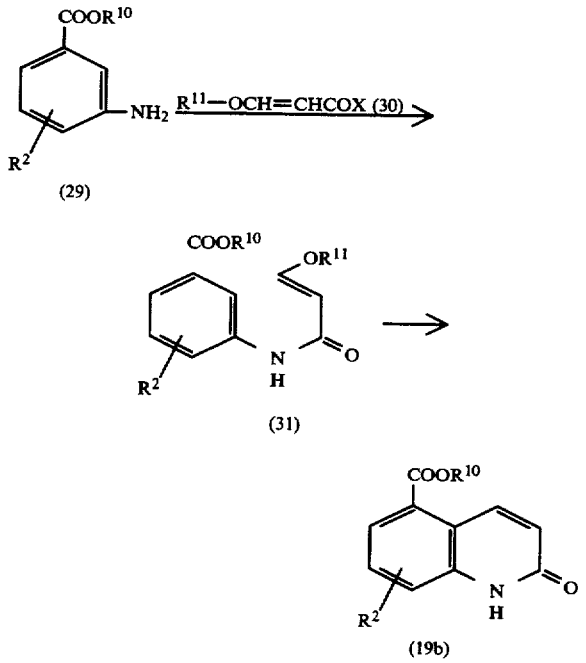

wherein $R^2$, $R^{10}$, $R^{11}$ and X are the same as defined above.

In the above-mentioned reaction process formula-XVI, the reaction of the compound (29) with the compound (30) is generally carried out in the presence of a dehydrohalogenating agent, in the absence or presence of a suitable solvent. As to the dehydrohalogenating agent, generally a basic compound is used for example, an organic basic compound such as triethylamine, trimethylamine, pyridine, dimethylaniline, N-methylmorpholine, 4-dimethylaminopyridine, 1,5-diazabicyclo[4,3,0]nonene-5 (DBN), 1,5-diazabicyclo[5,4,0]undecene-5 (DBU) or 1,4-diazabicyclo[2,2,2]octane (DABCO); an alkali metal compound such as potassium carbonate, sodium carbonate, potassium hydrogencarbonate, sodium hydrogencarbonate, sodium hydroxide, potassium hydroxide, sodium hydride, potassium hydride; silver carbonate; an alkali metal alcoholate such as sodium methylate or sodium ethylate. The compound (30) can also be used as the dehydrohalogenating agent when it is used in a large excess amount. As to the solvent used, examples include a halogenated hydrocarbon such as methylene chloride, chloroform or dichloroethane; an aromatic hydrocarbon such as benzene, toluene or xylene; an ether such as diethyl ether, tetrahydrofuran or dimethoxyethane; an ester such as methyl acetate or ethyl acetate; an aprotic polar solvent such as dimethylformamide, dimethyl sulfoxide or hexamethylphosphoryl triamide; pyridine, acetone, acetonitrile, further an alcohol such as methanol, ethanol, propanol, butanol, 3-methoxy-1-butanol, ethyl cellosolve or methyl cellosolve; or a mixed solvent consisting of two or more of the solvents.

The ratio of the amount of the compound (29) to the amount of the compound (30) is not specifically restricted and can be selected from a wide range, generally at least an equimolar quantity, preferably an equimolar quantity to 5 times the molar quantity of the latter is used to the former. The reaction is generally carried out at −30° to 180° C., preferably about at 0° to 150° C., for 5 minutes to 30 hours.

The cyclization reaction of the compound (31) is carried out in the absence or presence of a suitable solvent, in the presence of an acid. As to the acid used, there is not any specific restriction for selecting the acid, generally common organic or inorganic acid can be used for example hydrochloric acid, hydrobromic acid, sulfuric acid; a Lewis acid such as aluminium chloride, boron trifluoride or titanium tetrachloride; and organic acid such as formic acid, acetic acid, ethanesulfonic acid or p-toluenesulfonic acid. Among these acids, an inorganic acid such as hydrochloric acid, hydrobromic acid or sulfuric acid are preferably used. The amount of the acid used is not specifically restricted, and generally an equivalent amount by weight, preferably 10 to 50 times the amount by weight of the acid is used to the amount of the compound (31). As to the solvent, a common inert solvent can be used, for example water, an alcohol such as methanol, ethanol, or propanol; an ether such as dioxane or tetrahydrofuran; an aromatic hydrocarbon such as benzene, toluene or xylene; a halogenated hydrocarbon such as methylene-chloride, chloroform or carbon tetrachloride, an aprotic polar solvent such as acetone, dimethyl sulfoxide, dimethylformamide, or hexamethylphosphoryl trimide. Among of these solvents, the lower alcohols, the ethers, the water-solble solvents such as acetone, dimethyl sulfoxide, dimethylformamide and hexamethylphophoryl triamide are preferable.

The said reaction is generally carried out at 0° to 100° C., preferably at a room temperature to 60° C., for generally about 5 minutes to 6 hours.

The compounds (19a), (19b), (12a) to (12d) can also be introduced to the compounds (19) and (12) respectively by the method of alkylating as shown in the reaction process formula-V and by the method of dehydrogenation reaction or reduction as shown in the reaction process formulas-VI and IX.

The compound (15) as the intermediate product and the compound (8) in the reaction process formula-XI and the compound (21) as the starting material in the reaction process formula-XIV can be prepared respectively by methods according to the following reaction formulas XVII to XXI.

[Reaction process formula-XVII]

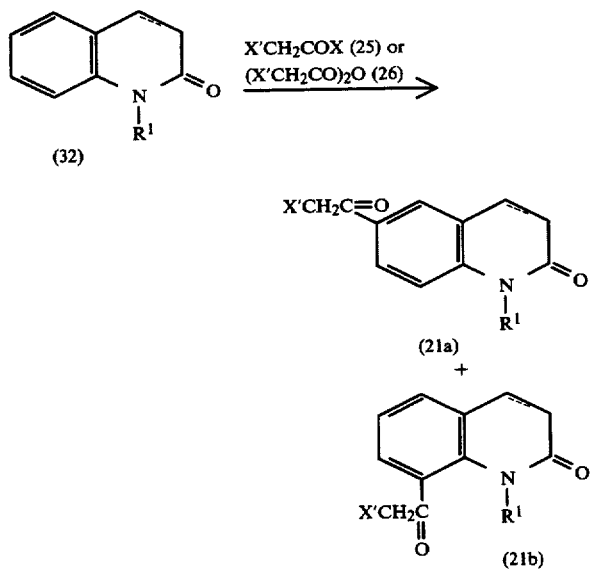

wherein $R^1$, X, X' and the carbon-carbon bond between 3- and 4-positions in the carbostyril skeleton are the same as defined above.

The reaction of the compound (32) with the compound (25) or (26) can be carried out under the conditions similar to those shown in the reaction of the compound (24) with the compound (25) or (26) in the reaction process formula-XV. The reaction is generally carried out at 20° C., preferably at 40° to 70° C., and the reaction time is generally in 30 minutes to 24 hours depend on the type of the starting materials and the type of the catalyst.

[Reaction process formula-XVIII]

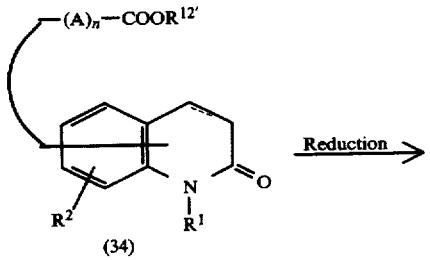

-continued

[Reaction process formula-XVIII]

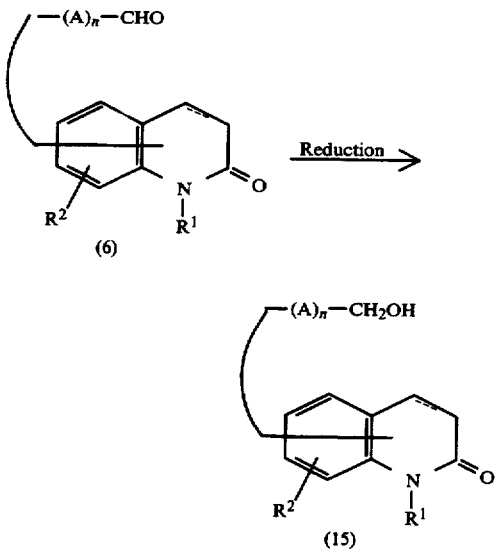

wherein $R^1$, $R^2$, A, n and the carbon-carbon bond between 3- and 4-positions in the carbonstyril skeleton are the same as defined above; and $R^{12'}$ is a hydrogen stom, a lower alkyl group or a group of the formula

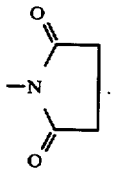

The reaction for obtaining the compound (6) by reducing the compound (34) is carried out under conditions similar to those employed in the reaction for obtaining the compound (15) by reducing the compound (12) in the reaction process formula-XI, and similar to those employed in the reaction for obtaining the compound (1'') by catalytically reducing the compound (1') in the reaction process formula-III.

Various methods can be applied for reducing the compound (6) to obtain the compound (15), for example a reducing method by using hydrogenation reducing agent can preferably be applied. As to the hydrogenation reducing agents, the examples include sodium aluminium hydride, lithium aluminum tri-tert-butoxyaluminium hydride, diisobutylaluminium hydride, (1,1-dimethyl-1-diisopropylmethyl)boron hydride and sodium borohydride.

The amount of the hydrogenation reducing agent is generally an equivalent amount by weight to the amount of the compound (6). The reducing reaction is carried out in a suitable solvent for example diethyl ether, tetrahydrofuran or diglyme, at −60° to 50° C., preferably at −30° to a room temperature. The reaction is completed in 10 minutes to 5 hours.

[Reaction process formula-XIX]

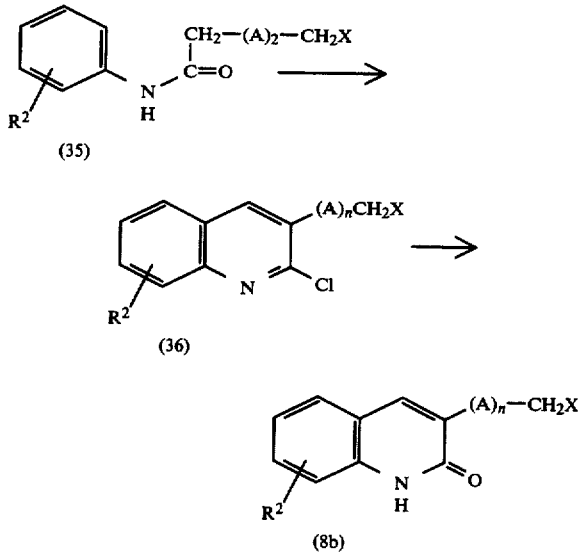

wherein $R^2$, A, n and X are the same as defined above.

The cyclization reaction of the compound (35) is carried out under conditions similar to those employed in the cyclization reaction of the compound (10) shown in the reaction process formula-X. Further, the reaction for obtaining the compound (8b) from the compound (36) is carried out under conditions similar to those employed in the reaction for obtaining the compound (6a) from the compound (11) in the reaction process formula-X.

[Reaction process formula-XX]

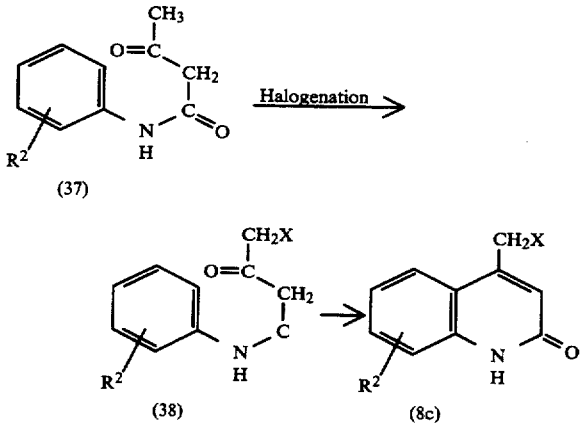

wherein $R^2$ and X are the same as defined above.

In the above-mentioned reaction process formula, the halogenation reaction of the compound (37) is carried out in a suitable solvent by treating the compound (37) with a halogenating agent. As to the halogenating agent used, examples include halogen molecules such as chlorine and bromine; N-halogenosuccinimides, such as N-chlorosuccinimide and N-bromosuccinimide; sulfuryl chloride; copper halogenides such as copper chloride and copper bromide. As to the solvent used, examples include halogenated hydrocarbons such as dichloromethane, dichloroethane, chloroform, and carbon tetrachloride; ethers such as diethyl ether, tetrahydrofuran and dioxane; and acetic acid.

The ratio of the amount of the halogenating agent to the amount of the compound (37) is an equimolar quantity to a large excess amount, preferably an equimolar quantity to 1.2 times the molar quantity of the former. The reaction is generally carried out at 0° C. to about the boiling point of the solvent, preferably at a room temperature to 40° C. The reaction is generally completed in 1 to 10 hours. The reaction may be carried out by using a peroxide such as benzoyl peroxide or hydrogen peroxide as the reaction initiator.

The reaction for obtaining the compound (8c) by cyclizing the compound (38) can be carried out in a suitable solvent, in the presence of a condensing agent.

As to the condensing agent used, the examples include Lewis acids such as phosphorus pentoxide, hydrogen fluoride, sulfuric acid, polyphosphoric acids, aluminium chloride and zinc chloride. As to the solvent used, the examples include halogenated hydrocarbons such as chloroform, dichloromethane and 1,2-dichloroethane; ethers such as diethyl ether and dioxane; aromatic hydrocarbons such as nitrobenzene and chlorobenzene. The ratio of the amount of the compound (38) to the amount of the condensing agent is not specifically restricted, and generally an equimolar quantity to 10 times the molar quantity, preferably 3 to 6 times the molar quantity of the latter may be used to the former. The reaction is generally carried out at 50° to 250° C., preferably at 70° to 200° C., for 20 minutes to about 6 hours.

[Reaction process formula-XXI]

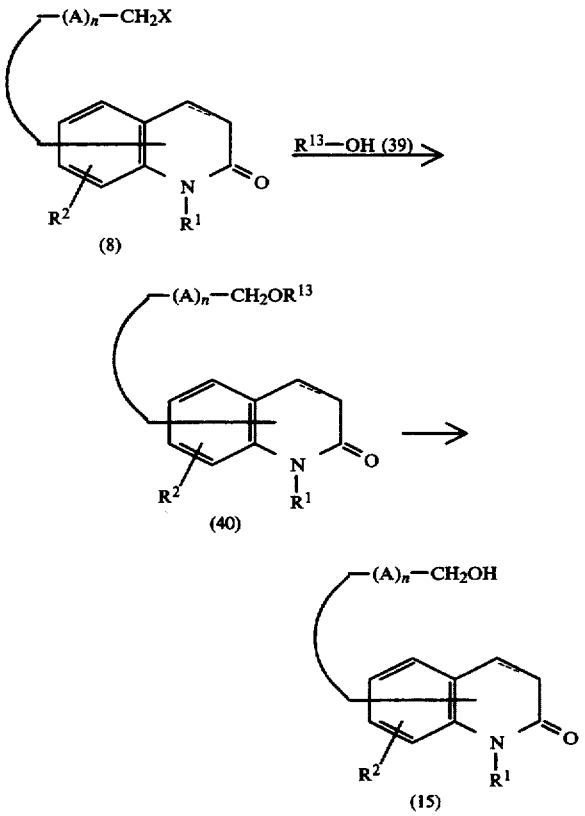

wherein $R^1$, $R^2$, X and the carbon-carbon bond between 3- and 4-positions in the carbostyril skeleton are the same as defined above; and $R^{13}$ is a lower alkanoyl group.

In the above-mentioned reaction process formula, the reaction of the compound (8) with the compound (39) is preferably carried out by using a basic compound as the dehydrohalogenating agent, in a suitable solvent, at a room temperature to 200° C., preferably at a room temperature to 150° C., for a several hours to 15 hours. As to the solvent used, examples include lower alcohols such as methanol, ethanol and isopropanol; ethers such as diethyl ether, tetrahydrofuran, dioxane, ethylene glycol monomethyl ether and diethylene glycol dimethyl ether; aromatic hydrocarbons such as benzene, toluene and xylene; ketones such as acetone and methyl ethyl ketone; polar solvents such as dimethylformamide, dimethyl sulfoxide, hexamethylphosphoryl triamide and acetic anhydride. As to the basic compounds used, examples include inorganic basic compounds such as sodium hydroxide, potassium hydroxide, sodium carbonate, potassium carbonate, sodium hydrogencarbonate, potassium hydrogencarbonate, and silver carbonate; alkali metals such as sodium and potassium; sodium amide; sodium hydride; alkali metal alcoholates such as sodium methylate, sodium ethylate and potassium ethylate; tertiary amines such as triethylamine, tripropylamine, pyridine, quinoline, N,N-dimethylaniline and N-methylmorpholine. In the above-mentioned reaction, an alkali metal iodide such as potassium iodide or sodium iodide may be used as the reaction accelerator.

The ratio of the amount of the compound (8) to the amount of the compound (39) is not specifically restricted, and generally at least an equimolar quantity, preferably 1 to 5 times the molar quantity of the latter is used to the former.

The compound (40) thus obtained is hydrolyzed to obtain the compound (15). Said hydrolyzing reaction is carried out in the presence of a hydrohalogenic acid such as hydrochloric acid or hydrobromic acid; a mineral acid such as sulfuric acid or phosphoric acid; an alkali metal hydroxide such as sodium hydroxide, alkali metal carbonate such as sodium carbonate or potassium carbonate; an alkali metal hydrogencarbonate such as sodium hydrogencarbonate, generally at 50° to 150° C., preferably at 70° to 100° C., for 3 to 24 hours under heating condition.

The compounds (15) and (8) can also converted into other types of the compounds of the formulas (15) and (8) by methods according to the N-alkylating process as shown in the reaction process formula-V and -VIII, and to the dehydrogenating process and the reducing process as shown in the reaction process formulas-VI and IX.

The compound of the general formula (12) in the reaction process formula-XI can also be prepared by a method, for example, the following reaction process formula-XXII.

[Reaction process formula-XXII]

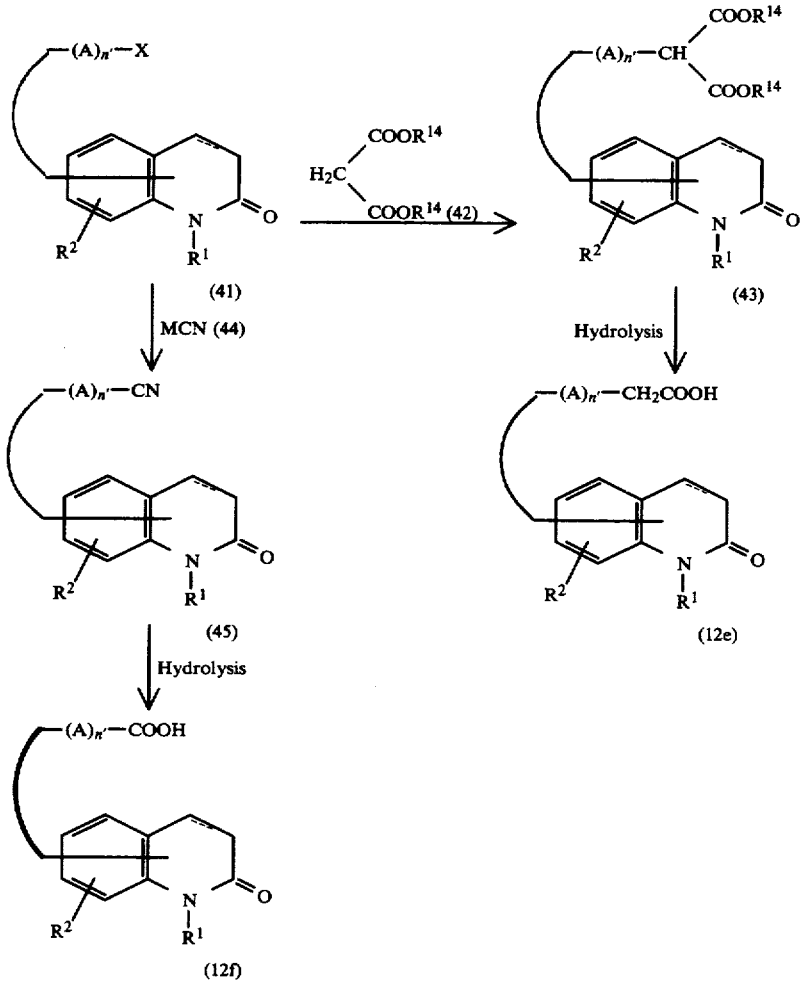

wherein $R^1$, $R^2$, A, X and the carbon-carbon bond between 3- and 4-positions in the carbostyril skeleton are the same as defined above; $R^{14}$ is a lower alkyl group; n' is 1.

The reaction of the compound of the general formula (41) with the compound of the general formula (42) can be carried out under conditions similar to those employed in the reaction of the compound of the general formula (8) with the compound of the general formula (9).

The hydrolysis of the compound of the general formula (43) can be carries out under conditions similar to those employed in the hydrolysis of the compound of the general formula (2).

The reaction of the compound of the general formula (41) with a metal cyanide of the general formula (44) is carried out in a suitable solvent. As to the metal cyanide of the general formula (44), examples include potassium cyanide, sodium cyanide, silver cyanide, copper cyanide and calcium cyanide. As to the solvent used, examples include water; lower alcohols such as methanol, ethanol and isopropanol; and mixed solvent of water with these alcohols. The amount of metal cyanide of the general formula (44) used is at least an equimolar quantity, preferably 1 to 1.5 times the molar quantity to the amount of the compound of the general formula (41). The reaction is generally carried out at a room temperature to 150° C., preferably at around 50° to 120° C., for 30 minutes to 10 hours.

The hydrolysis of the compound of the general formula (45) can be carried out under conditions similar to those employed in the hydrolysis of the compound of the general formula (2).

The compound of the carbostyril derivatives of the present invention can also be prepared by a method as shown in the following reaction process formula-XXIII.

[Reaction process formula-XXIII]

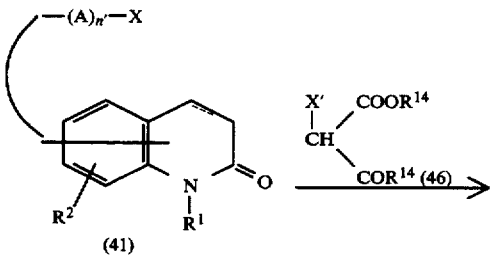

-continued

[Reaction process formula-XXIII]

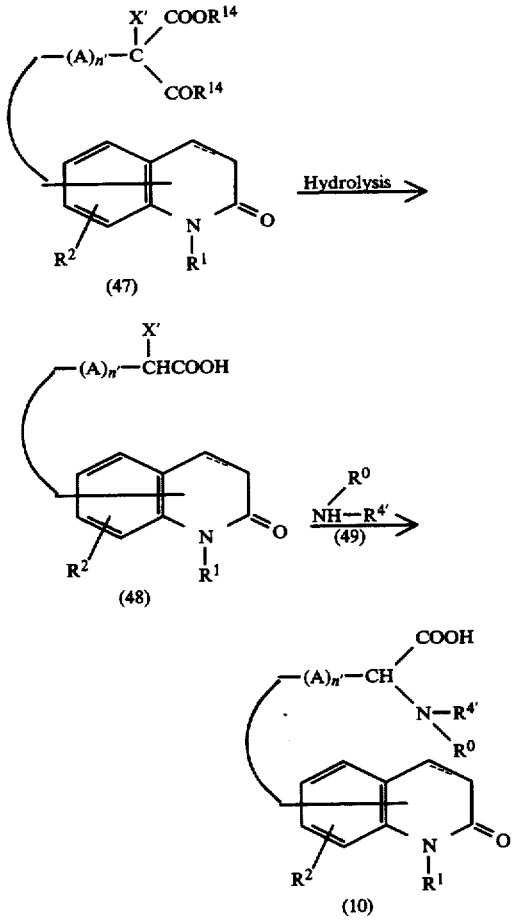

wherein $R^o$, $R^1$, $R^2$, $R^{4'}$, $R^{14}$, A, n', X' and the carbon-carbon bond between 3- and 4-positions in the carboxtyril skeleton are the same as defined above.

The reaction of the compound of the general formula (41) with the compound of the general formula (46) can be carried out under conditions similar to those employed in the reaction of the compound of the general formula (8) with the compound of the general formula (9).

The hydrolysis of the compound of the general formula (47) can be carried out under conditions similar to those employed in the hydrolysis of the compound of the general formula (2).

The reaction of the compound of the general formula (48) with the compound of the general formula (49) can be carried out in the absence or presence of a suitable solvent, in the presence of a basic compound. As to the solvent used, examples include ethers such as dioxane, tetrahydrofuran, ethylene glycol dimethyl ether and diethyl ether; aromatic hydrocarbons such as benzene, toluene and xylene; lower alcohols such as methanol, ethanol and isopropanol; polar solvents such as dimethyl sulfoxide, dimethylformamide, hexamethylphosphoryl triamide and acetone. As to the basic compounds used, examples include inorganic basic compounds such as potassium carbonate, sodium carbonate, potassium hydrogencarbonate, sodium hydrogencarbonate, potassium hydroxide, sodium hydroxide, sodium amide and sodium hydride; organic basic compounds such as triethylamine, tripropylamine, pyridine and quinoline.

The reaction is carried out generally at a room temperature to 200° C., preferably at a room temperature to 150° C., for 1 to 30 hours.

The reaction can advantageously be proceeded by adding an alkali metal iodide such as potassium iodide or sodium iodide; or hexamethylphosphoryl triamide as the reaction accelerator.

The amount of the compound of the general formula (49) used may be generally an equimolar to a large excess quantity, preferably an equimolar to 5 times the molar quantity to the amount of the compound of the general formula (48).

By carrying out carbon number increasing reactions in the above-mentioned reaction process formula-XI [(12) or (14)→(15)→(8)] and the reaction process formula-XXII [(41)→(43)→(12e) or (41)→(45)→(12f)] repeatedly in several times, the desired carbostyril derivative represented by the general formula

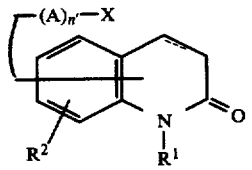

(41)

wherein $R^1$, $R^2$, A, n', X and the carbon-carbon bond between 3- and 4-positions in the carbostyril skeleton are the same as defined above, having the predetermined number of carbon atoms can be prepared.

Carbostyril derivatives of the present invention are useful as anti-peptic ulcer agents, and they can be used as in the form of general preparations of pharmaceutical compositions together with usual pharmaceutically acceptable carriers. Examples of the pharmaceutically acceptable carriers which are used depending on the desired form of pharmaceutical compositions including diluents or excipients such as fillers, diluents, binders, wettable agents, disintegrators, surface-active agents and lubricants.

No particular restriction is made to the administration unit forms and the compositions can be selected from any desired unit form including tablets, pills, powders, liquors, suspensions, emulsions, granules, capsules, suppositories and injections (solutions, suspensions and the like).

For the purpose of to shape in the form of tablets, carriers which are widely used in the field can also be used, for example excipients such as lactose, sucrose, sodium chloride, glucose, urea, starch, calcium carbonate, caolin, crystalline cellulose, silicic acid and the like; binding agents such as water, ethanol, propanol, simple syrus, glucose solution, starch solution, gelatin solution, carboxymethyl cellulose, shelac, methyl cellulose, calcium phosphate and polyvinylpyrrolidone; desintegrators such as dried starch, sodium alginate, agar-agar powder, laminalia powder, sodium hydrogencarbonate, calcium carbonate, esters of polyoxyethylene sorbitan fatty acids, sodium laurylsulfate, monoglyceride of stearic acid, starch and lactose; desintegration inhibitors such as sucrose, stearin, coconut butter and hydrogenated oils; absorption accelerators such as quaternary ammonium bases and sodium laurylsulfate; wetting agents such as glycerin and starch; absorbing agents such as starch, lactose, kaolin, bentonite and colloidal silicic acid; and lubricants such as purified talc, stearic acid salts, boric acid powder and polyethylene glycols.

In case of preparing tablets, they can be further coated with usual coating materials to make them into tablets coated with sugar, tablets coated with gelatin film, tablets coated with enteric coatings, tablets coated with films or double layer tablets as well as multiple layer tablets.

For the purpose of to shape in the form of pills, any carrier which is known and used widely in this field can be used, for example, excipients such as glucose, lactose, starch, coconut butter, hydrogenated vegetable oils, kaolin and talc; binders such as powdered gum arabi, powdered tragacanth gum, gelatin and ethanol; desintegrators such as laminaria and agar-agar are included.

For the purpose of to shape in the form suppositories, carriers which are known and widely used in this field can also be used, for example, polyethylene glycols, coconut butter, higher alcohols, esters of higher alcohols, gelatin semi-synthesized glycerides are included.

For the purpose of to make in the form of injection preparations, solutions and suspensions are sterilized and are preferably isotonic to the blood. In making injection preparations in the form of solutions, emulsions and suspensions, any carrier which is known and is widely used in this field can also be used, for example water, ethyl alcohol, propylene glycol, ethoxylated isostearyl alcohol, polyoxylated isostearyl alcohol and polyoxyethylene sorbitan fatty acid esters are included. In these instances, adequate amounts of sodium chloride, glucose or glycerin can be added to the desired injection preparations to make them isotonic. Furthermore, usual dissolving agents, buffers, analgesic agents can be added, further coloring materials, preservatives, perfumes, seasoning agents, sweetening agents and other medicines can also be added into the desired preparations, if necessary.

The amount of carbostyril derivatives of the present invention to be contained in the anti-peptic ulcer composition of the present invention is not specifically restricted and it can suitably be selected from wide range, and generally 1 to 70%, preferably 5 to 50% by weight of the whole composition.

Anti-peptic ulcer agent of the present invention can be used in various forms of preparations depending on the agen, the distinction of sex, the degree of symptoms and other conditions without any restriction. For example, tablets, pills, solutions, suspensions, emulsions, granules and capsules are administered orally; injection preparations are administered intravenously singly or administered mixed with usual injection transfusions such as glucose solutions and amino acid solutions; if necessary, the injection preparations are administered singley intramuscularly, intracutaneously, subcutaneously or intraperitoneally; suppositories are administered into rectum.

The dosage of the present anti-peptic ulcer agent can be selected suitably according to the usages, the age of the patiant, the distinct of sex and other conditions as well as the degree of the symptoms, and generally pharmaceutical compositions containing 0.6 to 50 mg/kg of body weight/day of the carbostyril derivative of the general formula (1) or its salt. Further the active ingredient may be contained 10 to 1,000 mg in the administrative unit form.

The present invention will be explained more in specifically by way of the following examples, in which the preparation of the compounds to be used for the starting materials will be shown as Reference Examples and the preparation of the objective compounds will be shown as Examples.

REFERENCE EXAMPLE 1

100 Grams of m-aminobenzoic acid was suspended in 1 liter of ether, then 44.6 g of β-ethoxyacrylyl chloride was added dropwise into the solution at a room temperature under stirring condition. This reaction mixture was kept at 40° C. for 5 hours, then the precipitate formed in the reaction mixture was collected by filtration. The crystals were washed with water three times, dried and recrystallized from methanol to obtain 60 g of m-carboxy-N-(β-ethoxyacryloyl)aniline in the form of colorless cotton-like crystals.

Melting point: 200.5°–220.0° C.

REFERENCE EXAMPLE 2

A mixture of 50 g of methyl 3-phenylpropionate, 51.6 g of chloroacetyl chloride and 250 ml of dichloromethane was cooled to 0° C. The mixture was stirred at 0° to 10° C. and 122 g of aluminum chloride was added gradually into the mixture. The reaction mixture was then stirred at a room temperature for 2 hours. The reaction mixture was allowed to stand overnight, then the reaction mixture was poured into a mixture of ice-concentrated hydrochloric acid and was extracted with chloroform. The chloroform layer was washed with water, dried then chloroform was removed from the reaction mixture by distillation. The residue thus obtained was crystallized by adding isopropyl ether, and the crystals formed were collected by filtration, then recrystallized from ethanol to obtain 53.4 g of methyl 3-(4-chloroacetylphenyl)propionate in the form of needle-like crystals.

Melting point: 90.0°–92.0° C.

REFERENCE EXAMPLE 3

36.26 Grams of methyl 3-(4-chloroacetylphenyl)propionate was dissolved in 300 ml of concentrated sulfuric acid, then 20.9 g of fuming nitric acid (d=1.52) was added dropwise thereto under an ice-cooled condition with stirring. The reaction mixture was further stirred at a room temperature for 3 hours, then was poured into ice-water, and extracted with chloroform. The chloroform layer was washed with water, dried and chloroform was removed by distillation. The residue thus obtained was purified by a silica gel column chromatography, then crystallized by adding ether. The crystals formed were collected by filtration, recrystallized from methanol to obtain 26.7 g of methyl 3-(4-carboxy-2-nitrophenyl)propionate in the form of light yellowish prism-like crystals.

Melting point: 120.0°–122.0° C.

REFERENCE EXAMPLE 4

To a solution containing 467 g of chloroacetyl chloride in 400 ml of dichloromethan, 735 g of aluminium chloride was added by 1/3 each at a temperature below 30° C. with stirring condition. Next 200 g of carbostyril was added thereto at the same temperature under stirring condition. The reaction mixture was refluxed for 6 hours, then the reaction mixture was poured into a mixture of ice-concentrated hydrochloric acid and the crystals formed were collected by filtration. The crystals were washed with methanol, then with hot-methanol to obtain 153 g of 6-chloroacetylcarbostyril. The mother liquor was concentrated to dryness, and the residue obtained was purified by a silica gel column chromatography, then recrystallized from methanol to obtain 35.41 g of 8-chloroacetylcarbostyril in the form of light yellow crystals.

Melting point: 177.5°-179.0° C.

REFERENCE EXAMPLE 5

30 Grams of 8-chloroacetylcarbostyril was mixed with 300 ml of pyridine and this mixture was heated at 80°-90° C. for 2.5 hours with stirring condition. The reaction mixture was ice-cooled and the crystals thus precipitated were collected by filtration, washed with ether and recrystallized from methanol to obtain 40.85 g of 8-(α-pyridiniumacetyl)carbostyril. chloride in the form of colorless needle-like crystals.

Melting point: 261.5°-264.0° C. (decomp.)

REFERENCE EXAMPLE 6

To a solution containing 29.5 g of methyl m-aminobenzoate in 300 ml of diethyl ether, 11.53 g of β-ethoxyacrylic acid chloride was added dropwise at 17°-27° C. under stirring condition. After the addition was finished, the reaction mixture was further stirred at a room temperature for 1 hour, then the crystals thus precipitated were collected by filtration. The crystals were washed with ether, and the crude crystals were dissolved in chloroform, then the chloroform solution was washed with 0.5N-hydrochloric acid, a saturated aqueous solution of sodium hydrogencarbonate and a saturated aqueous solution of sodium chloride. The chloroform solution was dried and then chloroform was removed by distillation, and the residue thus obtained was purified by a silica gel column chromatography, then recrystallized from methanol to obtain 13.63 g of m-methoxycarbonyl-N-(β-ethoxyacryloyl)aniline in the form of colorless prism-like crystals.

Melting point: 108°-110° C.

REFERENCE EXAMPLE 7

(a) 60 Grams of 6-(α-chloroacetyl)carbostyril was suspended in 0.5 kg of pyridine, then this suspension was stirred at a temperature of 80°-90° C. for 2 hours, and further stirred under ice-cooled condition for 1 hour. The crystals thus precipitated were collected by filtration, recrystallized from methanol to obtain 70 g of 6-(α-pyridinium)carbostyril chloride semihydrate in the form of colorless needle-like crystals.

Melting point: Over 300° C.

(b) 69.7 Grams of 6-(α-pyridiniumacetyl)carbostyril chloride and 65 g of sodium hydroxide were dissolved in 0.6 liter of water, and this solution was stirred at 60°-70° C. for 3 hours. Then the pH of reaction mixture was adjusted to about pH 2 by adding a concentrated hydrochloric acid. The crystals thus precipitate were collected by filtration, and recrystallized from dimethylformamide to obtain 41.4 g of 6-carboxycarbostyril in the form of light brownish powdery product.

Melting point: Over 300° C.

REFERENCE EXAMPLE 8

By a method similar to that described in Reference Example 7, by using a suitable starting material, the following compound was obtained.

6-Carboxy-3,4-dihydrocarbostyril

Light yellowish powdery product (from dimethylformamide).

Melting point: Over 300° C.

8-Carboxycarbostyril

Colorless needle-like crystals (from methanol-chloroform).

Melting point: Over 320° C.

NMR (dimethylsulfoxide) 6.57 (d, J=9.5 Hz, 1H), 7.25 (t, J=8.0 Hz, 1H), 7.94 (d, d, J=8.0 Hz, 1.5 Hz, 1H), 7.98 (d, J=9.5 Hz, 1H), 8.14 (d, d, J=8.0 Hz, 1.5 Hz, 1H).

REFERENCE EXAMPLE 9

10 Grams of 6-carboxy-3,4-dihydrocarbostyril and 6.0 g of N-hydroxysuccinimide were suspended in 200 ml of dioxane. Then a solution containing 12.4 g of dicyclohexylcarbodiimide in 50 ml of dioxane was added dropwise thereto under ice-cooled condition with stirring. The reaction mixture was further stirred for 4 hours at 90° C. After the reaction was completed, the reaction mixture was allowed to stand to cool at room temperature, and the crystals precipitated were removed by filtration, then the filtrate obtained was concentrated to dryness. The residue was recrystallized from dimethylformamide-ethanol to obtain 10.8 g of succinimide 3,4-dihydrocarbostyril-6-carboxylate in the form of colorless flake-like crystals.

Melting point: 234.5°-236° C.

REFERENCE EXAMPLE 10

8 Grams of m-carboxy-N-(β-ethoxyacryloyl)aniline was added to 80 ml of concentrated sulfuric acid, the mixture was stirred at a room temperature for 2 hours, then at 50° C. for 1 hour. The reaction mixture was poured into ice-water and the pH of the resultant mixture was adjusted to pH 3-4 by using 10N-sodium hydroxide aqueous solution. The crystals precipitated were collected by filtration and recrystallized from dimethylformamide to contain 4.26 g of 5-carboxycarbostyril in the form of light yellowish powdery product.

Melting point: Over 320° C.

NMR (DMSO) 6.58 (d, J=9.5 Hz, 1H), 7.40-7.80 (m, 3H), 8.69 (d, J=9.5 Hz, 1H).

REFERENCE EXAMPLE 11

5 Grams of methyl 3-(4-carboxy-2nitrophenyl)propionate, 8.87 ml of 2.226N-sodium hydroxide methanol solution, 100 ml of methanol and 1 g of 5%-Pd-C (50% in water) were well mixed together and this mixture was catalytically reduced at a normal temperature under a normal pressure. Then the catalyst was removed from the reaction mixture by filtration, and the pH of the filtrate was adjusted to about pH=1 by adding concentrated hydrochloric acid. The precipitated crystals were collected by filtration and recrystallized from methanol to obtain 3.62 g of 7-carboxy-3,4-dihydrocarbostyril in the form of colorless needle-like crystals.

Melting point: Over 320° C.

NMR (DMSO) 2.33-2.60 (m, 2H), 2.77-3.05 (m, 2H), 7.21 (d, J=9.5 Hz, 1H), 7.38-7.53 (m, 2H), 10.15 (s, 1H).

REFERENCE EXAMPLE 12

10 Grams of m-methoxycarbonyl-N-(β-ethoxyacryloyl)aniline was added to 100 ml of concentrated sulfuric acid gradually, and this mixture was stirred at a room temperature for 2 hours, then at 45° C. for 4 hours. The reaction mixture was poured in ice-water, and the precipitated crystals were collected by filtration and were washed with water. Thus obtained crude crystals were recrystallized from methanol-chloroform to obtain 6.97 g of 5-methoxycarbonylcarbostyril.

Melting point: 277.5°–279.0° C.

REFERENCE EXAMPLE 13

2 Grams of 5-carboxycarbostyril was suspended in 30 ml of water, then 10N-sodium hydroxide aqueous solution was added to dissolve the crystals. To this solution was added 500 mg of 10% platinum-carbon and this mixture was catalytically reduced with hydrogen gas under condition of 3–4 kg/cm$^2$ at 70° C. After the completion of the reaction, the catalyst was removed from the reaction mixture by filtration, then the pH of the filtrate was adjusted to about pH = 1 by adding concentrated hydrochloric acid. The precipitated crystals were collected by filtration, recrystallized from methanol to obtain 820 mg of 5-carboxy-3,4-dihydrocarbostyril in the form of colorless needle-like crystals.

Melting point: 309°–311° C.

REFERENCE EXAMPLE 14

2 Grams of 5-carboxycarbostyril was suspended in 100 ml of methanol, and hydrogen chloride gas was saturated by bubbling into this suspension, then the reaction mixture was refluxed for 3 hours. The reaction mixture was concentrated to be reduced one-half volume of its initial value, and the precipitated crystals were collected by filtration. The crystals were purified by a silica gel column chromatography, and recrystallized from methanol-chloroform to obtain 230 mg of 5-methoxycarbonylcarbostyril in the form of colorless powdery product.

Melting point: 277.5°–279° C.

REFERENCE EXAMPLE 15

2 Grams of 8-(α-pyridiniumacetyl)carbostyril chloride was dissolved in 20 ml of methanol, and 1.01 g of DBU (1,5-diazabicyclo[5,4,0]undecane-5) and refluxed for 1 hour. The reaction mixture was concentrated to dryness and to the residue was added water, chloroform and 1N-hydrochloric acid. The chloroform layer was washed with water, a saturated sodium hydrogencarbonate aqueous solution and a saturated sodium chloride aqueous solution in this order, and dried. Chloroform was removed by distillation, the residue thus obtained was purified by a silica gel column chromatography, then recrystallized from methanol to obtain 130 mg of 8-methoxycarbonylcarbostyril in the form of colorless needle-like crystals.

Melting point: 140°–142° C.

REFERENCE EXAMPLE 16

34 Grams of 3-formylcarbostyril was suspended in 800 ml of methanol, and 7.4 g of sodium borohydride was added gradually thereto under ice-cooled condition with stirring. The reaction mixture was further stirred under ice-cooling for 3 hours. The precipitated crystals were collected by filtration and recrystallized from methanol to obtain 33.2 g of 3-hydroxymethylcarbostyril in the form of colorless prism-like crystals.

Melting point: 238°–239.5° C.

REFERENCE EXAMPLE 17

16 Grams of lithium aluminum hydride was suspended in 200 ml of dried tetrahydrofuran, then 16 g of 3-methoxycarbonylcarbostyril was added thereto at a room temperature with stirring. The reaction mixture was further stirred for 5 hours at a room temperature. The excess lithium aluminum hydride in the reaction mixture was decomposed by adding ethyl acetated dropwise. Further, water was added to the reaction mixture and concentrated under a reduced pressure to obtain residue. To the residue was added a diluted sulfuric acid and the precipitated crystals were collected by filtration and recrystallized from methanol to obtain 3.7 g of 3-hydroxymethylcarbostyril in the form of colorless prism-like crystals.

Melting point: 238°–239.5° C.

REFERENCE EXAMPLES 18–23

By a method similar to that described in Reference Examples 16 and 17, by using a suitable starting material, there were prepared compounds as shown in Table 1 as follows.

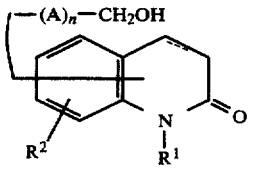

TABLE 1

| Reference Example | R$^1$ | R$^2$ | Substituted position of the side-chain of —(A)$_n$—CH$_2$OH | Carbon-carbon bond between 3- and 4-position | Crystal form | Solvent | Melting point (°C.) | (A)$_n$ |
|---|---|---|---|---|---|---|---|---|
| 18 | H | 6-OCH$_3$ | 3 | Double bond | Light yellowish needle-like crystals | Acetone | 196–197 | — |
| 19 | H | H | 3 | Single bond | Colorless prism-like crystals | Ehtyl acetate-hexane | 104.5–105.5 | — |
| 20 | H | H | 4 | Double bond | Colorless needle-like crystals | Methanol-chloroform | 272–274.5 | — |
| 21 | H | H | 6 | Single bond | Colorless needle-like crystals | Acetone | 175.5–177.5 | — |
| 22 | H | H | 4 | Single bond | Colorless needle-like crystals | Ether | 221.5–222.5 | — |
| 23 | H | H | 4 | Double bond | Light brownish prism-like | Ethanol | 170–171.5 | —CH$_2$CH$_2$— |

TABLE 1-continued

| Reference Example | $R^1$ | $R^2$ | Substituted position of the side-chain of $-(A)_n-CH_2OH$ | Carbon-carbon bond between 3- and 4-position | Crystal form | Solvent | Melting point (°C.) | $(A)_n$ |
|---|---|---|---|---|---|---|---|---|
| | | | | | crystals | | | |

REFERENCE EXAMPLE 24

To 5 g of 3-hydroxymethylcarbostyril was added 50 ml of 47%-hydrobromic acid and the mixture was stirred at 70°–80° C. for 3 hours. After cooled the reaction mixture, the crystals precipitated were collected by filtration and were recrystallized from methanol to obtain 6 g of 3-bromomethylcarbostyril in the form of colorless needle-like crystals.

Melting point: 218.5°–219° C. (decomposed).

REFERENCE EXAMPLE 25

3 Grams of 3-hydroxymethylcarbostyril was suspended in 100 ml of chloroform, then a solution containing 2 g of thinyl chloride in 20 ml of chloroform was added dropwise thereto at a room temperature with stirring condition. The reaction mixture was further sitrred at a room temperature for 1 hour. The reaction mixture was concentrated under a reduced pressure, and the residue obtained was recrystallized from methanol to obtain 2.9 g of 3-chloromethylcarbostyril in the form of colorless needle-like crystals.

Melting point: 204°–205° C.

REFERENCE EXAMPLE 26

2.8 Grams of 2-chloro-3-chloromethylquinoline was dissolved in 30 ml of acetic acid and the solution was refluxed for 2 hours. The reaction mixture was poured into water and the crystals precipitated were collected by filtration, and were recrystallized from methanol to obtain 2.1 g of 3-chloromethylcarbostyril in the form of colorless needle-like crystals.

Melting point: 204°–205° C.

REFERENCE EXAMPLES 27–40

By a method similar to that described in Reference Examples 24–26, by using a suitable starting material, there were prepared compounds as shown in Table 2 as follows.

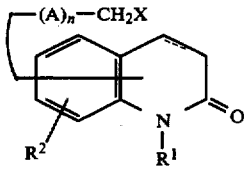

TABLE 2

| Reference Example | $R^1$ | $R^2$ | X | Substituted position of the side-chain of $-(A)_n-CH_2X$ | Carbon-carbon bond between 3- and 4-position | Crystal form | Recrystallization solvent | Melting point (°C.) | $(A)_n$ |
|---|---|---|---|---|---|---|---|---|---|
| 27 | H | 6-$OCH_3$ | Br | 3 | Double bond | Light yellowish needle-like crystals | Acetone | 212–212.5 | — |
| 28 | H | H | Br | 3 | Single bond | Colorless needle-like crystals | Ethyl acetate-hexane | 138–140.5 | — |
| 29 | H | H | Cl | 4 | Double bond | Colorless needle-like crystals | Methanol-chloroform | 252–254 | — |
| 30 | H | H | Br | 4 | Double bond | Colorless needle-like crystals | Methanol-chloroform | 265–266 | — |
| 31 | H | H | Br | 6 | Single bond | Colorless needle-like crystals | Acetone | 190–191 (decomp.) | — |
| 32 | $C_2H_5$ | H | Br | 4 | Double bond | Brownish needle-like crystals | Ethanol | 127–130 | — |
| 33 | H | 6-$OCH_3$ | Br | 4 | Double bond | Yellowish needle-like crystals | Ethanol | 284–250.5 (decomp.) | — |
| 34 | H | 8-Cl | Br | 4 | Double bond | Brownish needle-like crystals | Ethanol-chloroform | 206–208 | — |
| 35 | H | 8-$C_2H_5$ | Br | 4 | Double bond | Brownish powdery product | Dimethyl-formamide-water | 195–200 | — |
| 36 | H | H | Cl | 3 | Double bond | Colorless needle-like crystals | Ethanol | 165.5–166 | $CH_2$ |
| 37 | H | H | Cl | 4 | Double bond | Brownish prism-like crystals | Methanol | 186–187 | $CH_2$ |
| 38 | $CH_3$ | H | Br | 3 | Double bond | | | 95–100 | $CH_2$ |

TABLE 2-continued

| Reference Example | $R^1$ | $R^2$ | X | Substituted position of the side-chain of $-(A)_n-CH_2X$ | Carbon-carbon bond between 3- and 4-position | Crystal form | Recrystallization solvent | Melting point (°C.) | $(A)_n$ |
|---|---|---|---|---|---|---|---|---|---|
| 39 | H | H | Br | 4 | Double bond | Brownish needle-like crystals | Ethanol | 173–174 | $CH_2$ |
| 40 | H | H | Br | 4 | Double bond | Colorless needle-like crystals | Ethanol | 155–156 | $CH_2CH_5$ |

REFERENCE EXAMPLE 41

Sodium ethylate was prepared from 1.5 g of sodium metal and 150 ml of dried ethanol, then 12 g of diethyl acetamidemalonate was added thereto and the mixture was stirred at a room temperature for 1 hour. To this reaction mixture was added 12 g of 4-bromomethylcarbostyril, then the reaction mixture was refluxed for 2 hours. Ethanol was removed from the reaction mixture and to the residue thus obtained was added water to precipitate the crystals. The crystals were collected by filtration then were recrystallized from ethanol to obtain 13 g of ethyl 2-acetamido-2-carboethoxy-3-(2-quinolon-4-yl)propionate in the form of colorless prism-like crystals.

Melting point: 224°–226° C. (decomp.)

REFERENCE EXAMPLES 42–59

By a method similar to that described in Reference Esample 41, by using a suitable starting material, there were prepared compounds as shown in Table 3 as follows.

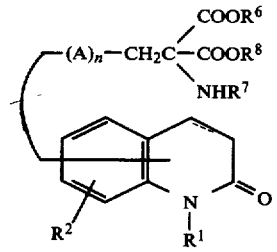

TABLE 3

| Reference Example | $R^1$ | $R^2$ | $R^6$ | $R^7$ | $R^8$ | Substituted position of the side-chain of the formula $-(A)_n-CH_2C(COOR^6)(COOR^8)(NHR^7)$ | Carbon-carbon bond between 3- and 4-positions | $(A)_n$ |
|---|---|---|---|---|---|---|---|---|
| 42 | H | H | $C_2H_5$ | $COCH_3$ | $C_2H_5$ | 3 | Double bond | — |
| 43 | $CH_3$ | H | $C_2H_5$ | $COCH_3$ | $C_2H_5$ | 3 | Double bond | — |
| 44 | H | 6-$OCH_3$ | $C_2H_5$ | $COCH_3$ | $C_2H_5$ | 3 | Double bond | — |
| 45 | $CH_3$ | H | $C_2H_5$ | $COCH_3$ | $C_2H_5$ | 4 | Double bond | — |
| 46 | $C_2H_5$ | H | $C_2H_5$ | $COCH_3$ | $C_2H_5$ | 4 | Double bond | — |
| 47 | $-CH_2CH=CH_2$ | H | $C_2H_5$ | $COCH_3$ | $C_2H_5$ | 4 | Double bond | — |
| 48 | $-CH_2C\equiv CH$ | H | $C_2H_5$ | $COCH_3$ | $C_2H_5$ | 4 | Double bond | — |
| 49 | 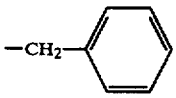 | H | $C_2H_5$ | $COCH_3$ | $C_2H_5$ | 4 | Double bond | — |
| 50 | H | H | $C_2H_5$ | $COCH_3$ | $C_2H_5$ | 5 | Double bond | — |
| 51 | H | H | $C_2H_5$ | $COCH_3$ | $C_2H_5$ | 6 | Single bond | — |
| 52 | $-C_2H_5$ | H | $C_2H_5$ | $COCH_3$ | $C_2H_5$ | 3 | Double bond | — |
| 53 | $-n-C_4H_9$ | H | $C_2H_5$ | $COCH_3$ | $C_2H_5$ | 4 | Double bond | — |
| 54 | H | 8-$CH_3$ | $C_2H_5$ | $COCH_3$ | $C_2H_5$ | 4 | Double bond | — |
| 55 | H | 8-Cl | $C_2H_5$ | $COCH_3$ | $C_2H_5$ | 4 | Double bond | — |
| 56 | H | 8-$C_2H_5$ | $C_2H_5$ | $COCH_3$ | $C_2H_5$ | 4 | Double bond | — |
| 57 | H | 6-$OCH_3$ | $C_2H_5$ | $COCH_3$ | $C_2H_5$ | 4 | Double bond | — |
| 58 | H | H | $C_2H_5$ | $COCH_3$ | $C_2H_5$ | 4 | Double bond | $CH_2CH_2$ |
| 59 | H | H | $C_2H_5$ | $COCH_3$ | $C_2H_5$ | 4 | Double bond | $CH_2$ |

| Reference Example | Crystal form | Recrystallization solvent | Melting point (°C.) | Salt |
|---|---|---|---|---|
| 42 | Colorless prism-like crystals | Ethanol | 228–230 (decomp.) | — |
| 43 | Colorless falke-like crystals | Ethanol | 190.5–192 | — |
| 44 | White powdery product | Ethyl acetate | 207–209 (decomp.) | — |
| 45 | Colorless needle-like | Ethanol | 191–192.5 | — |

TABLE 3-continued

| | | | | |
|---|---|---|---|---|
| | crystals | | | |
| 46 | Colorless needle-like crystals | Ethanol | 204–205 | — |
| 47 | Colorless prism-like crystals | Ethanol | 176–178.5 | — |
| 48 | White powdery product | Ethanol | 161–163 | — |
| 49 | White powdery product | Ethanol | 155–157 | — |
| 50 | Colorless granular crystals | Ethanol | 210–213 (decomp.) | $\frac{1}{2}H_2O$ |
| 51 | Colorless powdery product | Ethanol | 264–265 (decomp.) | — |
| 52 | Colorless needle-like crystals | Ligroin-ethanol | 153–154 | — |
| 53 | Colorless prism-like crystals | Ligroin | 107–110 | — |
| 54 | Colorless prism-like crystals | Ethanol | 211.5–212.5 | — |
| 55 | Colorless needle-like crystals | Ethanol | 188–190 | — |
| 56 | Colorless prism-like crystals | Ethanol | 192.5–195 | — |
| 57 | Colorless prism-like crystals | Ethanol | 207–208.5 | — |
| 58 | Colorless prism-like crystals | Ethanol | 156–158 | — |
| 59 | Colorless needle-like crystals | Ethanol-water | 182–183 | — |

REFERENCE EXAMPLE 60

5.6 Grams of ethyl 2-acetamido-2-carboethoxy-3-(2-quinolon-3-yl)propionate was dissolved in 150 ml of tetrahydrofuran, then 0.8 g of 50%-oily sodium hydride was added thereto at a room temperature with stirring. Next, 4.5 g of methyl iodide was added dropwise to the reaction mixture at a room temperature and stirred for 3 hours. After the completion of the reaction, the reaction mixture was concentrated under a reduced pressure, and the residue was poured into water, and the crystals precipitated were collected by filtration. Recrystallized from ethanol-water to obtain 3.5 g of ethy ethyl 2-acetamido-2-carboethoxy-3-(1-methyl-2-quinolon-3-61)propionate in the form of colorless flake-like crystals.

Melting point: 190.5°–192° C.

By a method similar to that described in Reference Example 60, there were prepared compounds of Reference Examples 46–49, 52, 53 and 58.

REFERENCE EXAMPLE 61

1.9 Grams of lithium aluminium hydride was suspended in 100 ml of dried tetraphydrofuran, then 1.9 g of 3-carbosycarbostyril was added at a room temperature with stirring, and further tha reaction mixture was stirred at a room temperature continuously for overnight. The excess of lithium aluminium hydride was decomposed by adding ethyl acetate dropwise. Then the reaction mixture was acidified by adding a diluted sulfuric acid. After removal of tetraphdrofuran by distillation under a reduced pressure, the crystals precipitated were collected by filtration. Recrystallized from methanol to obtain 0.5 g of 3-hydroxymethylcarbostyril in the form of colorless prism-like crystals.

Melting point: 238°–239.5° C.

By a method similar to that described in Reference Example 61, by using asuitable starting material, there were prepared compounds of Reference Example 18–23.

REFERENCE EXAMPLE 62

30 Grams of acetoacetanilide was dissolved in 30 ml of chloroform, then a solution containing 27 g of bromine in 30 ml of chloroform was added dropwise thereto at a room temperature with stirring. After completion of the addition of bromine, the reaction mixture was refluxed for 30 minutes. The reaction mixture was concentrated under a reduced pressure, the residue obtained was added to 70 ml of a concentrated sulfuric acid with stirring. The addition operation was conducted by keeping the inside of the vessel within 70°–75° C., then the whole mixture was poured into ice-water and the crystals precipitated were collected by filtration. Recrystallized from methanol-chloroform to obtain 20 g of 4-bromomethylcarbostyril in the form of colorless needel-like crystals.

Melting point: 265°–266° C.

By a method similar to that described in Reference Example 62, by using a suitable starting material, there were prepared compounds of Reference Examples 24, 25, 27–29 and 31–40.

REFERENCE EXAMPLE 63

2.2 Grams of 3-chloromethyl-6-methoxycarbostyril was dissolved in 20 ml of acetic anhydride, then 12 g of potassium acetate was added thereto and stirred at 60°–70° C. for 3 hours. The reaction mixture was poured in an ice-water and the crystals precipitated were collected by filtration. Recrystallized from acetone to obtain 2 g of 3-acetoxymethyl-6-methoxycarbostyril in the form of colorless prism-like crystals.

Melting point: 166°–168° C.

REFERENCE EXAMPLE 64

2 Grams of 3-acetoxymethylcarbostyril was dissolved in 30 ml of methanol containing 0.6 g of sodium hydroxide, then the mixture was refluxed for 3 hours. After removal of methanol by distillation, to the residue thus obtained was added water and the crystals precipitated were collected by filtration. Recrystallized from acetone to obtain 1.3 g of 3-hydroxymethyl-6-methoxycarbostyril in the form of light yellowish needle-like crystals.

Melting point: 196°–197° C.

By a method similar to that described in Reference Example 64, by using a suitable starting material, there were prepared compounds of 16, and 19–23.

REFERENCE EXAMPLE 65

(a) In a four-necked flask, there were placed 175 ml of water, 10.5 g of ferrous sulfate heptahydrate, 0.5 ml of concentrated hydrochloric acid and 6 g of o-nitrobenzaldehyde, then the flask was heated at 90° C. on a water-bath. Into the reaction mixture in the flask, 25 ml of a concentrated ammonia water was added in one-time with stirring, further 30 ml of ammonia water was added in three times in every 2 minutes. After finished the addition of ammonia water, the reaction mixture was subjected to steam distillation immediately. The distillate in an amount of 250 ml was collected in two times separately. The first distillate was cooled and the crystals precipitated were collected by filtration. The mother liquor obtained from the first distillate was combined with second distillate, and this mixture was saturated with sodium chloride, then was extracted with ether extract was dried with sodium sulfate, and ether was removed by distillation. The residue thus obtained was combined with the crystals precipitated from the first distillate and the mixture was dried to obtain 2.9 g of o-aminobenzaldehyde in the form of yellowish flake-like crystals.

Melting point: 38°–39° C.

(b) 2 Grams of malonic acid was dissolved in 15 ml of pyridine, then 1.2 g of o-aminobenzaldehyde and 2 ml of piperidine were added thereto, and the mixture was stirred at 90° C. for 5 hours. The reaction mixture was poured in an aqueous solution of hydrochloric acid and the crystals precipitated were collected by filtration. Recrystallized from methanol-chloroform to obtain 1.2 g of 3-carboxycarbostyril in the form of colorless needle-like crystals.

Melting point: Over 300° C.

REFERENCE EXAMPLE 66

To 60 g of isatin was added 140 ml of acetic anhydride and the mixture was refluxed for 4 hours. The reaction mixture was cooled, and the crystals precipitated were collected by filtration, and washed with ether to obtain 58 g of N-acetylisatin.

To a solution containing 30 g of sodium hydroxide in 1.5 liter of water was added 58 g of the above-mentioned N-acetylisatin and the mixture was refluxed for 1 hour. Then the reaction mixture was cooled a certain extent, then activated carbon was added and further refluxed for 30 minutes. The activated carbon was removed from the reaction mixture by filtration while the mixture being hot, and the mother liquor was cooled, then 6N-hydrochloric acid was added to the mother liquor to adjust the pH thereof to pH 3–4. The crystals precipitated were colledted by filtration, washed with water, dried to obtain 45 g of 4-carboxycarbostyril.

Melting point: Over 300° C.

REFERENCE EXAMPLE 67

(a) Under ice-cooled condition with stirring, 322 ml of phosphorus oxychloride was added dropwise to 96 ml of N,N-dimethylformamide. At the same temperature, 67.5 g of acetanilide was added thereto and the mixture was stirred at 75° C. for 18.5 hours. The reaction mixture was poured to ice and the crystals precipitated were collected by filtration, and dried. Rescrystallization from ethyl acetate to obtain 55.2 g of 2-chloro-3-formylcarbostyril in the form of yellowish needle-like crystal.

Melting point: 149°–151° C.

(b) To 37 g of 2-chloro-3-formylquinoline was added 600 ml of 4N-hydrochloric acid and the mixture was refluxed for 1 hour. After cooled the reaction mixture, the crystals precipitated therefrom were collected by filtration, recrystallized from ethanolchloroform to obtain 34 g of 3-formylcarbostyril in the form of light yellowish needle-like crystals.

Melting point: 308°–209° C.

(c) 2.7 Grams of 3-formylcarbostyril was dissolved in 150 ml of tetrahydrofuran, then 0.8 g of oil 50%-sodium hydride was added thereto at a room temperature with stirring. Next, 4.5 g of methyl iodide was added dropwise at a room temperature for 3 hours. The reaction mixture was concentrated under a reduced pussure, the residue thus obtained was poured into water and the crystals precipitated were collected by filtration. Recrystallized from ethanol to obtain 1.7 g of 1-methyl-3-formylcarbostyril in the form of yellow-brownish needle-like crystals.

Melting point: 211°–214° C.

REFERENCE EXAMPLE 68

Under a stirring condition at 0° C., 64.4 ml of phosphorus oxychloride was added dropwise to 11.6 ml of N,N-dimethylformamide. At the same temperature, 18.4 g of N-phenyl-3-chloropropionamide was added thereto, and the reaction mixture was further stirred at 75°–80° C. for 10 hours. The reaction mixture was poured into an ice-water, and the crystals precipitated were collected by filtration. Recrystallized from ethanol to obtain 6.7 g of 2-chloro-c-chloromethylquinoline in the form of colorless prism-like crystals.

Melting point: 116°–118° C.

REFERENCE EXAMPLE 69

17 Grams of 4-formylcarbostyril, 18 g of N-acetylglycine, 7 g of anhydrous sodium acetate and 100 ml of acetic anhydride were heated at 110° C. to make a homogeneous solution, further the solution was refluxed for 1.5 hours. After cooled the reaction mixture, the reaction mixture was poured in a cold water and the crystals precipitated were collected by filtration. The crystals were washed with cold water, then recrystallized from ethanol-chloroform to obtain 10 g of 4-(1,2-dihydro-2-oxo-4-quinolyliden)-2-methyl-5-oxazolone.½-hydrate.

Melting point: 275°–277° C. (decomp.)

REFERENCE EXAMPLES 70–71

By a method similar to that described in Reference Example 67, by using a suitable starting material, there were prepared compounds as shown in Table 4 as follows.

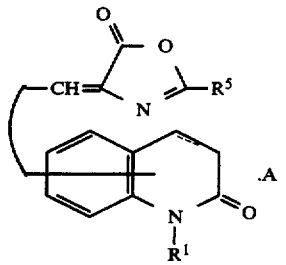

TABLE 4

| Reference Example | $R^1$ | $R^5$ | Substituted position of the side-chain | Carbon-carbon bond between 3- or 4-positions | Crystal form (Solvent) | Melting point (°C.) |
|---|---|---|---|---|---|---|
| 70 | $CH_3$ | 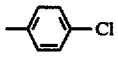 | 3 | Double bond | Orange needle-like crystals (Ethanol-chloroform) [Salt: A = ½.$H_2O$] | 265–266 (decomp.) |
| 71 | $CH_3$ | $-CH_3$ | 3 | Double bond | Red brownish needle-like crystals (Ethanol) | 200–203 (decomp.) |

EXAMPLE 1

To 5 g of ethy 2-acetamido-2-carboxy-3-(2-quinolon-4-yl)propionate was added 150 ml of 20%-hydrochloric acid and the mixture was refluxed for 9 hours. The reaction mixture was concentrated under a reduced pressure, the residue was recrystallized from ethanon-water to obtain 3.2 g of 2-amino-3-(2-quinolon-4-yl)propionic acid hydrochloride hydrate in the form of folorless prism-like crystals.

Melting point: 220°–225° C. (decomp.)

EXAMPLE 2

1.6 Grams of 2-amino-3-(2-quinolon-3-yl)propionic acid hydrochloride and 2.4 g of potassim carbonate were dissolved in 60 ml of acetone with 30 ml of water, then to this mixture was added a solution containing 1.2 g of p-chlorobenzol chloride in 10 ml of acetone dropwise under a condition of ice-cooled with stripping. The reaction was continued under ice-cooled condition for 2 hours. After removal of acetone by distillation, to the residue was added water to remove the insolubles by filtration. The filtrate was acidified by adding hydrochloric acid, the crystals precipitated were collected by filtration. Recrystallized from ethanol-water to obtain 1.5 g of 2-(4-chlorobenzoylamino)-3-(2-quinolon-3-yl)propinoic acid in the form of white powdery product.

Melting point: 270°–271.5° C. (decomp.)

EXAMPLE 3

1.5 Grams of 2-amino-3-(6-methoxy-2-quinolon-3-yl)propionic acid hydrochloride was dissolved in a solution containing 0.8 g of sodium hydroxide in 25 ml of water, then under ice-cooled condition, 1 g of p-chlorobenzoyl chloride was added dropwise with stirring. The reaction was carried out by adding 1N-sodium hydroxide aqueous solution and p-chlorobenzoyl chloride properly, until the starting material os disappeared from the reaction mixture by checking a sample of the reaction mixture through a thin-layer-chromatograph. After completion of the reaction, the reaction mixture was acidified with hydrochloric acid, the crystals precipitated were collected by filtration. The crystals were washed with ether, then recrystallized from methanol-water to obtain 0.7 g of 2-(4-chlorobenzoylamino)-3-(6-methoxy-2-quinolon-3-yl)propionic acid in the from of yellowish powdery product.

Melting point: 234.5°–236° C. (decomp.)

EXAMPLE 4

2 Grams of 2-amino-3-(6-hydroxy-2-quinolon-3-yl)propionic acid hydrochloride was suspended in 50 ml of 1-methyl-2-pyrrolidone, then 2.2 g of 3-(4-chlorobenzoyl)benzoxazoline-2-thione was added thereto and stirred at a room temperature for 3 days. The reaction mixture was poured in ice-water and the crystals precipitated were collected by filtration. The crystals were dissolved in 1N-sodium hydroxide aqueous solution, and acidified with 10%-hydrochloric acid, then the crystals precipitated were collected by filtration. The crystals were dried and washed with chloroform. Recrystallized from methanol-water to obtain 1.5 g of 2-(4-chlorobenzoylamino)-3-(6-hydroxy-2-quinolon-3-yl)propionic acid in the form of light yellowish powdery product.

Melting point: 223°–227° C. (decomp.)

EXAMPLE 5

1.2 Grams of 2-amino-3-(2-quinolon-3-yl)propionic acid, 1.3 g of DCC [dicyclohexylcarbodiimide] and 1.0 g of p-chlorobenzoic acid were suspended in 10 ml of dioxane, and the suspension was stirred at 60°–70° C. for 5 hours. After completion of the reaction, the solvent was removed by distillation, then to the residue was added ether and the crystals precipitate were removed by filtration. The filtrated was connectrated, and the residue obtained was dissolved in chloroform, and washed with water and with a saturated sodium chloride aqueous solution. The chloroform layer was dried with sodium sulfate then the solvent was removed by distillation. The residue was recrystallized from ethanol-water to obtian 350 mg of 2-(4-chlorobenzoylamino)-3-(2-quinolon-3-yl)propionic acid in the form of white powdery product.

Melting point: 270°–271.5° C. (decomp.)

EXAMPLE 6

1.2 Grams of 2-amino-3-(2-quinolon-3-yl)propionic acid and 0.8 ml of triethylamine were suspended in 10 ml of tetrahydrofuran, then under stirring condition at a room temperature, a solution containing 1.0 g of diethyl chlorophosphate in 10 ml of tetrahydrofuran was added dropwise thereto, and the reaction mixture was stirred at a room temperature for 3 hours. To this reaction mixture was added a solution containing 1.0 g of p-chlorobenzoic acid in 10 ml of tetrahydrofuran dropwise and the whole reaction mixture was further stirred at a room temperature for 10 hours. After completion of the reaction, the crystals precipitated were removed by filtration, the filtrate was concentrated and to the residue was poured a saturated sodium hydrogencarbonate aqueous solution, then extracted with chloroform. The organic layer was washed with water and a saturated sodium chloride aqueous solution and dried with sodium sulfare. The solvent was removed by distillation and the residue was recrystallized from ethanol-water to obtain 0.9 g of 2-(4-chlorobenzoylamino)-3-(2-quinolon-3-yl)propionic acid in the form of white powder product.

Melting point: 270°-271.5° C. (decomp.)

EXAMPLE 7

To a solution containing 4.84 g of p-chlorobenzoic acid and 4 ml of triethylamine in 50 ml of dimethylformamide was added dropwise a solution containing 3.87 g of isobutyl chloroformate in 2 ml of dimethylformaide. The reaction mixture was stirred at a room temperature for 30 minutes, then a solution containing 6.03 g of 2-amino-3-(2-quinolon-3-yl)propionic acid in 3 ml of dimethylformaide was added dropwise thereto and stirred at a room temperature for 30 minutes, further stirred at 50°-60° C. for 1 hour. The reaction mixture was poured into a large amount of a saturated sodium chloride aqueous solution, extracted with chloroform, washed with water and dried. The solvent was removed by distillation and the drude crystals obtained were recrystallized from ethanol-water to obtain 3.7 g of 2-(4-chlorobenzoylamino)-3-(2-quinolon-3-yl)pripionic acid in the form of white powdery product.

Melting point: 270°-271.5° C. (decomp.)

EXAMPLE 8

In 100 ml of ethanol, 1.66 g of ethyl p-chlorobenzate, 0.5 g of sodium ethylate and 2.09 g of 2-amino-3-(2-quinolon-3-yl)propionic acid were added and the whole mixture was placed in an autoclave. The reaction was carried out under 110 atmospheric pressure at 140°-150° C. for 6 hours. After completion of the reaction, the reaction mixture was cooled and concentrated under a reduced pressure. The residue was dissolved in 200 ml of chloroform, washed with 1%-potassium carbonate aqueous solution, a diluted hydrochloric acid and water in this order, then the chloroform layer was dried with sodium sulfate. The solvent was removed by distillation, the residue was recrystallized from ethanol-water to obtain 300 mg of 2-(4-chlorobenzoylamino)-3-(2-quinolon-3-yl)propionic acid in the form of white powdery product.

Melting point: 270°-271.5° C. (decomp.)

EXAMPLES 9-32

By a method similar to that described in Example 1, by using a suitable starting material, there were prepared compounds as shown in Table 5 as follows.

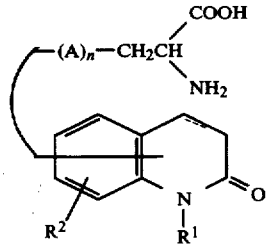

TABLE 5

| Example | $R^1$ | $R^2$ | Substituted position of the side chain of $-(A)_n-CH_2CH(COOH)(NH_2)$ | Carbon-carbon bond between 3- and 4-positions | Crystal form | Recrystallization solvent | Melting point (°C.) | Type of the salt | $(A)_n$ |
|---|---|---|---|---|---|---|---|---|---|
| 9 | H | H | 3 | Double bond | White powdery product | Methanol-acetone | 271–272 (decomp.) | HCl | — |
| 10 | $CH_3$ | H | 3 | Double bond | White granular crystals | Ethanol | 218–225 (decomp.) | HCl | — |
| 11 | H | 6-$OCH_3$ | 3 | Double bond | Colorless powdery product | Water | 293–295 (decomp.) | HCl.$\frac{1}{2}H_2O$ | — |
| 12 | H | 6-OH | 3 | Double bond | Yellowish powdery product | Water | Over 300 | HBr | — |
| 13 | H | H | 4 | Single bond | Colorless powdery product | Ethanol-ether | 237–238 (decomp.) | HCl.$\frac{1}{4}H_2O$ | — |
| 14 | $CH_3$ | H | 4 | Double bond | Colorless prism-like crystals | Ethanol | 175–178 (decomp.) | HCl.$H_2O$ | — |
| 15 | $C_2H_5$ | H | 4 | Double bond | White powdery product | Methanol | 255–260 (decomp.) | HCl | — |
| 16 | $-CH_2CH=CH_2$ | H | 4 | Double bond | Colorless prism-like crystals | Methanol | 166–171 (decomp.) | HCl.$H_2O$ | — |
| 17 | $-CH_2C\equiv CH$ | H | 4 | Double bond | White powdery product | Methanol | 218–221 (decomp.) | $H_2O$ | — |
| 18 | $-CH_2-$ 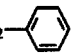 | H | 4 | Double bond | White powdery product | Ethanol | 166–169 (decomp.) | HCl | — |
| 19 | H | H | 5 | Double bond | Colorless powdery product | Water | Over 300 | HCl | — |
| 20 | H | 8-$OCH_3$ | 5 | Double bond | Colorless powdery product | Water | 257–260 (decomp.) | HCl.$H_2O$ | — |
| 21 | H | 8-OH | 5 | Double bond | Colorless powdery product | Methanol-ether | 290–292 (decomp.) | HBr.$\frac{1}{2}H_2O$ | — |
| 22 | H | H | 6 | Single bond | Colorless granular crystals | Methanol-ether | 283–285 (decomp.) | HCl | — |
| 23 | H | H | 3 | Single bond | White powdery product | Ethanol | 208–210 (decomp.) | HCl | — |
| 24 | $-C_2H_5$ | H | 3 | Double bond | White powdery product | Ethanol | 244–246 (decomp.) | HCl | — |
| 25 | $-n\text{-}C_4H_9$ | H | 4 | Double bond | White powdery product | Ethanol | 169–170 (decomp.) | HCl.$\frac{3}{8}H_2O$ | — |
| 26 | H | 8-$CH_3$ | 4 | Double bond | White powdery product | Ethanol | 229–231 (decomp.) | HCl.$\frac{3}{8}H_2O$ | — |
| 27 | H | 6-$OCH_3$ | 4 | Double bond | White powdery product | Ethanol | 246–248 (decomp.) | HCl.$\frac{3}{8}H_2O$ | — |
| 28 | H | 8-Cl | 4 | Double bond | White powdery product | Ethanol | 260–261 (decomp.) | HCl | — |
| 29 | H | 8-$C_2H_5$ | 4 | Double bond | White powdery product | Ethanol | Over 320 | HCl.$\frac{1}{3}H_2O$ | — |
| 30 | H | 6-OH | 4 | Double bond | White powdery | Dimethylformamide- | Over 300 | HCl | — |

TABLE 5-continued

| Example | $R^1$ | $R^2$ | Substituted position of the side chain of $-(A)_n-CH_2CH(COOH)(NH_2)$ | Carbon-carbon bond between 3- and 4-positions | Crystal form | Recrystallization solvent | Melting point (°C.) | Type of the salt | $(A)_n$ |
|---|---|---|---|---|---|---|---|---|---|
| 31 | H | H | 4 | Double bond | product White powdery product | water | | | $CH_2CH_2$ (+) |
| 32 | H | H | 4 | Double bond | White powdery product | Water | 296–298 (decomp.) | HCl | $CH_2$ |

(+) NMR δ (DMSO) 8.60 (2H, b, s), 7.00–8.00 (4H, m), 6.52 (1H, s), 3.80–4.10 (1H, m), 2.70–3.10 (2H, m), 1.50–2.20 (4H, m).

EXAMPLE 33–126
By a method similar to that described in any one of Examples 2 and 5–8, by using a suitable starting material, there were prepared compounds as shown in Table 6 as follows.
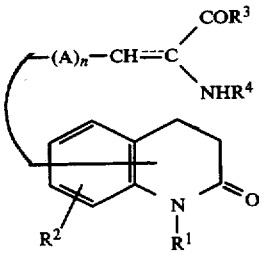

TABLE 6
| Example | $R^1$ | $R^2$ | $R^3$ | $R^4$ | Substituted position of the side-chain of $-(A)_n-CH=C(COR^3)(NHR^4)$ | Carbon-carbon bond between 3- and 4-position |
|---|---|---|---|---|---|---|
| 33 | H | H | OH | $COCH_3$ | 3 | Double bond |
| 34 | H | H | OH | $COC_2H_5$ | 3 | Double bond |
| 35 | H | H | OH | 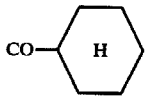 | 3 | Double bond |
| 36 | H | H | OH | 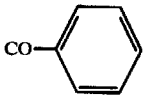 | 3 | Double bond |
| 37 | H | H | OH | 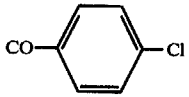 | 3 | Single bond |
| 38 | H | H | OH | $CO(CH_2)_2NH$ cbz* | 3 | Double bond |
| 39 | H | H | OH | $CO(CH_2)_2NH_2$ | 3 | Double bond |
| 40 | $CH_3$ | H | OH | 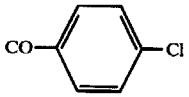 | 3 | Double bond |
| 41 | H | H | OH | 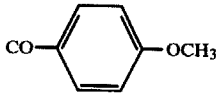 | 3 | Double bond |
| 42 | H | H | OH | 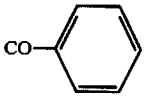 | 4 | Double bond |

TABLE 6-continued
| | | | | | | |
|---|---|---|---|---|---|---|
| 43 | H | H | OH | 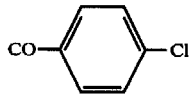 | 4 | Double bond |
| 44 | H | H | $OCH_3$ | 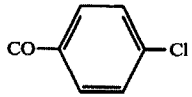 | 4 | Double bond |
| 45 | H | H | OH | $CO(CH_2)_2NH.cbz^*$ | 4 | Double bond |
| 46 | H | H | OH | $CO(CH_2)_2NH_2$ | 4 | Double bond |
| 47 | H | H | OH | 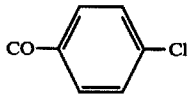 | 4 | Single bond |
| 48 | H | H | OH | 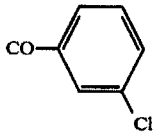 | 4 | Double bond |
| 49 | H | H | OH | 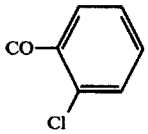 | 4 | Double bond |
| 50 | H | H | OH | 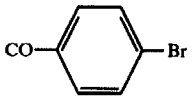 | 4 | Double bond |
| 51 | H | H | OH | 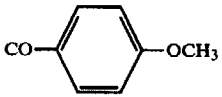 | 4 | Double bond |

TABLE 6-continued
| | | | | | | |
|---|---|---|---|---|---|---|
| 52 | H | H | OH | 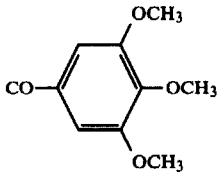 | 4 | Double bond |
| 53 | H | H | OH | 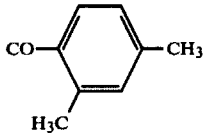 | 4 | Double bond |
| 54 | H | H | OH | 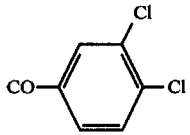 | 4 | Double bond |
| 55 | H | H | OH | 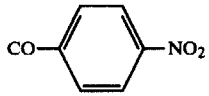 | 4 | Double bond |
| 56 | H | H | OH | 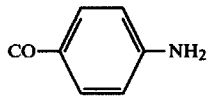 | 4 | Double bond |
| 57 | $CH_3$ | H | OH | 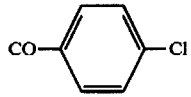 | 4 | Double bond |
| 58 | $C_2H_5$ | H | OH | 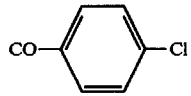 | 4 | Double bond |
| 59 | $-CH_2CH{=}CH_2$ | H | OH | 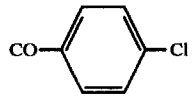 | 4 | Double bond |

TABLE 6-continued

| | | | | | | |
|---|---|---|---|---|---|---|
| 60 | $-CH_2C{\equiv}CH$ | H | OH | 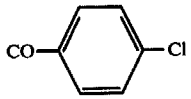 | 4 | Double bond |
| 61 | 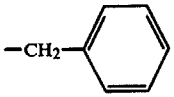 | H | OH | 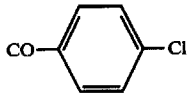 | 4 | Double bond |
| 62 | H | H | OH | 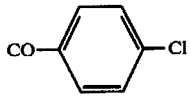 | 5 | Double bond |
| 63 | H | 8-$OCH_3$ | OH | 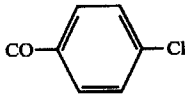 | 5 | Double bond |
| 64 | H | 8-OH | OH | 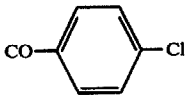 | 5 | Double bond |
| 65 | H | H | OH | 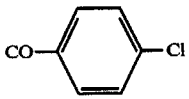 | 6 | Single bond |
| 66 | H | H | OH | H | 3 | Double bond |
| 67 | $CH_3$ | H | OH | H | 3 | Double bond |
| 68 | H | 6-$OCH_3$ | OH | H | 3 | Double bond |
| 69 | H | 6-OH | OH | H | 3 | Double bond |
| 70 | H | H | OH | H | 4 | Single bond |
| 71 | H | H | OH | H | 4 | Double bond |
| 72 | $CH_3$ | H | OH | H | 4 | Double bond |
| 73 | $C_2H_5$ | H | OH | H | 4 | Double bond |
| 74 | $-CH_2CH{=}CH_2$ | H | OH | H | 4 | Double bond |
| 75 | $-CH_2C{\equiv}CH$ | H | OH | H | 4 | Double bond |
| 76 | 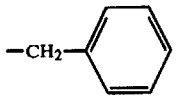 | H | OH | H | 4 | Double bond |

TABLE 6-continued
| | | | | | | |
|---|---|---|---|---|---|---|
| 77 | H | H | OH | H | 5 | Double bond |
| 78 | H | 8-$OCH_3$ | OH | H | 5 | Double bond |
| 79 | H | 8-OH | OH | H | 5 | Double bond |
| 80 | H | H | OH | H | 6 | Single bond |
| 81 | H | 8-$OCH_3$ | OH | $COCH_3$ | 5 | Double bond |
| 82 | H | 6-$OCH_3$ | OH | 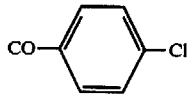 | 3 | Double bond |
| 83 | H | 6-OH | OH | 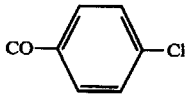 | 3 | Double bond |
| 84 | H | H | OH | H | 3 | Single bond |
| 85 | H | H | OH | 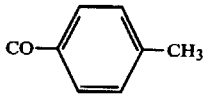 | 4 | Double bond |
| 86 | H | H | OH | 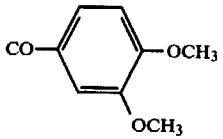 | 3 | Double bond |
| 87 | H | H | $OC_2H_5$ | 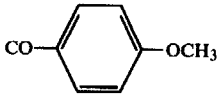 | 3 | Double bond |
| 88 | H | H | OH | 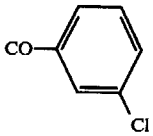 | 3 | Double bond |

TABLE 6-continued
| | | | | | | |
|---|---|---|---|---|---|---|
| 89 | H | H | OH | 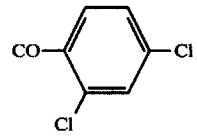 | 4 | Double bond |
| 90 | H | H | OH | 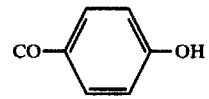 | 4 | Double bond |
| 91 | H | H | OH | 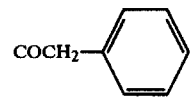 | 4 | Double bond |
| 92 | H | 8-$CH_3$ | OH | 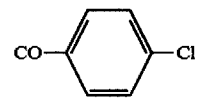 | 4 | Double bond |
| 93 | H | H | OH | 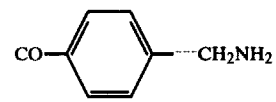 | 4 | Double bond |
| 94 | H | H | OH | 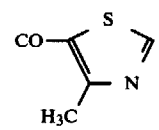 | 4 | Double bond |
| 95 | H | H | OH | 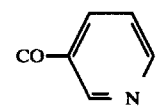 | 4 | Double bond |
| 96 | H | H | OH | 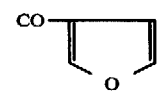 | 4 | Double bond |

TABLE 6-continued
| | | | | | | |
|---|---|---|---|---|---|---|
| 97 | H | H | OH | 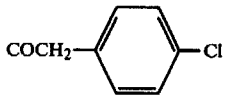 | 4 | Double bond |
| 98 | $CH_3$ | H | OH | 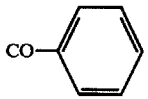 | 3 | Double bond |
| 99 | $C_2H_5$ | H | OH | 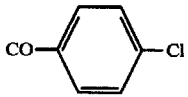 | 3 | Double bond |
| 100 | $C_2H_5$ | H | OH | 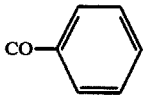 | 4 | Double bond |
| 101 | H | H | $NH_2$ | 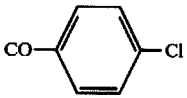 | 4 | Double bond |
| 102 | H | H | 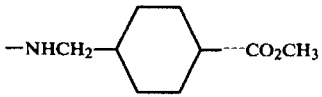 | 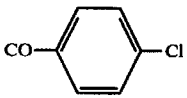 | 4 | Double bond |
| 103 | H | H | 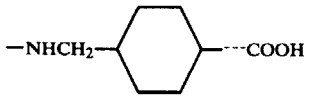 | 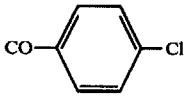 | 4 | Double bond |
| 104 | $CH_3$ | H | OH | $COCH_3$ | 3 | Double bond |
| 105 | H | H | OH | 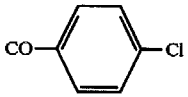 | 3 | Double bond |

TABLE 6-continued
| | | | | | | |
|---|---|---|---|---|---|---|
| 106 | $C_2H_5$ | H | OH | 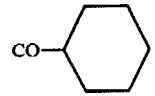 | 4 | Double bond |
| 107 | $C_2H_5$ | H | OH | 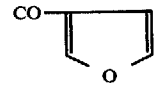 | 4 | Double bond |
| 108 | n-$C_4H_9$ | H | OH | 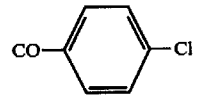 | 4 | Double bond |
| 109 | $CH_3$ | H | OH | 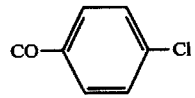 | 3 | Double bond |
| 110 | $C_2H_5$ | H | OH | 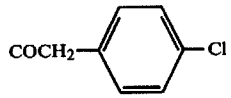 | 4 | Double bond |
| 111 | $CH_3$ | H | OH | 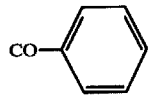 | 4 | Double bond |
| 112 | H | H | OH | 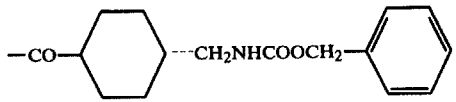 | 4 | Double bond |
| 113 | H | H | OH | 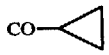 | 4 | Double bond |
| 114 | H | H | OH | 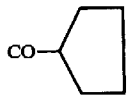 | 4 | Double bond |

TABLE 6-continued
| | | | | | | |
|---|---|---|---|---|---|---|
| 115 | H | H | OH | 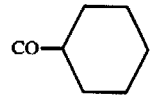 | 4 | Double bond |
| 116 | H | H | OH | 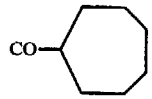 | 4 | Double bond |
| 117 | H | H | $OCH_2COOCH_3$ | 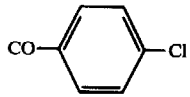 | 4 | Double bond |
| 118 | H | H | $OCH_2CO$ | 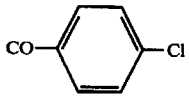 | 4 | Double bond |
| 119 | H | H | $OCH_2OC(=O)C(CH_3)_3$ | 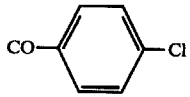 | 4 | Double bond |
| 120 | H | 8-Cl | OH | 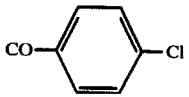 | 4 | Double bond |
| 121 | H | 6-OH | OH | 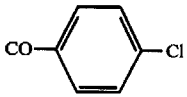 | 4 | Double bond |
| 122 | H | 6-$OCH_3$ | OH | 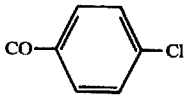 | 4 | Double bond |
| 123 | H | 8-$C_2H_5$ | OH | 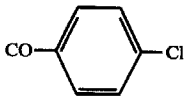 | 4 | Double bond |

TABLE 6-continued

| | | | | | | |
|---|---|---|---|---|---|---|
| 124 | H | 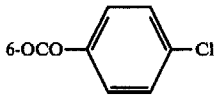 | OH | 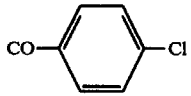 | 4 | Double bond |
| 125 | H | H | OH | 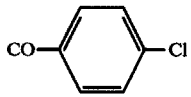 | 4 | Double bond |
| 126 | H | H | OH | 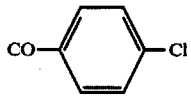 | 4 | Double bond |

| Example | $-CH=C<$ | $(A)_n$ | Crystal form | Recrystallization solvent | Melting point (°C.) | Type of the salt |
|---|---|---|---|---|---|---|
| 33 | $-CH_2CH<$ | — | Light yellowish product | Water | 228–231 (decomp.) | — |
| 34 | $-CH_2CH<$ | — | White powdery product | Water | 212–215 (decomp.) | — |
| 35 | $-CH_2CH<$ | — | White powdery product | Methanol | 261–264 (decomp.) | — |
| 36 | $-CH_2CH<$ | — | White powdery product | Ethanol | 255–257.5 (decomp.) | — |
| 37 | $-CH_2CH<$ | — | Colorless prism-like crystals | Ethyl acetate-hexane | 201.5–203.5 | — |

TABLE 6-continued

| | | | | | | |
|---|---|---|---|---|---|---|
| 38 | $-CH_2CH\begin{matrix}/\\ \backslash\end{matrix}$ | — | White powdery product | Ethanol-ether | 190–192 (decomp.) | — |
| 39 | $-CH_2CH\begin{matrix}/\\ \backslash\end{matrix}$ | — | White powdery product | Methanol | 250–253 (decomp.) | — |
| 40 | $-CH_2CH\begin{matrix}/\\ \backslash\end{matrix}$ | — | White powdery product | Ethanol | 246–247.5 (decomp.) | — |
| 41 | $-CH_2CH\begin{matrix}/\\ \backslash\end{matrix}$ | — | White powdery product | Ethanol | 249–251 (decomp.) | — |
| 42 | $-CH_2CH\begin{matrix}/\\ \backslash\end{matrix}$ | — | Colorless prism-like crystals | Ethanol | 280–282 (decomp.) | $H_2O$ |
| 43 | $-CH_2CH\begin{matrix}/\\ \backslash\end{matrix}$ | — | White powdery product | Methanol-chloroform | 288–290 (decomp.) | $\frac{1}{2}H_2O$ |
| 44 | $-CH_2CH\begin{matrix}/\\ \backslash\end{matrix}$ | — | Colorless needle-like crystals | Methanol-chloroform | 275–276.5 (decomp.) | $\frac{1}{2}H_2O$ |
| 45 | $-CH_2CH\begin{matrix}/\\ \backslash\end{matrix}$ | — | White cotton-like crystals | Methanol chloroform | 250–252 (decomp.) | $\frac{1}{2}H_2O$ |
| 46 | $-CH_2CH\begin{matrix}/\\ \backslash\end{matrix}$ | — | White powdery product | Methanol | 270–271 (decomp.) | $HBr.\frac{1}{2}H_2O$ |

TABLE 6-continued

| | | | | | | |
|---|---|---|---|---|---|---|
| 47 | $-CH_2CH\begin{matrix}/\\ \backslash\end{matrix}$ | — | White powdery product | Methanol-water | 256–257 (decomp.) | — |
| 48 | $-CH_2CH\begin{matrix}/\\ \backslash\end{matrix}$ | — | Colorless needle-like crystals | Methanol-water | 265–267 (decomp.) | — |
| 49 | $-CH_2CH\begin{matrix}/\\ \backslash\end{matrix}$ | — | White powdery product | Methanol-water | 270.5–271.5 (decomp.) | $\frac{1}{2}H_2O$ |
| 50 | $-CH_2CH\begin{matrix}/\\ \backslash\end{matrix}$ | — | White powdery | Dimethyl-formamide-water | 287–288.5 (decomp.) | $\frac{1}{2}H_2O$ |
| 51 | $-CH_2CH\begin{matrix}/\\ \backslash\end{matrix}$ | — | White powdery product | Acetone-water | 259–261 (decomp.) | — |
| 52 | $-CH_2CH\begin{matrix}/\\ \backslash\end{matrix}$ | — | White powdery product | Methanol | 256–258 (decomp.) | — |
| 53 | $-CH_2CH\begin{matrix}/\\ \backslash\end{matrix}$ | — | White powdery product | Dimethyl-formamide-water | 287–289 (decomp.) | $\frac{1}{2}H_2O$ |
| 54 | $-CH_2CH\begin{matrix}/\\ \backslash\end{matrix}$ | — | White powdery product | Dimethyl-formamide-water | 287–280 (decomp.) | — |
| 55 | $-CH_2CH\begin{matrix}/\\ \backslash\end{matrix}$ | — | White powdery product | Dimethyl-formamide-water | 290–291 (decomp.) | — |

TABLE 6-continued

| | | | | | | |
|---|---|---|---|---|---|---|
| 56 | $-CH_2CH<$ | — | White powdery product | Dimethyl-formamide-water | 240–242 (decomp.) | — |
| 57 | $-CH_2CH<$ | — | Colorless needle-like crystals | Ethanol | 247–249 (decomp.) | — |
| 58 | $-CH_2CH<$ | — | Colorless prism-like crystals | Ethanol | 134–138 | $\frac{1}{2}H_2O^{(++)}$ |
| 59 | $-CH_2CH<$ | — | Light yellowish powdery product | Ethyl acetate | 130–135 | — |
| 60 | $-CH_2CH<$ | — | Colorless needle-like crystals | Methanol-water | 271–272 (decomp.) | $H_2O$ |
| 61 | $-CH_2CH<$ | — | White powdery product | Methanol-water | 230–231 (decomp.) | $H_2O$ |
| 62 | $-CH_2CH<$ | — | Colorless needle-like crystals | Dimethyl-formamide-water | Over 300 | — |
| 63 | $-CH_2CH<$ | — | Light yellowish powdery product | Dimethyl-formamide-water | 299–300 (decomp.) | — |
| 64 | $-CH_2CH<$ | — | Colorless powdery product | Dimethyl-formamide-water | Over 300 | — |

TABLE 6-continued

| | | | | | | |
|---|---|---|---|---|---|---|
| 65 | $-CH_2CH\begin{matrix}/\\ \backslash\end{matrix}$ | — | Colorless powdery product | Ethanol | 251–252 (decomp.) | — |
| 66 | $-CH_2CH\begin{matrix}/\\ \backslash\end{matrix}$ | — | White powdery product | Methanol-acetone | 271–272 (decomp.) | HCl |
| 67 | $-CH_2CH\begin{matrix}/\\ \backslash\end{matrix}$ | — | White granular products | Ethanol | 218–225 (decomp.) | HCl |
| 68 | $-CH_2CH\begin{matrix}/\\ \backslash\end{matrix}$ | — | Colorless powdery product | Water | 293–295 (decomp.) | $HCl.\frac{1}{2}H_2O$ |
| 69 | $-CH_2CH\begin{matrix}/\\ \backslash\end{matrix}$ | — | Yellowish powdery product | Water | Over 300 | HBr |
| 70 | $-CH_2CH\begin{matrix}/\\ \backslash\end{matrix}$ | — | Colorless powdery product | Ethanol-ether | 237–238 (decomp.) | $HCl.\frac{1}{4}H_2O$ |
| 71 | $-CH_2CH\begin{matrix}/\\ \backslash\end{matrix}$ | — | Colorless prism-like crystals | Ethanol-water | 220–225 (decomp.) | $HCl.H_2O$ |
| 72 | $-CH_2CH\begin{matrix}/\\ \backslash\end{matrix}$ | — | Colorless prism-like crystals | Ethanol | 175–178 (decomp.) | $HCl.H_2O$ |
| 73 | $-CH_2CH\begin{matrix}/\\ \backslash\end{matrix}$ | — | White powder product | Methanol | 255–260 (decomp.) | HCl |

TABLE 6-continued

| | | | | | | |
|---|---|---|---|---|---|---|
| 74 | $-CH_2CH<$ | — | Colorless prism-like crystals | Ethanol | 166–171 (decomp.) | $HCl.H_2O$ |
| 75 | $-CH_2CH<$ | — | White powdery product | Methanol | 218–221 (decomp.) | $H_2O$ |
| 76 | $-CH_2CH<$ | — | White powdery product | Ethanol | 166–169 (decomp.) | HCl |
| 77 | $-CH_2CH<$ | — | Colorless powdery product | Water | Over 300 | HCl |
| 78 | $-CH_2CH<$ | — | Colorless powdery product | Water | 257–260 (decomp.) | $HCl.H_2O$ |
| 79 | $-CH_2CH<$ | — | Colorless powdery product | Methanol-ether | 290–292 (decomp.) | $HBr.\frac{1}{2}H_2O$ |
| 80 | $-CH_2CH<$ | — | Colorless granular crystals | Methanol-ether | 283–285 (decomp.) | HCl |
| 81 | $-CH=C<$ | — | Colorless needle-like-crystals | Ethanol | 264–265 (decomp.) | $\frac{1}{2}H_2O$ |
| 82 | $-CH_2CH<$ | — | Yellowish powdery product | Methanol-water | 234.5–236 (decomp.) | — |

TABLE 6-continued

| | | | | | | |
|---|---|---|---|---|---|---|
| 83 | $-CH_2CH\langle$ | — | Light yellowish powdery product | Methanol-water | 223–227 (decomp.) | — |
| 84 | $-CH_2CH\langle$ | — | White powdery product | Ethanol | 208–210 (decomp.) | HCl |
| 85 | $-CH_2CH\langle$ | — | White powdery product | Ethanol-water | 284–286 (decomp.) | $\frac{1}{2}H_2O$ |
| 86 | $-CH_2CH\langle$ | — | White powdery product | Ethanol-water | 200–205 (decomp.) | $\frac{1}{4}H_2O$ |
| 87 | $-CH_2CH\langle$ | — | White powdery product | Ethyl acetate-ethanol | 206–208.5 (decomp.) | — |
| 88 | $-CH_2CH\langle$ | — | Light yellowish powdery product | Dimethyl-formamide-water | 278–279 (decomp.) | — |
| 89 | $-CH_2CH\langle$ | — | White powdery product | Water | 281–282 (decomp.) | — |
| 90 | $-CH_2CH\langle$ | — | White powdery product | Ethanol | 305.5–306.5 (decomp.) | $\frac{3}{2}H_2O$ |
| 91 | $-CH_2CH\langle$ | — | Light yellowish powdery product | Ethanol | 271.5–272.5 (decomp.) | $H_2O$ |

TABLE 6-continued

| | | | | | | |
|---|---|---|---|---|---|---|
| 92 | $-CH_2CH\langle$ | — | Light yellowish powdery product | Dimethyl-formamide-water | 278–279 (decomp.) | — |
| 93 | $-CH_2CH\langle$ | — | White powdery product | Water | 320 (decomp.) | — |
| 94 | $-CH_2CH\langle$ | — | White powdery product | Methanol | 261–263 (decomp.) | $\frac{1}{2}H_2O$ |
| 95 | $-CH_2CH\langle$ | — | White powdery product | Ethanol | 298–299 (decomp.) | $\frac{1}{2}H_2O$ |
| 96 | $-CH_2CH\langle$ | — | White powdery product | Ethanol-water | 283–286 (decomp.) | $\frac{1}{2}H_2O$ |
| 97 | $-CH_2CH\langle$ | — | White powdery product | Ethanol-water | 280.5–282.5 (decomp.) | $H_2O$ |
| 98 | $-CH_2CH\langle$ | — | Light yellowish powdery product | Ethanol | 234.5–236 (decomp.) | — |
| 99 | $-CH_2CH\langle$ | — | White powdery product | Ethanol | 208–211 | — |
| 100 | $-CH_2CH\langle$ | — | White powdery product | Ethanol | 226–228 (decomp.) | — |

TABLE 6-continued

| | | | | | | |
|---|---|---|---|---|---|---|
| 101 | $-CH_2CH\langle$ | — | Light yellowish powdery product | Dimethyl-formamide-water | Over 300 | — |
| 102 | $-CH_2CH\langle$ | — | White powdery product | Dimethyl-formamide-water | 298–299 (decomp.) | — |
| 103 | $-CH_2CH\langle$ | — | White powdery product | Dimethyl-formamide-water | 303–305 (decomp.) | — |
| 104 | $-CH{=}C\langle$ | — | Yellowish-brownish powdery product | Ethanol-chloroform | 241.5–242.5 (decomp.) | — |
| 105 | $-CH{=}C\langle$ | — | White powdery product | Ethanol-water | 275–280 (decomp.) | $\frac{1}{3}H_2O$ |
| 106 | $-CH_2CH\langle$ | — | Colorless needle-like crystals | Ethanol-water | 220.5–222 (decomp.) | — |
| 107 | $-CH_2CH\langle$ | — | White powdery product | Ethyl acetate-hexane | 135–137 (decomp.) | $\frac{1}{3}H_2O$ |
| 108 | $-CH_2CH\langle$ | — | Colorless prism-like crystals | Ethanol-water | 180.5–182 | — |
| 109 | $-CH{=}C\langle$ | — | Light yellowish needle-like crystals | Ethanol-chloroform | 258–260 (decomp.) | — |

TABLE 6-continued

| | | | | | | |
|---|---|---|---|---|---|---|
| 110 | $-CH_2CH<$ | — | White powdery product | Ethanol | 212.5–214 (decomp.) | — |
| 111 | $-CH_2CH<$ | — | White powdery product | Ethanol-water | 227.5–229 (decomp.) | — |
| 112 | $-CH_2CH<$ | — | White powdery product | Dimethyl-formamide-water | 254–256 (decomp.) | $\frac{1}{2}H_2O$ |
| 113 | $-CH_2CH<$ | — | White powdery product | Ethanol-water | 293.5–294.5 (decomp.) | $\frac{1}{4}H_2O$ |
| 114 | $-CH_2CH<$ | — | White powdery product | Ethanol-water | 279–280 (decomp.) | $\frac{1}{2}H_2O$ |
| 115 | $-CH_2CH<$ | — | White powdery product | Ethanol-water | 284–285.5 (decomp.) | $\frac{3}{8}H_2O$ |
| 116 | $-CH_2CH<$ | — | White powdery product | Ethano-water | 276–277 (decomp.) | $\frac{1}{2}H_2O$ |
| 117 | $-CH_2CH<$ | — | White granular crystals | Ethanol | 202.5–294.5 | — |
| 118 | $-CH_2CH<$ | — | White powdery product | Ethanol-chloroform | 256–257.5 (decomp.) | — |

TABLE 6-continued

| | | | | | | |
|---|---|---|---|---|---|---|
| 119 | $-CH_2CH$ | — | White powdery product | Ethanol | 217–220 (decomp.) | — |
| 120 | $-CH_2CH$ | — | Light yellowish prism-like crystals | Ethanol- | 261–262 (decomp.) | — |
| 121 | $-CH_2CH$ | — | Light brownish powdery product | Dimethyl-formamide-water | 315.5–318 (decomp.) | $\frac{1}{2}H_2O$ |
| 122 | $-CH_2CH$ | — | White powdery product | Ethanol-water | 294–295 (decomp.) | — |
| 123 | $-CH_2CH$ | — | White powdery product | Ethanol-water | 278–280 (decomp.) | — |
| 124 | $-CH_2CH$ | — | White powdery product | Ethanol-water | 302–303 (decomp.) | — |
| 125 | $-CH_2CH$ | $-CH_2CH_2-$ | White powdery product | Dimethyl-formamide-water | 279.5–280.5 (decomp.) | — |
| 126 | $-CH_2CH$ | $CH_2$ | White powdery product | Dimethyl-formamide-water | 295–296 (decomp.) | — |

(*cbz: $-COOCH_2-$ 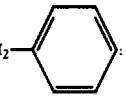 : carboxybenzyl)

(++)NMR δ (DMSO); 1.17 (3H, t), 3.00–3.70 (2H, m), 4.18 (2H, q, J = 7Hz), 4.50–5.80 (1H, m), 6.53 (1H, s), 7.10–8.00 (8H, m), 8.88 (1H, d, J = 7.5Hz).

EXAMPLES 127–220
By a method similar to that described in Example 3, by using a suitable starting material, there were prepared compounds as shown in Table 7 as follows.
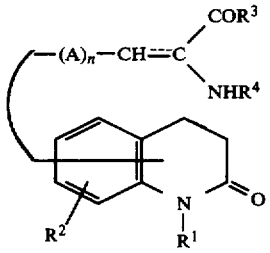

TABLE 7
| Example | $R^1$ | $R^2$ | $R^3$ | $R^4$ | Substituted position of the side-chain of $-(A)_n-CH-C(COR^3)(NHR^4)$ | Carbon-carbon bond between 3- and 4-position |
|---|---|---|---|---|---|---|
| 127 | H | H | OH | $COCH_3$ | 3 | Double bond |
| 128 | H | H | OH | $COC_2H_5$ | 3 | Double bond |
| 129 | H | H | OH | 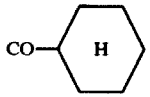 | 3 | Double bond |
| 130 | H | H | OH | 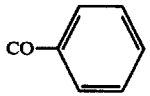 | 3 | Double bond |
| 131 | H | H | OH | 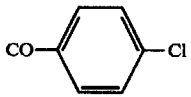 | 3 | Single bond |
| 132 | H | H | OH | $CO(CH_2)_2NHcbz$* | 3 | Double bond |
| 133 | H | H | OH | $CO(CH_2)_2NH_2$ | | |
| 134 | $CH_3$ | H | OH | 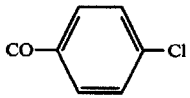 | 3 | Double bond |
| 135 | H | H | OH | 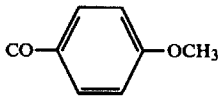 | 3 | Double bond |
| 136 | H | H | OH | 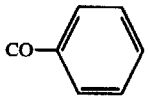 | 4 | Double bond |

TABLE 7-continued
| | | | | | | |
|---|---|---|---|---|---|---|
| 137 | H | H | OH | 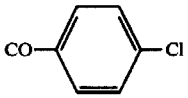 | 4 | Double bond |
| 138 | H | H | $OCH_3$ | 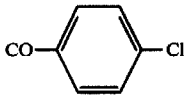 | 4 | Double bond |
| 139 | H | H | OH | $CO(CH_2)_2NH.cbz^*$ | 4 | Double bond |
| 140 | H | H | OH | $CO(CH_2)_2NH_2$ | 4 | Double bond |
| 141 | H | H | OH | 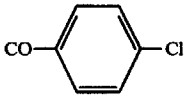 | 4 | Single bond |
| 142 | H | H | OH | 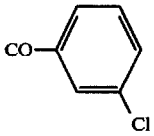 | 4 | Double bond |
| 143 | H | H | OH | 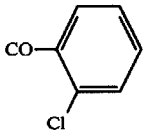 | 4 | Double bond |
| 144 | H | H | OH | 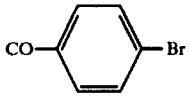 | 4 | Double bond |
| 145 | H | H | OH | 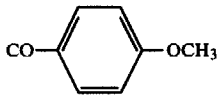 | 4 | Double bond |

TABLE 7-continued
| | | | | | | |
|---|---|---|---|---|---|---|
| 146 | H | H | OH | 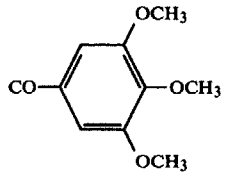 | 4 | Double bond |
| 147 | H | H | OH | 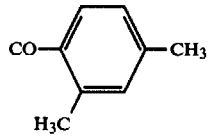 | 4 | Double bond |
| 148 | H | H | OH | 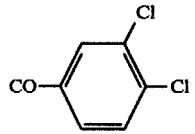 | 4 | Double bond |
| 149 | H | H | OH | 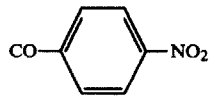 | 4 | Double bond |
| 150 | H | H | OH | 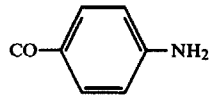 | 4 | Double bond |
| 151 | $CH_3$ | H | OH | 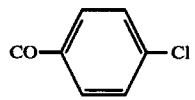 | 4 | Double bond |
| 152 | $C_2H_5$ | H | OH | 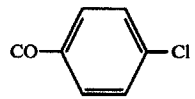 | 4 | Double bond |
| 153 | $-CH_2CH{=}CH_2$ | H | OH | 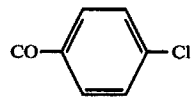 | 4 | Double bond |

TABLE 7-continued

| | | | | | | |
|---|---|---|---|---|---|---|
| 154 | $-CH_2C{\equiv}CH$ | H | OH | 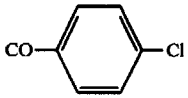 | 4 | Double bond |
| 155 | 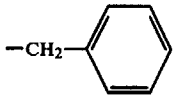 | H | OH | 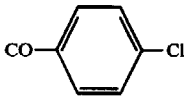 | 4 | Double bond |
| 156 | H | H | OH | 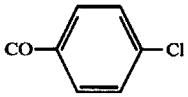 | 5 | Double bond |
| 157 | H | 8-$OCH_3$ | OH | 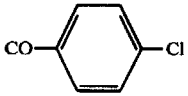 | 5 | Double bond |
| 158 | H | 8-OH | OH | 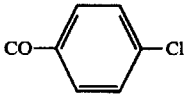 | 5 | Double bond |
| 159 | H | H | OH | 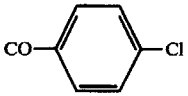 | 6 | Single bond |
| 160 | H | H | OH | H | 3 | Double bond |
| 161 | $CH_3$ | H | OH | H | 3 | Double bond |
| 162 | H | 6-$OCH_3$ | OH | H | 3 | Double bond |
| 163 | H | 6-OH | OH | H | 3 | Double bond |
| 164 | H | H | OH | H | 4 | Single bond |
| 165 | H | H | OH | H | 4 | Double bond |
| 166 | $CH_3$ | H | OH | H | 4 | Double bond |
| 167 | $C_2H_5$ | H | OH | H | 4 | Double bond |
| 168 | $-CH_2CH{=}CH_2$ | H | OH | H | 4 | Double bond |
| 169 | $-CH_2C{\equiv}CH$ | H | OH | H | 4 | Double bond |
| 170 | 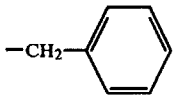 | H | OH | H | 4 | Double bond |

TABLE 7-continued
| | | | | | | |
|---|---|---|---|---|---|---|
| 171 | H | H | OH | H | 5 | Double bond |
| 172 | H | 8-$OCH_3$ | OH | H | 5 | Double bond |
| 173 | H | 8-OH | OH | H | 5 | Double bond |
| 174 | H | H | OH | H | 6 | Single bond |
| 175 | H | 8-$OCH_3$ | OH | $COCH_3$ | 5 | Double bond |
| 176 | H | H | OH | 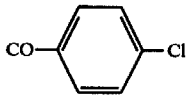 | 3 | Double bond |
| 177 | H | 6-OH | OH | 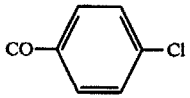 | 3 | Double bond |
| 178 | H | H | OH | H | 3 | Single bond |
| 179 | H | H | OH | 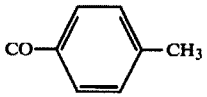 | 4 | Double bond |
| 180 | H | H | OH | 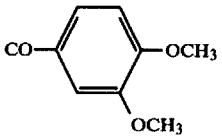 | 3 | Double bond |
| 181 | H | H | $OC_2H_5$ | 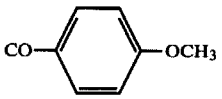 | 3 | Double bond |
| 182 | H | H | OH | 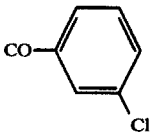 | 3 | Double bond |

TABLE 7-continued
| | | | | | | |
|---|---|---|---|---|---|---|
| 183 | H | H | OH | 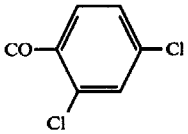 | 4 | Double bond |
| 184 | H | H | OH | 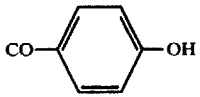 | 4 | Double bond |
| 185 | H | H | OH | 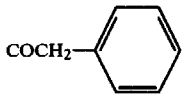 | 4 | Double bond |
| 186 | H | 8-$CH_3$ | OH | 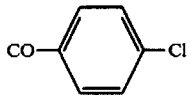 | 4 | Double bond |
| 187 | H | H | OH | 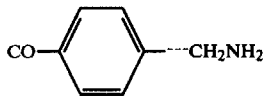 | 4 | Double bond |
| 188 | H | H | OH | 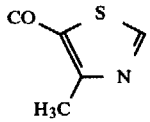 | 4 | Double bond |
| 189 | H | H | OH | 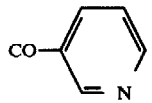 | 4 | Double bond |
| 190 | H | H | OH | 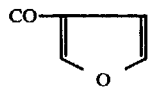 | 4 | Double bond |

TABLE 7-continued
| | | | | | | |
|---|---|---|---|---|---|---|
| 191 | H | H | OH | 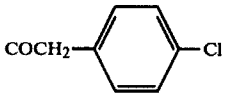 | 4 | Double bond |
| 192 | $CH_3$ | H | OH | 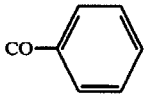 | 3 | Double bond |
| 193 | $C_2H_5$ | H | OH | 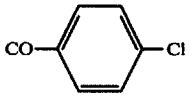 | 3 | Double bond |
| 194 | $C_2H_5$ | H | OH | 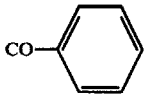 | 4 | Double bond |
| 195 | H | H | $NH_2$ | 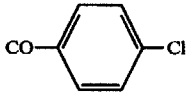 | 4 | Double bond |
| 196 | H | H | 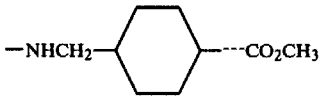 | 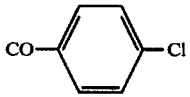 | 4 | Double bond |
| 197 | H | H | 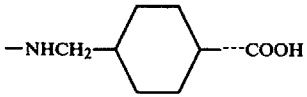 | 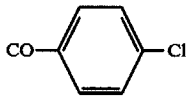 | 4 | Double bond |
| 198 | $CH_3$ | H | OH | $COCH_3$ | 3 | Double bond |
| 199 | H | H | OH | 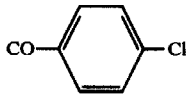 | 3 | Double bond |

TABLE 7-continued
| | | | | | | |
|---|---|---|---|---|---|---|
| 200 | $C_2H_5$ | H | OH | 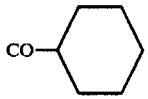 | 4 | Double bond |
| 201 | $C_2H_5$ | H | OH | 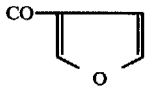 | 4 | Double bond |
| 202 | n-$C_4H_9$ | H | OH | 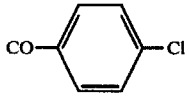 | 4 | Double bond |
| 203 | $CH_3$ | H | OH | 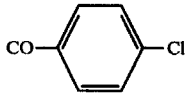 | 3 | Double bond |
| 204 | $C_2H_5$ | H | OH | 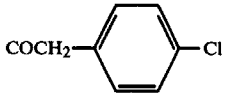 | 4 | Double bond |
| 205 | $CH_3$ | H | OH | 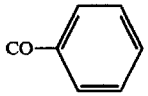 | 4 | Double bond |
| 206 | H | H | OH | 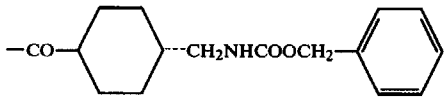 | 4 | Double bond |
| 207 | H | H | OH | 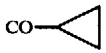 | 4 | Double bond |
| 208 | H | H | OH | 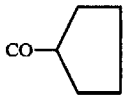 | 4 | Double bond |

TABLE 7-continued
| | | | | | | |
|---|---|---|---|---|---|---|
| 209 | H | H | OH | 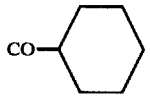 | 4 | Double bond |
| 210 | H | H | OH | 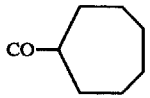 | 4 | Double bond |
| 211 | H | H | $OCH_2COOCH_3$ | 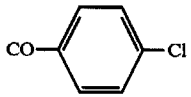 | 4 | Double bond |
| 212 | H | H | $OCH_2CO$ | 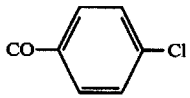 | 4 | Double bond |
| 213 | H | H | $OCH_2OC(=O)C(CH_3)_3$ | 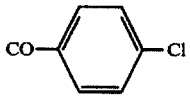 | 4 | Double bond |
| 214 | H | 8-Cl | OH | 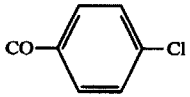 | 4 | Double bond |
| 215 | H | 6-OH | OH | 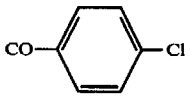 | 4 | Double bond |
| 216 | H | 6-$OCH_3$ | OH | 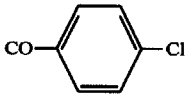 | 4 | Double bond |
| 217 | H | 8-$C_2H_5$ | OH | 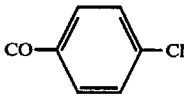 | 4 | Double bond |

TABLE 7-continued

| | | | | | | |
|---|---|---|---|---|---|---|
| 218 | H | 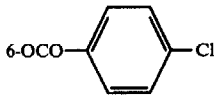 | OH | 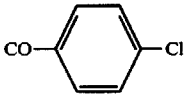 | 4 | Double bond |
| 219 | H | H | OH | 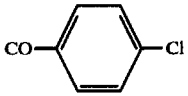 | 4 | Double bond |
| 220 | H | H | OH | 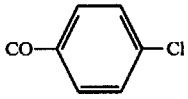 | 4 | Double bond |

| Example | $-CH-C<$ | $(A)_n$ | Crystal form | Recrystallization solvent | Melting point (°C.) | Type of the salt |
|---|---|---|---|---|---|---|
| 127 | $-CH_2CH<$ | — | Light yellowish product | Water | 228–231 (decomp.) | — |
| 128 | $-CH_2CH<$ | — | White powdery product | Water | 212–215 (decomp.) | — |
| 129 | $-CH_2CH<$ | — | White powdery product | Methanol | 261–264 (decomp.) | — |
| 130 | $-CH_2CH<$ | — | White powdery product | Ethanol | 255–257.5 (decomp.) | — |
| 131 | $-CH_2CH<$ | — | Colorless prism-like crystals | Ethyl acetate-hexane | 201.5–203.5 | — |

TABLE 7-continued

| | | | | | | |
|---|---|---|---|---|---|---|
| 132 | $-CH_2CH\langle$ | — | White powdery product | Ethanol-ether | 190–192 (decomp.) | — |
| 133 | $-CH_2CH\langle$ | — | White powdery product | Methanol | 250–253 (decomp.) | — |
| 134 | $-CH_2CH\langle$ | — | White powdery product | Ethanol | 246–247.5 (decomp.) | — |
| 135 | $-CH_2CH\langle$ | — | White powdery product | Ethanol | 249–251 (decomp.) | — |
| 136 | $-CH_2CH\langle$ | — | Colorless prism-like crystals | Ethanol | 280–282 (decomp.) | $H_2O$ |
| 137 | $-CH_2CH\langle$ | — | White powdery product | Methanol-chloroform | 288–290 (decomp.) | $\frac{1}{2}H_2O$ |
| 138 | $-CH_2CH\langle$ | — | Colorless needle-like crystals | Methanol-chloroform | 275–276.5 (decomp.) | $\frac{1}{2}H_2O$ |
| 139 | $-CH_2CH\langle$ | — | White cotton-like crystals | Methanol chloroform | 250–252 (decomp.) | $\frac{1}{2}H_2O$ |
| 140 | $-CH_2CH\langle$ | — | White powdery product | Methanol | 270–271 (decomp.) | $HBr.\frac{1}{2}H_2O$ |

TABLE 7-continued

| | | | | | | |
|---|---|---|---|---|---|---|
| 141 | $-CH_2CH\langle$ | — | White powdery product | Methanol-water | 256–257 (decomp.) | — |
| 142 | $-CH_2CH\langle$ | — | Colorless needle-like crystals | Methanol-water | 265–267 (decomp.) | — |
| 143 | $-CH_2CH\langle$ | — | White powdery product | Methanol-water | 270.5–271.5 (decomp.) | $\frac{1}{4}H_2O$ |
| 144 | $-CH_2CH\langle$ | — | White powdery | Dimethylformamide-water | 287–288.5 (decomp.) | $\frac{1}{2}H_2O$ |
| 145 | $-CH_2CH\langle$ | — | White powdery product | Acetone-water | 259–261 (decomp.) | — |
| 146 | $-CH_2CH\langle$ | — | White powdery product | Methanol | 256–258 (decomp.) | — |
| 147 | $-CH_2CH\langle$ | — | White powdery product | Dimethylformamide-water | 287–289 (decomp.) | $\frac{1}{2}H_2O$ |
| 148 | $-CH_2CH\langle$ | — | White powdery product | Dimethylformamide-water | 287–280 (decomp.) | — |
| 149 | $-CH_2CH\langle$ | — | White powdery product | Dimethylformamide-water | 290–291 (decomp.) | — |

TABLE 7-continued

| | | | | | | |
|---|---|---|---|---|---|---|
| 150 | $-CH_2CH\langle$ | — | White powdery product | Dimethylformamide-water | 240–242 (decomp.) | — |
| 151 | $-CH_2CH\langle$ | — | Colorless needle-like crystals | Ethanol | 247–249 (decomp.) | — |
| 152 | $-CH_2CH\langle$ | — | Colorless prism-like crystals | Ethanol | 134–138 | $\frac{1}{2}H_2O$ (+++) |
| 153 | $-CH_2CH\langle$ | — | Light yellowish powdery product | Ethyl acetate | 130–135 | — |
| 154 | $-CH_2CH\langle$ | — | Colorless needle-like crystals | Methanol-water | 271–272 (decomp.) | $H_2O$ |
| 155 | $-CH_2CH\langle$ | — | White powdery product | Methanol-water | 230–231 (decomp.) | $H_2O$ |
| 156 | $-CH_2CH\langle$ | — | Colorless needle-like crystals | Dimethylformamide-water | Over 300 | — |
| 157 | $-CH_2CH\langle$ | — | Light yellowish powdery product | Dimethylformamide-water | 299–300 (decomp.) | — |
| 158 | $-CH_2CH\langle$ | — | Colorless powdery product | Dimethylformamide-water | Over 300 | — |

TABLE 7-continued

| | | | | | | |
|---|---|---|---|---|---|---|
| 159 | $-CH_2CH<$ | — | Colorless powdery product | Ethanol | 251-252 (decomp.) | — |
| 160 | $-CH_2CH<$ | — | White powdery product | Methanol-acetone | 271-272 (decomp.) | HCl |
| 161 | $-CH_2CH<$ | — | White granular products | Ethanol | 218-225 (decomp.) | HCl |
| 162 | $-CH_2CH<$ | — | Colorless powdery product | Water | 293-295 (decomp.) | $HCl.\frac{1}{2}H_2O$ |
| 163 | $-CH_2CH<$ | — | Yellowish powdery product | Water | Over 300 | HBr |
| 164 | $-CH_2CH<$ | — | Colorless powdery product | Ethanol-ether | 237-238 (decomp.) | $HCl.\frac{1}{4}H_2O$ |
| 165 | $-CH_2CH<$ | — | Colorless prism-like crystals | Ethanol-water | 220-225 (decomp.) | $HCl.H_2O$ |
| 166 | $-CH_2CH<$ | — | Colorless prism-like crystals | Ethanol | 175-178 (decomp.) | $HCl.H_2O$ |
| 167 | $-CH_2CH<$ | — | White powder product | Methanol | 255-260 (decomp.) | HCl |

TABLE 7-continued

| | | | | | | |
|---|---|---|---|---|---|---|
| 168 | $-CH_2CH\langle$ | — | Colorless prism-like crystals | Ethanol | 166–171 (decomp.) | $HCl.H_2O$ |
| 169 | $-CH_2CH\langle$ | — | White powdery product | Methanol | 218–221 (decomp.) | $H_2O$ |
| 170 | $-CH_2CH\langle$ | — | White powdery product | Ethanol | 166–169 (decomp.) | HCl |
| 171 | $-CH_2CH\langle$ | — | Colorless powdery product | Water | Over 300 | HCl |
| 172 | $-CH_2CH\langle$ | — | Colorless powdery product | Water | 257–260 (decomp.) | $HCl.H_2O$ |
| 173 | $-CH_2CH\langle$ | — | Colorless powdery product | Methanol-ether | 290–292 (decomp.) | $HBr.\frac{1}{2}H_2O$ |
| 174 | $-CH_2CH\langle$ | — | Colorless granular crystals | Methanol-ether | 283–285 (decomp.) | HCl |
| 175 | $-CH{=}C\langle$ | — | Colorless needle-like crystals | Ethanol | 264–265 (decomp.) | $\frac{1}{2}H_2O$ |
| 176 | $-CH_2CH\langle$ | — | White powdery product | Ethanol-water | 270–271.5 (decomp.) | — |

TABLE 7-continued

| | | | | | | |
|---|---|---|---|---|---|---|
| 177 | $-CH_2CH<$ | — | Light yellowish powdery product | Methanol-water | 223–227 (decomp.) | — |
| 178 | $-CH_2CH<$ | — | White powdery product | Ethanol | 208–210 (decomp.) | HCl |
| 179 | $-CH_2CH<$ | — | White powdery product | Ethanol-water | 284–286 (decomp.) | $\frac{1}{2}H_2O$ |
| 180 | $-CH_2CH<$ | — | White powdery product | Ethanol-water | 200–205 (decomp.) | $\frac{1}{4}H_2O$ |
| 181 | $-CH_2CH<$ | — | White powdery product | Ethyl acetate-ethanol | 206–208.5 (decomp.) | — |
| 182 | $-CH_2CH<$ | — | Light yellowish powdery product | Dimethylformamide-water | 278–279 (decomp.) | — |
| 183 | $-CH_2CH<$ | — | White powdery product | Water | 281–282 (decomp.) | — |
| 184 | $-CH_2CH<$ | — | White powdery product | Ethanol | 305.5–306.5 (decomp.) | $\frac{3}{2}H_2O$ |
| 185 | $-CH_2CH<$ | — | Light yellowish powdery product | Ethanol | 271.5–272.5 (decomp.) | $H_2O$ |

TABLE 7-continued

| | | | | | | |
|---|---|---|---|---|---|---|
| 186 | $-CH_2CH\langle$ | — | Light yellowish powdery product | Dimethylformamide-water | 278–279 (decomp.) | — |
| 187 | $-CH_2CH\langle$ | — | White powdery product | Water | 320 (decomp.) | — |
| 188 | $-CH_2CH\langle$ | — | White powdery product | Methanol | 261–263 (decomp.) | $\frac{1}{2}H_2O$ |
| 189 | $-CH_2CH\langle$ | — | White powdery product | Ethanol | 298–299 (decomp.) | $\frac{1}{2}H_2O$ |
| 190 | $-CH_2CH\langle$ | — | White powdery product | Ethanol-water | 283–286 (decomp.) | $\frac{1}{2}H_2O$ |
| 191 | $-CH_2CH\langle$ | — | White powdery product | Ethanol-water | 280.5–282.5 (decomp.) | $H_2O$ |
| 192 | $-CH_2CH\langle$ | — | Light yellowish powdery product | Ethanol | 234.5–236 (decomp.) | — |
| 193 | $-CH_2CH\langle$ | — | White powdery product | Ethanol | 208–211 | — |
| 194 | $-CH_2CH\langle$ | — | White powdery product | Ethanol | 226–228 (decomp.) | — |

TABLE 7-continued

| | | | | | | |
|---|---|---|---|---|---|---|
| 195 | $-CH_2CH\langle$ | — | Light yellowish powdery product | Dimethylformamide-water | Over 300 | — |
| 196 | $-CH_2CH\langle$ | — | White powdery product | Dimethylformamide-water | 298–299 (decomp.) | — |
| 197 | $-CH_2CH\langle$ | — | White powdery product | Dimethylformamide-water | 303–305 (decomp.) | — |
| 198 | $-CH{=}C\langle$ | — | Yellow-brownish powdery product | Ethanol-chloroform | 241.5–242.5 (decomp.) | — |
| 199 | $-CH{=}C\langle$ | — | White powdery product | Ethanol-water | 275–280 (decomp.) | $\frac{1}{3}H_2O$ |
| 200 | $-CH_2CH\langle$ | — | Colorless needle-like crystals | Ethanol-water | 220.5–222 (decomp.) | — |
| 201 | $-CH_2CH\langle$ | — | White powdery product | Ethyl acetate-hexane | 135–137 (decomp.) | $\frac{1}{3}H_2O$ |
| 202 | $-CH_2CH\langle$ | — | Colorless prism-like crystals | Ethanol-water | 180.5–182 | — |
| 203 | $-CH{=}C\langle$ | — | Light yellowish needle-like crystals | Ethanol-chloroform | 258–260 (decomp.) | — |

TABLE 7-continued

| | | | | | | |
|---|---|---|---|---|---|---|
| 204 | $-CH_2CH<$ | — | White powdery product | Ethanol | 212.5–214 (decomp.) | — |
| 205 | $-CH_2CH<$ | — | White powdery product | Ethanol-water | 227.5–229 (decomp.) | — |
| 206 | $-CH_2CH<$ | — | White powdery product | Dimethylformamide-water | 254–256 (decomp.) | $\frac{1}{3}H_2O$ |
| 207 | $-CH_2CH<$ | — | White powdery product | Ethanol-water | 293.5–294.5 (decomp.) | $\frac{1}{3}H_2O$ |
| 208 | $-CH_2CH<$ | — | White powdery product | Ethanol-water | 279–280 (decomp.) | $\frac{1}{3}H_2O$ |
| 209 | $-CH_2CH<$ | — | White powdery product | Ethanol-water | 284–285.5 (decomp.) | $\frac{1}{3}H_2O$ |
| 210 | $-CH_2CH<$ | — | White powdery product | Ethano-water | 276–277 (decomp.) | $\frac{1}{3}H_2O$ |
| 211 | $-CH_2CH<$ | — | White granular crystals | Ethanol | 202.5–294.5 | — |
| 212 | $-CH_2CH<$ | — | White powdery product | Ethanol-chloroform | 256–257.5 (decomp.) | — |

TABLE 7-continued

| | | | | | | |
|---|---|---|---|---|---|---|
| 213 | $-CH_2CH\diagup\diagdown$ | — | White powdery product | Ethanol | 217–220 (decomp.) | — |
| 214 | $-CH_2CH\diagup\diagdown$ | — | Light yellowish prism-like crystals | Ethanol- | 261–262 (decomp.) | — |
| 215 | $-CH_2CH\diagup\diagdown$ | — | Light brownish powdery product | Dimethylformamide-water | 315.5–318 (decomp.) | $\frac{1}{2}H_2O$ |
| 216 | $-CH_2CH\diagup\diagdown$ | — | White powdery product | Ethanol-water | 294–295 (decomp.) | — |
| 217 | $-CH_2CH\diagup\diagdown$ | — | White powdery product | Ethanol-water | 278–280 (decomp.) | — |
| 218 | $-CH_2CH\diagup\diagdown$ | — | White powdery product | Ethanol-water | 302–303 (decomp.) | — |
| 219 | $-CH_2CH\diagup\diagdown$ | $CH_2CH_2$ | White powdery product | Dimethylformamide-water | 279.5–280.5 (decomp.) | — |
| 220 | $-CH_2CH\diagup\diagdown$ | $CH_2$ | White powdery product | Dimethylformamide-water | 295–296 (decomp.) | — |

(*cbz: $-COOCH_2-$ 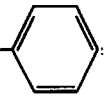 : carboxybenzyl)

(+++) NMR δ(DMSO); 1.17 (3H, t), 3.00–3.70 (2H, m), 4.18 (2H, q. J = 7Hz), 4.50–5.80 (1H, m), 6.53 (1H, s), 7.10–8.00 (8H, m), 8.88 (1H, d, J = 7.5Hz).

EXAMPLES 221-314
By a method similar to that described in Example 4, by using a suitable starting material, there were prepared as shown in Table 8 as follows.
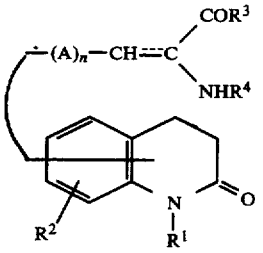

TABLE 8
| Example | $R^1$ | $R^2$ | $R^3$ | $R^4$ | Substituted position of the side-chain of $-(A)_n-CH-C(COR^3)(NHR^4)$ | Carbon-carbon bond between 3- and 4-position |
|---|---|---|---|---|---|---|
| 221 | H | H | OH | $COCH_3$ | 3 | Double bond |
| 222 | H | H | OH | $COC_2H_5$ | 3 | Double bond |
| 223 | H | H | OH | 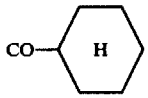 | 3 | Double bond |
| 224 | H | H | OH | 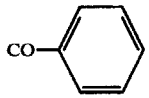 | 3 | Double bond |
| 225 | H | H | OH | 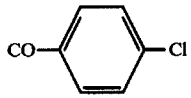 | 3 | Single bond |
| 226 | H | H | OH | $CO(CH_2)_2NHcbz$* | 3 | Double bond |
| 227 | H | H | OH | $CO(CH_2)_2NH_2$ | 3 | Double bond |
| 228 | $CH_3$ | H | OH | 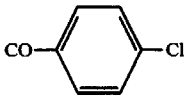 | 3 | Double bond |
| 229 | H | H | OH | 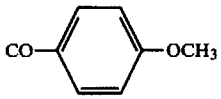 | 3 | Double bond |
| 230 | H | H | OH | 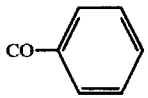 | 4 | Double bond |

TABLE 8-continued
| | | | | | | |
|---|---|---|---|---|---|---|
| 231 | H | H | OH | 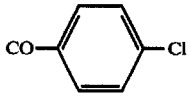 | 4 | Double bond |
| 232 | H | H | $OCH_3$ | 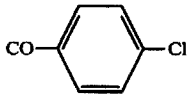 | 4 | Double bond |
| 233 | H | H | OH | $CO(CH_2)_2NH.cbz^*$ | 4 | Double bond |
| 234 | H | H | OH | $CO(CH_2)_2NH_2$ | 4 | Double bond |
| 235 | H | H | OH | 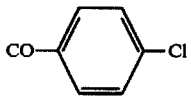 | 4 | Single bond |
| 236 | H | H | OH | 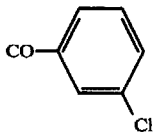 | 4 | Double bond |
| 237 | H | H | OH | 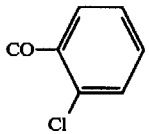 | 4 | Double bond |
| 238 | H | H | OH | 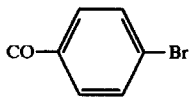 | 4 | Double bond |
| 239 | H | H | OH | 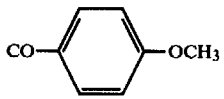 | 4 | Double bond |

TABLE 8-continued
| | | | | | | |
|---|---|---|---|---|---|---|
| 240 | H | H | OH | 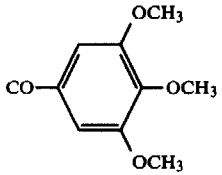 | 4 | Double bond |
| 241 | H | H | OH | 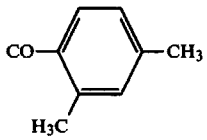 | 4 | Double bond |
| 242 | H | H | OH | 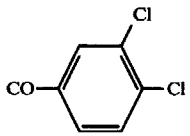 | 4 | Double bond |
| 243 | H | H | OH | 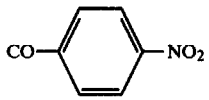 | 4 | Double bond |
| 244 | H | H | OH | 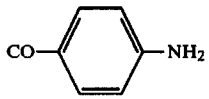 | 4 | Double bond |
| 245 | $CH_3$ | H | OH | 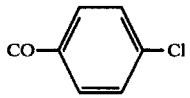 | 4 | Double bond |
| 246 | $C_2H_5$ | H | OH | 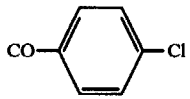 | 4 | Double bond |
| 247 | $-CH_2CH{=}CH_2$ | H | OH | 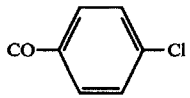 | 4 | Double bond |

TABLE 8-continued

| | | | | | | |
|---|---|---|---|---|---|---|
| 248 | $-CH_2C{\equiv}CH$ | H | OH | 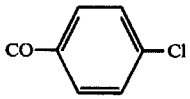 | 4 | Double bond |
| 249 | 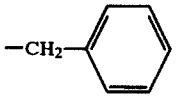 | H | OH | 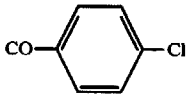 | 4 | Double bond |
| 250 | H | H | OH | 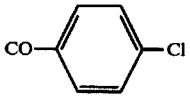 | 5 | Double bond |
| 251 | H | 8-$OCH_3$ | OH | 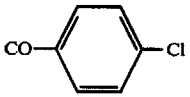 | 5 | Double bond |
| 252 | H | 8-OH | OH | 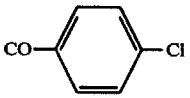 | 5 | Double bond |
| 253 | H | H | OH | 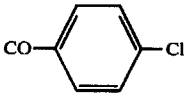 | 6 | Single bond |
| 254 | H | H | OH | H | 3 | Double bond |
| 255 | $CH_3$ | H | OH | H | 3 | Double bond |
| 256 | H | 6-$OCH_3$ | OH | H | 3 | Double bond |
| 257 | H | 6-OH | OH | H | 3 | Double bond |
| 258 | H | H | OH | H | 4 | Single bond |
| 259 | H | H | OH | H | 4 | Double bond |
| 260 | $CH_3$ | H | OH | H | 4 | Double bond |
| 261 | $C_2H_5$ | H | OH | H | 4 | Double bond |
| 262 | $-CH_2CH{=}CH_2$ | H | OH | H | 4 | Double bond |
| 263 | $-CH_2C{\equiv}CH$ | H | OH | H | 4 | Double bond |
| 264 | 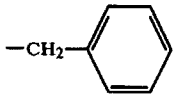 | H | OH | H | 4 | Double bond |

TABLE 8-continued
| | | | | | | |
|---|---|---|---|---|---|---|
| 265 | H | H | OH | H | 5 | Double bond |
| 266 | H | 8-$OCH_3$ | OH | H | 5 | Double bond |
| 267 | H | 8-OH | OH | H | 5 | Double bond |
| 268 | H | H | OH | H | 6 | Single bond |
| 269 | H | 8-$OCH_3$ | OH | $COCH_3$ | 5 | Double bond |
| 270 | H | 6-$OCH_3$ | OH | 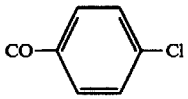 | 3 | Double bond |
| 271 | H | H | OH | 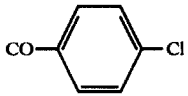 | 3 | Double bond |
| 272 | H | H | OH | H | 3 | Single bond |
| 273 | H | H | OH | 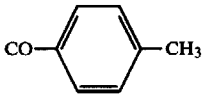 | 4 | Double bond |
| 274 | H | H | OH | 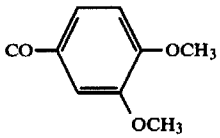 | 3 | Double bond |
| 275 | H | H | $OC_2H_5$ | 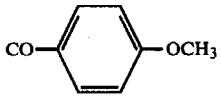 | 3 | Double bond |
| 276 | H | H | OH | 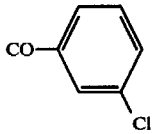 | 3 | Double bond |

TABLE 8-continued
| | | | | | | |
|---|---|---|---|---|---|---|
| 277 | H | H | OH | 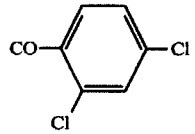 | 4 | Double bond |
| 278 | H | H | OH | 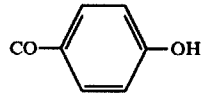 | 4 | Double bond |
| 279 | H | H | OH | 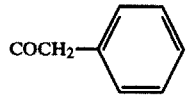 | 4 | Double bond |
| 280 | H | 8-$CH_3$ | OH | 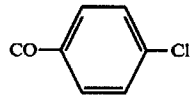 | 4 | Double bond |
| 281 | H | H | OH | 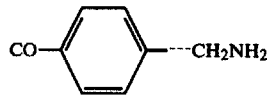 | 4 | Double bond |
| 282 | H | H | OH | 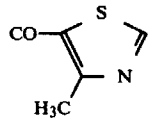 | 4 | Double bond |
| 283 | H | H | OH | 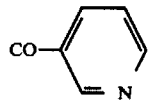 | 4 | Double bond |
| 284 | H | H | OH | 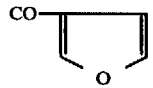 | 4 | Double bond |

TABLE 8-continued
| | | | | | | |
|---|---|---|---|---|---|---|
| 285 | H | H | OH | 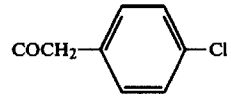 | 4 | Double bond |
| 286 | $CH_3$ | H | OH | 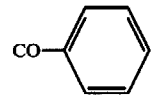 | 3 | Double bond |
| 287 | $C_2H_5$ | H | OH | 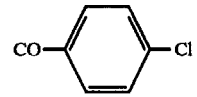 | 3 | Double bond |
| 288 | $C_2H_5$ | H | OH | 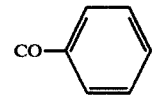 | 4 | Double bond |
| 289 | H | H | $NH_2$ | 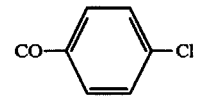 | 4 | Double bond |
| 290 | H | H | 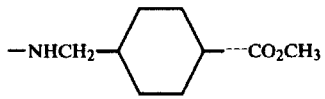 | 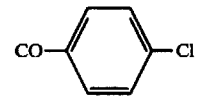 | 4 | Double bond |
| 291 | H | H | 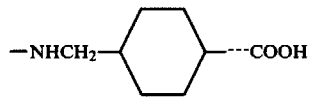 | 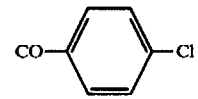 | 4 | Double bond |
| 292 | $CH_3$ | H | OH | $COCH_3$ | 3 | Double bond |
| 293 | H | H | OH | 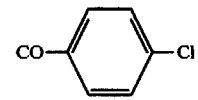 | 3 | Double bond |

TABLE 8-continued
| | | | | | | |
|---|---|---|---|---|---|---|
| 294 | $C_2H_5$ | H | OH | 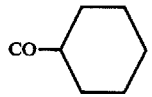 | 4 | Double bond |
| 295 | $C_2H_5$ | H | OH | 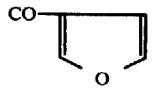 | 4 | Double bond |
| 296 | n-$C_4H_9$ | H | OH | 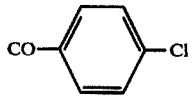 | 4 | Double bond |
| 297 | $CH_3$ | H | OH | 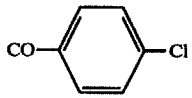 | 3 | Double bond |
| 298 | $C_2H_5$ | H | OH | 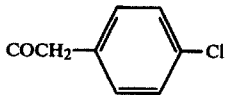 | 4 | Double bond |
| 299 | $CH_3$ | H | OH | 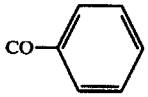 | 4 | Double bond |
| 300 | H | H | OH | 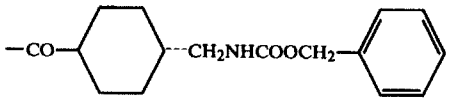 | 4 | Double bond |
| 301 | H | H | OH | 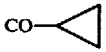 | 4 | Double bond |
| 302 | H | H | OH | 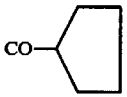 | 4 | Double bond |

TABLE 8-continued
| | | | | | | |
|---|---|---|---|---|---|---|
| 303 | H | H | OH | 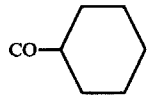 | 4 | Double bond |
| 304 | H | H | OH | 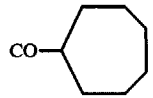 | 4 | Double bond |
| 305 | H | H | $OCH_2COOCH_3$ | 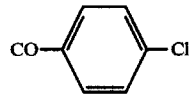 | 4 | Double bond |
| 306 | H | H | $OCH_2CO$ | 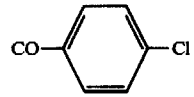 | 4 | Double bond |
| 307 | H | H | $OCH_2OC(=O)C(CH_3)_3$ | 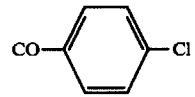 | 4 | Double bond |
| 308 | H | 8-Cl | OH | 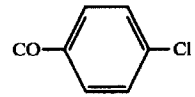 | 4 | Double bond |
| 309 | H | 6-OH | OH | 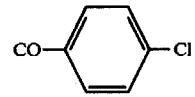 | 4 | Double bond |
| 310 | H | 6-$OCH_3$ | OH | 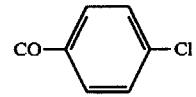 | 4 | Double bond |
| 311 | H | 8-$C_2H_5$ | OH | 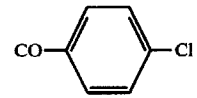 | 4 | Double bond |

TABLE 8-continued

| | | | | | | |
|---|---|---|---|---|---|---|
| 312 | H | 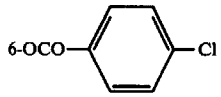 | OH | 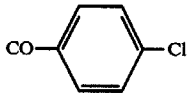 | 4 | Double bond |
| 313 | H | H | OH | 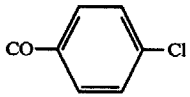 | 4 | Double bond |
| 314 | H | H | OH | 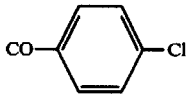 | 4 | Double bond |

| Example | $-CH-C\begin{matrix}/\\ \backslash\end{matrix}$ | $(A)_n$ | Crystal form | Recrystallization solvent | Melting point (°C.) | Type of the salt |
|---|---|---|---|---|---|---|
| 221 | $-CH_2CH\begin{matrix}/\\ \backslash\end{matrix}$ | — | Light yellowish product | Water | 228–231 (decomp.) | — |
| 222 | $-CH_2CH\begin{matrix}/\\ \backslash\end{matrix}$ | — | White powdery product | Water | 212–215 (decomp.) | — |
| 223 | $-CH_2CH\begin{matrix}/\\ \backslash\end{matrix}$ | — | White powdery product | Methanol | 261–264 (decomp.) | — |
| 224 | $-CH_2CH\begin{matrix}/\\ \backslash\end{matrix}$ | — | White powdery product | Ethanol | 255–257.5 (decomp.) | — |
| 225 | $-CH_2CH\begin{matrix}/\\ \backslash\end{matrix}$ | — | Colorless prism-like crystals | Ethyl acetate-hexane | 201.5–203.5 | — |

TABLE 8-continued

| | | | | | | |
|---|---|---|---|---|---|---|
| 226 | $-CH_2CH<$ | — | White powdery product | Ethanol-ether | 190–192 (decomp.) | — |
| 227 | $-CH_2CH<$ | — | White powdery product | Methanol | 250–253 (decomp.) | — |
| 228 | $-CH_2CH<$ | — | White powdery product | Ethanol | 246–247.5 (decomp.) | — |
| 229 | $-CH_2CH<$ | — | White powdery product | Ethanol | 249–251 (decomp.) | — |
| 230 | $-CH_2CH<$ | — | Colorless prism-like crystals | Ethanol | 280–282 (decomp.) | $H_2O$ |
| 231 | $-CH_2CH<$ | — | White powdery product | Methanol-chloroform | 288–290 (decomp.) | $\frac{1}{2}H_2O$ |
| 232 | $-CH_2CH<$ | — | Colorless needle-like crystals | Methanol-chloroform | 275–276.5 (decomp.) | $\frac{1}{2}H_2O$ |
| 233 | $-CH_2CH<$ | — | White cotton-like crystals | Methanol chloroform | 250–252 (decomp.) | $\frac{1}{2}H_2O$ |
| 234 | $-CH_2CH<$ | — | White powdery product | Methanol | 270–271 (decomp.) | $HBr.\frac{1}{2}H_2O$ |

TABLE 8-continued

| | | | | | | |
|---|---|---|---|---|---|---|
| 235 | $-CH_2CH<$ | — | White powdery product | Methanol-water | 256–257 (decomp.) | — |
| 236 | $-CH_2CH<$ | — | Colorless needle-like crystals | Methanol-water | 265–267 (decomp.) | — |
| 237 | $-CH_2CH<$ | — | White powdery product | Methanol-water | 270.5–271.5 (decomp.) | $\frac{1}{4}H_2O$ |
| 238 | $-CH_2CH<$ | — | White powdery | Dimethyl-formamide-water | 287–288.5 (decomp.) | $\frac{1}{2}H_2O$ |
| 239 | $-CH_2CH<$ | — | White powdery product | Acetone-water | 259–261 (decomp.) | — |
| 240 | $-CH_2CH<$ | — | White powdery product | Methanol | 256–258 (decomp.) | — |
| 241 | $-CH_2CH<$ | — | White powdery product | Dimethyl-formamide-water | 287–289 (decomp.) | $\frac{1}{2}H_2O$ |
| 242 | $-CH_2CH<$ | — | White powdery product | Dimethyl-formamide-water | 287–280 (decomp.) | — |
| 243 | $-CH_2CH<$ | — | White powdery product | Dimethyl-formamide-water | 290–291 (decomp.) | — |

TABLE 8-continued

| | | | | | | |
|---|---|---|---|---|---|---|
| 244 | $-CH_2CH<$ | — | White powdery product | Dimethyl-formamide-water | 240–242 (decomp.) | — |
| 245 | $-CH_2CH<$ | — | Colorless needle-like crystals | Ethanol | 247–249 (decomp.) | — |
| 246 | $-CH_2CH<$ | — | Colorless prism-like crystals | Ethanol | 134–138 | $\frac{1}{2}H_2O$(++++) |
| 247 | $-CH_2CH<$ | — | Light yellowish powdery product | Ethyl acetate | 130–135 | — |
| 248 | $-CH_2CH<$ | — | Colorless needle-like crystals | Methanol-water | 271–272 (decomp.) | $H_2O$ |
| 249 | $-CH_2CH<$ | — | White powdery product | Methanol-water | 230–231 (decomp.) | $H_2O$ |
| 250 | $-CH_2CH<$ | — | Colorless needle-like crystals | Dimethyl-formamide-water | Over 300 | — |
| 251 | $-CH_2CH<$ | — | Light yellowish powdery product | Dimethyl-formamide-water | 299–300 (decomp.) | — |
| 252 | $-CH_2CH<$ | — | Colorless powdery product | Dimethyl-formamide-water | Over 300 | — |

TABLE 8-continued

| | | | | | | |
|---|---|---|---|---|---|---|
| 253 | $-CH_2CH\begin{matrix}/\\ \backslash\end{matrix}$ | — | Colorless powdery product | Ethanol | 251–252 (decomp.) | — |
| 254 | $-CH_2CH\begin{matrix}/\\ \backslash\end{matrix}$ | — | White powdery product | Methanol-acetone | 271–272 (decomp.) | HCl |
| 255 | $-CH_2CH\begin{matrix}/\\ \backslash\end{matrix}$ | — | White granular products | Ethanol | 218–225 (decomp.) | HCl |
| 256 | $-CH_2CH\begin{matrix}/\\ \backslash\end{matrix}$ | — | Colorless powdery product | Water | 293–295 (decomp.) | $HCl.\frac{1}{2}H_2O$ |
| 257 | $-CH_2CH\begin{matrix}/\\ \backslash\end{matrix}$ | — | Yellowish powdery product | Water | Over 300 | HBr |
| 258 | $-CH_2CH\begin{matrix}/\\ \backslash\end{matrix}$ | — | Colorless powdery product | Ethanol-ether | 237–238 (decomp.) | $HCl.\frac{1}{4}H_2O$ |
| 259 | $-CH_2CH\begin{matrix}/\\ \backslash\end{matrix}$ | — | Colorless prism-like crystals | Ethanol-water | 220–225 (decomp.) | $HCl.H_2O$ |
| 260 | $-CH_2CH\begin{matrix}/\\ \backslash\end{matrix}$ | — | Colorless prism-like crystals | Ethanol | 175–178 (decomp.) | $HCl.H_2O$ |
| 261 | $-CH_2CH\begin{matrix}/\\ \backslash\end{matrix}$ | — | White powder product | Methanol | 255–260 (decomp.) | HCl |

TABLE 8-continued

| | | | | | | |
|---|---|---|---|---|---|---|
| 262 | $-CH_2CH<$ | — | Colorless prism-like crystals | Ethanol | 166–171 (decomp.) | $HCl.H_2O$ |
| 263 | $-CH_2CH<$ | — | White powdery product | Methanol | 218–221 (decomp.) | $H_2O$ |
| 264 | $-CH_2CH<$ | — | White powdery product | Ethanol | 166–169 (decomp.) | HCl |
| 265 | $-CH_2CH<$ | — | Colorless powdery product | Water | Over 300 | HCl |
| 266 | $-CH_2CH<$ | — | Colorless powdery product | Water | 257–260 (decomp.) | $HCl.H_2O$ |
| 267 | $-CH_2CH<$ | — | Colorless powdery product | Methanol-ether | 290–292 (decomp.) | $HBr.\frac{1}{2}H_2O$ |
| 268 | $-CH_2CH<$ | — | Colorless granular crystals | Methanol-ether | 283–285 (decomp.) | HCl |
| 269 | $-CH=C<$ | — | Colorless needle-like-crystals | Ethanol | 264–265 (decomp.) | $\frac{1}{2}H_2O$ |
| 270 | $-CH_2CH<$ | — | Yellowish powdery product | Methanol-water | 234.5–236 (decomp.) | — |

TABLE 8-continued

| | | | | | | |
|---|---|---|---|---|---|---|
| 271 | $-CH_2CH\begin{matrix}/\\ \backslash\end{matrix}$ | — | White powdery product | Ethanol-water | 270–271.5 (decomp.) | — |
| 272 | $-CH_2CH\begin{matrix}/\\ \backslash\end{matrix}$ | — | White powdery product | Ethanol | 208–210 (decomp.) | HCl |
| 273 | $-CH_2CH\begin{matrix}/\\ \backslash\end{matrix}$ | — | White powdery product | Ethanol-water | 284–286 (decomp.) | $\frac{1}{2}H_2O$ |
| 274 | $-CH_2CH\begin{matrix}/\\ \backslash\end{matrix}$ | — | White powdery product | Ethanol-water | 200–205 (decomp.) | $\frac{1}{4}H_2O$ |
| 275 | $-CH_2CH\begin{matrix}/\\ \backslash\end{matrix}$ | — | White powdery product | Ethyl acetate-ethanol | 206–208.5 (decomp.) | — |
| 276 | $-CH_2CH\begin{matrix}/\\ \backslash\end{matrix}$ | — | Light yellowish powdery product | Dimethyl-formamide-water | 278–279 (decomp.) | — |
| 277 | $-CH_2CH\begin{matrix}/\\ \backslash\end{matrix}$ | — | White powdery product | Water | 281–182 (decomp.) | — |
| 278 | $-CH_2CH\begin{matrix}/\\ \backslash\end{matrix}$ | — | White powdery product | Ethanol | 305.5–306.5 (decomp.) | $\frac{3}{2}H_2O$ |
| 279 | $-CH_2CH\begin{matrix}/\\ \backslash\end{matrix}$ | — | Light yellowish powdery product | Ethanol | 271.5–272.5 (decomp.) | $H_2O$ |

TABLE 8-continued

| | | | | | | |
|---|---|---|---|---|---|---|
| 280 | $-CH_2CH\langle$ | — | Light yellowish powdery product | Dimethyl-formamide-water | 278–279 (decomp.) | — |
| 281 | $-CH_2CH\langle$ | — | White powdery product | Water | 320 (decomp.) | — |
| 282 | $-CH_2CH\langle$ | — | White powdery product | Methanol | 261–263 (decomp.) | $\frac{1}{2}H_2O$ |
| 283 | $-CH_2CH\langle$ | — | White powdery product | Ethanol | 298–299 (decomp.) | $\frac{1}{2}H_2O$ |
| 284 | $-CH_2CH\langle$ | — | White powdery product | Ethanol-water | 283–286 (decomp.) | $\frac{1}{2}H_2O$ |
| 285 | $-CH_2CH\langle$ | — | White powdery product | Ethanol-water | 280.5–282.5 (decomp.) | $H_2O$ |
| 286 | $-CH_2CH\langle$ | — | Light yellowish powdery product | Ethanol | 234.5–236 (decomp.) | — |
| 287 | $-CH_2CH\langle$ | — | White powdery product | Ethanol | 208–211 | — |
| 288 | $-CH_2CH\langle$ | — | White powdery product | Ethanol | 226–228 (decomp.) | — |

TABLE 8-continued

| | | | | | | |
|---|---|---|---|---|---|---|
| 289 | $-CH_2CH\langle$ | — | Light yellowish powdery product | Dimethyl-formamide-water | Over 300 | — |
| 290 | $-CH_2CH\langle$ | — | White powdery product | Dimethyl-formamide-water | 298–299 (decomp.) | — |
| 291 | $-CH_2CH\langle$ | — | White powdery product | Dimethyl-formamide-water | 303–305 (decomp.) | — |
| 292 | $-CH{=}C\langle$ | — | Yellow-brownish powdery product | Ethanol-chloroform | 241.5–242.5 (decomp.) | — |
| 293 | $-CH{=}C\langle$ | — | White powdery product | Ethanol-water | 275–280 (decomp.) | $\frac{1}{2}H_2O$ |
| 294 | $-CH_2CH\langle$ | — | Colorless needle-like crystals | Ethanol-water | 220.5–222 (decomp.) | — |
| 295 | $-CH_2CH\langle$ | — | White powdery product | Ethyl acetate-hexane | 135–137 (decomp.) | $\frac{1}{2}H_2O$ |
| 296 | $-CH_2CH\langle$ | — | Colorless prism-like crystals | Ethanol-water | 180.5–182 | — |
| 297 | $-CH{=}C\langle$ | — | Light yellowish needle-like crystals | Ethanol-chloroform | 258–260 (decomp.) | — |

TABLE 8-continued

| | | | | | | |
|---|---|---|---|---|---|---|
| 298 | $-CH_2CH<$ | — | White powdery product | Ethanol | 212.5–214 (decomp.) | — |
| 299 | $-CH_2CH<$ | — | White powdery product | Ethanol-water | 227.5–229 (decomp.) | — |
| 300 | $-CH_2CH<$ | — | White powdery product | Dimethyl-formamide-water | 254–256 (decomp.) | $\frac{1}{2}H_2O$ |
| 301 | $-CH_2CH<$ | — | White powdery product | Ethanol-water | 293.5–294.5 (decomp.) | $\frac{1}{2}H_2O$ |
| 302 | $-CH_2CH<$ | — | White powdery product | Ethanol-water | 279–280 (decomp.) | $\frac{1}{2}H_2O$ |
| 303 | $-CH_2CH<$ | — | White powdery product | Ethanol-water | 284–285.5 (decomp.) | $\frac{1}{2}H_2O$ |
| 304 | $-CH_2CH<$ | — | White powdery product | Ethanol-water | 276–277 (decomp.) | $\frac{1}{2}H_2O$ |
| 305 | $-CH_2CH<$ | — | White granular crystals | Ethanol | 202.5–294.5 | — |
| 306 | $-CH_2CH<$ | — | White powdery product | Ethanol-chloroform | 256–257.5 (decomp.) | — |

TABLE 8-continued

| | | | | | | |
|---|---|---|---|---|---|---|
| 307 | $-CH_2CH\langle$ | — | White powdery product | Ethanol | 217–220 (decomp.) | — |
| 308 | $-CH_2CH\langle$ | — | Light yellowish prism-like crystals | Ethanol- | 261–262 (decomp.) | — |
| 309 | $-CH_2CH\langle$ | — | Light brownish powdery product | Dimethyl-formamide-water | 315.5–318 (decomp.) | $\frac{1}{2}H_2O$ |
| 310 | $-CH_2CH\langle$ | — | White powdery product | Ethanol-water | 294–295 (decomp.) | — |
| 311 | $-CH_2CH\langle$ | — | White powdery product | Ethanol-water | 278–280 (decomp.) | — |
| 312 | $-CH_2CH\langle$ | — | White powdery product | Ethanol-water | 302–303 (decomp.) | — |
| 313 | $-CH_2CH\langle$ | $CH_2CH_2$ | White powdery product | Dimethyl-formamide-water | 279.5–280.5 (decomp.) | — |
| 314 | $-CH_2CH\langle$ | $CH_2$ | White powdery product | Dimethyl-formamide-water | 295–296 (decomp.) | — |

(*cbz: $-COOCH_2-$ 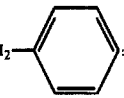 : carboxybenzyl)

(++++)NMR δ (DMSO); 1.17(3H, t), 3.00–3.70(2H, m), 4.18(2H, q. J = 7Hz), 4.50–5.80(1H, m), 6.53 (1H, s), 7.10–8.00(8H, m), 8.88(1H, d, J = 7.5Hz).

EXAMPLE 315

20 Grams of 5-formyl-8-methoxycarbostyril, 18 g of N-acetylgylcine, 7 g of anhydrous sodium acetate and 100 ml of acetic anhydride were mixed together by heating at 110° C. to form a homogeneous solution, further refluxed for 1.5 hours. After the reaction was completed, the reaction mixture was cooled, and cold water was added to the mixture, and the precipitated crystals were collected by filtration. The crystals were washed with cold water to obtain crude azlactone. In to a mixture of 100 ml of water and 300 ml of acetone, the crude azlactone was added then the whole mixture was refluxed for 5 hours. Acetone was removed by distillation, and to the residue thus obtained was added cold water to form crude crystals. The crude crystals thus obtained were collected by filtration. Then the crude crystals were dissolved in an aqueous solution of sodium hydrogencarbonate, and the insoluble matters were removed by filtration. The filtrate was treated with activated carbon, acidified with hydrochloric acid, then the precipitated crystals were collected by filtration, recrystallized from ethanol to obtain 10 g of 2-acetylamino-3-(8-methoxy-2-quinolon-5-yl)acrylic acid in the form of colorless needle-like crystals.

Melting point: 264°-265° C. (decomp.)

By a method similar to that described in Example 315, by using a suitable starting material, there werre prepared compounds of Example 104, 105 and 109.

EXAMPLE 316

To 6 g of 2-amino-3-(6-methoxy-2-quinolon-3-yl)propionic acid hydrochloride was added 60 ml of 47%-hydrobromic acid, and the mixture was refluxed for 7 hours. After the reaction mixture was cooled, the crystals precipitated were collected by filtration, then recrystallized from water to obtain 1.8 g of 2-amino-3-(6-hydroxy-2-quinolon-3-yl)proprionic acid hydrobromide in the form of yellowish powdery product.

Melting point: Over 300° C.

EXAMPLE 317

5 Grams of 2-amino-3-(2-quinolon-4-yl)propionic acid hydrochloride was dissolved in 150 ml of water. To this solution was added 1 g of 10%-palladium carbon, then hydrogen gas was adsorbed thereto at 70° C. under a normal pressure. The catalyst was removed from the reaction mixture by filtration, then the filtrate was concentrated under a reduced pressure. The residue thus obtained was crystallized by adding acetone, then recrystallized from ethanol-ether to obtain 3.6 g of 2-amino-3-(3,4-dihydroquinolin-2-on-4-yl)propionic acid hydrochloride in the form of white powdery product.

Melting point: 237°-283° C. (decomp.)

EXAMPLE 318

4 Grams of 2-amino-3-(2-quinolon-4-yl)propionic acid hydrochloride was suspended in 50 ml of methanol. Under an ice-cooled condition with strring, 5.3 g of thionyl chloride was added dropwise thereto, the reaction mixture was stirred at a room temperature overnight. Methanol and thionyl chloride were removed by distillation under a reduced pressure, then the residue obtained was recrystallized from methanolacetone to obtain 2.4 g of methyl 2-amino-3-(2-quinolon-4-yl)propionate in the form of white powdery product.

Melting point: 208°-211° C. (decomp.)

EXAMPLE 319

1.8 Grams of 2-(4-methoxybenzoyl)amino-3-(2-quinolon-3yl)propionic acid was dissolved in 100 ml of ethanol, then to this solution was introduced and saturated with hydrogen chloride gas under an ice-cooled condition with stirring. The reaction mixture was then refluxed for 5 hours and after completion of the reaction, the solvent was removed by distillation under a reduced pressure, the residue obtained was recrystallized from ethyl acetate-ethanol to obtain 1.5 g of ethyl 2-(4-methoxybenzoyl)amino-3-(2-quinolon-3-yl)propionate in the form of white powder product.

Melting point: 206°-208.5° C.

By a method similar to that described in the abovementione Example 319 by using a suitable starting material, compounds of Examples 44 and 87 were obtained.

EXAMPLE 320

To 2.7 g of 2-acetylamino-3-(2-quinolon-4-yl)propionic acid was added 30 ml of 20%-hydrochloric acid and the mixture was refluxed for 3 hours. The reaction mixture was concentrated under a reduced pressure to dryness, the residue obtained was recrystallized from ethanol-water to obtain 1.9 g of 2-amino-3-(2-quinolon-4-yl)propionic acid hydrochloride hydrate in the form of colorless prism-like crystals.

Melting point: 220°-225° C. (decomp.)

By a method similar to that described in the abovementioned Example 320 using a suitable starting material, there were prepared compounds of Examples 9-32.

EXAMPLE 321

6 Grams of 2-amino-3-(8-methoxy-2-quinolon-5-yl)acrylic acid hydrochloride was dissolved in 100 ml of 1N-sodium hydroxide aqueous solution. To this solution was added 2 g of Raney nickel and hydrogenation was carried out at a room temperature under 3 atmospheric pressure. The catalyst was removed by filtration, the mother liquor was neutralized with acetic acid, and allowed to stand in a refrigerator, the crystals precipitated were collected by filtration. Recrystallized from water to obtain 2 g of 2-amino-3-(8-methoxy-2-quinolon-5-yl)propionic acid hydrochloride hydrate in the form of colorless powdery product.

Melting point: 257°-260° C. (decomp.)

By a method similar to that described in the abovementioned Example 321 using a suitable starting material, there were prepared compounds of Examples 1, 2, 9-19, 21-126.

EXAMPLE 322

2.8 Grams of 2-(4-chlorobenzoyl)amino-3-(2-quinolon-3-yl)propionic acid was dissolved in 50 ml of N,N-dimethylformamide, to this solution was added 1 g of 50%-oily sodium hydride at a room temperature with stirring, then the mixture was further stirred for 30 minutes. Under an ice-cooled condition with stirring, 1.5 g of methyl iodide was added to the mixture, after the reaction was completed, the reaction mixture was concentrated under a reduced pressure, the residue was dissolved in water. This solution was acidified with a concentrated hydrochloric acid, the crystals precipitated were collected by filtration, recrystallized from ethanol to obtawn 0.5 g of 2-(4-chlorobenzoyl)amino-3-(1-methyl-20quinolon-3-yl)propionic acid in the form of white powdery product.

Melting point: 246°-247.5° C. (decomp.)

By a method similar to that described in the above-mentioned Example 322 using a suitable starting material, there were prepared compounds of Examples 10, 14–18, 57–61, 72–76, 98–100, 104, 106–111 and 125.

EXAMPLE 323

To 4 g of 2-amino-3-(6-methoxy-2-quinolon-4-yl)propionic acid hydrochloride was added 50 ml of 48%-hydrobromic acid and the mixture was refluxed for 4 hours. After cooling of the reaction mixture, the crystals precipitated were collected by filtration and were dissolved in an aqueous solution of sodium hydroxide. Then the solution was acidified with hydrochloric acid and the crystals precipitate were collected by filtration. Recrystallized from dimethylformamide-water to obtain 2.2 g of 2-amino-3-(6-hydroxy-2-quinolon-4-yl)propionic acid hydrochloride in the form of white powdery product.

Melting point: Over 300° C.

EXAMPLE 324

2.0 Grams of 2-amino-3-(6-hydroxy-2-quinolon-4-yl)propionic acid hydrochloride and 4.8 g of potassium carbonate were dissolved in 100 ml of aceton with 50 ml of water. To this mixture was added 2.7 g of p-chlorobenzoyl chloride was added dropwise under ice-cooled condition with stirring. The reaction was continued for 3 hours under ice-cooled condition with stirring. Acetone was removed by distillation, the residue obtained was diluted with water, acidified with hydrochloric acid. The crystals precipitated were collected by filtration. Recrystallized from ethanol-water to obtain 1.5 g of 2-(4-chlorobenzoylamino)3-[6-(4-chlorobenzoyloxy)-2-quinolon-4-yl]propionic acid in the form of white powdery product.

Melting point: 302–303 (decomp.)

EXAMPLE 325

1.8 Grams of 2-(4-chlorobenzoylamino)-3-(2-quinolon-4-yl)propionic acid was dissolved in 80 ml of N,N-dimethylformamide. To this solution was added 0.6 g of triethylamine. Then, under ice-cooled condition with stirring, 0.8 g of isobutyl chloroformate was added to the above-mentioned mixture. At the same temperature condition, 10 ml of N,N-dimethylformamide solution containing 0.4 g of ammonia was added dropwise to the reaction mixture, and stirred for 3 hours. After the removal of N,N-dimethylformamide by distillation, water was added to the residue and the crystals precipitated were collected by filtration, and were washed with an aqueous solution of sodium hydroxide. Recrystallized from dimethylformamide-water to obtain 0.7 g of 2-(4-chlorobenzoylamino)-3-(2-quinolon-4-yl)propionamide in the form of light yellowish powdery product.

Melting point: Over 300° C.

By a method similar to that described in Example 325, by using a suitable strating material, there were prepared compounds of Examples 102 and 103.

EXAMPLE 326

1.9 Grams of 2-(4-chlorobenzoylamino)-3-(2-quinolon-4-yl)propionic acid was dissolved in 20 ml of HMPA. To this solution was added dropwise 3 ml of an aqueous solution containing 0.3 g of sodium hydroxide and stirred at a room temperature for 1 hour. The reaction mixture was poured into ice-water, then the crystals precipitated were collected by filtration. Recrystallized from ethanol to obtain 0.5 g of methoxycarbonylmethyl 2-(4-chlorobenzoylamino)-3-(2-quinolon-4-yl)propionate in the form of white granular crystals.

Melting point: 202.5°–204.5° C.

By a method similar to that described in Exampl3 326, by using a suitable starting material, there were prepared compounds of Examples 118 and 119.

EXAMPLE 327

1.8 Grams of 2-amino-3-(2-quinolon-4-yl)propionic acid hydrochloride was dissolved in a solution containing 0.8 g of sodium hydroxide in acetone containing acetone. Under stirring at a room temperature, 1.3 g of p-chlorobenzenesulfonyl chloride was added therto and the whole reaction mixture was stirred at a room temperature for 3 hours. The precipitates were removed by filtration and the filtrate was acidified with hydrochloric acid. The crystals precipitated were collected by filtration, and recrystallized from dimethylformamide-water to obtain 1.6 g of 2-[4-chlorobenzenesulfonylamino-3-(2-quinolon-4-yl)]propionic acid in the form of white powdery product.

Melting point: 299°–300° C. (decomp.).

EXAMPLES 328–333

By a method similar to that described in Example 327, by using a suitable starting material, there were prepared compounds as shown in Table 9 as follows.

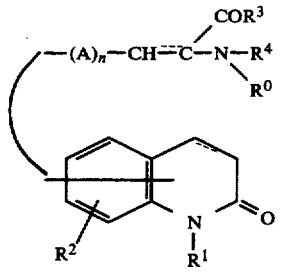

TABLE 9

| Example | $R^1$ | $R^2$ | $R^3$ | $R^4$ | Substituted position of the side-chain $-(A)_n-CH=C(COR^3)-N(R^4)R^o$ | Carbon-carbon bond between 3- and 4- positions | $-CH=C$ |
|---|---|---|---|---|---|---|---|
| 328 | H | H | OH | 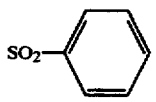 | 4 | Double bond | $CH_2CH$ |

TABLE 9-continued

| | | | | | | | |
|---|---|---|---|---|---|---|---|
| 329 | H | H | OH | 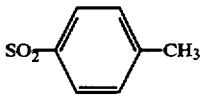 | 4 | Double bond | $CH_2CH$ |
| 330 | $CH_3$ | H | OH | H | 4 | Double bond | $CH_2CH$ |
| 331 | $CH_3$ | H | OH | $CH_3$ | 4 | Double bond | $CH_2CH$ |
| 332 | H | H | OH | 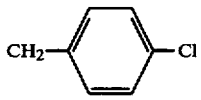 | 4 | Double bond | $CH_2CH$ |
| 333 | H | H | OH | 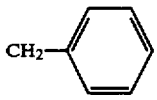 | 4 | Double bond | $CH_2CH$ |

| Example | $(A)_n$ | $R^o$ | Crystal form | Recrystallization solvent | Melting point (°C.) | Type of the salt |
|---|---|---|---|---|---|---|
| 328 | — | H | White powdery product | Dimethyl-formamide-water | 301–302 (decomp.) | — |
| 329 | — | H | White powdery product | Dimethyl-formamide-water | 288–290 (decomp.) | — |
| 330 | — | 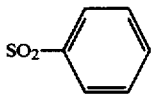 | Colorless prism-like crystals | Ethanol | 236–237.5 (decomp.) | — |
| 331 | — | 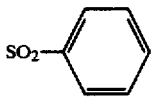 | Colorless prism-like crystals | Ethanol | 251.5–252.5 (decomp.) | — |
| 332 | — | H | White powdery product | Ethanol-water | 275–276 (decomp.) | HCl |
| 333 | — | H | White powdery product | Ethanol-water | 266.5–267.5 (decomp.) | HCl |

EXAMPLE 334

3.0 Grams of 2-amino-3-(1-ethyl-2-oxoquinolin-4-yl)propionic acid hydrochloride and 5.5 g of potassium carbonate were dissolved in 100 ml of acetone and 50 ml of water. To this solution was added 2.2 g of p-chlorobenzoyl chloride dropwise under ice-cooled condition with stirring, and further stirred for 3 hours. Acetone was removed from the reaction mixture by distillation, the residue thus obtained was diluted with water and acidified with hydrochloric acid. The crystals precipitated were recrystallized from ethanol, then the crystals thus obtained were dissolved in 100 ml of methanol containing 1 g of sodium hydroxide and 50 ml of water. The solution was acidified with a concentrated hydrochloric acid and the whole mixture was allowed to stand in a refrigerator. The crystals precipitated were collected by filtration to obtaine 2.4 g of 2-(4-chlorobenzoylamino)-3-(1-ethyl-2-oxoquinolin-4-yl)propionic acid hydrate in the form of white powdery product.

Melting point: 263°–262.5° C.

NMR (Dimethyl sulfoxide) δ. 1.17 (3H, t, J=7 Hz), 3.00–3.70 (2H, m), 4.18 (2H, q, J=7 Hz), 4.50–5.80 (1H, m), 6.53 (1H, s), 7.10–8.00 (8H, m), 8.88 (1H, d, J=7.5 Hz).

EXAMPLE OF FILM COATED TABLES

| | |
|---|---|
| 2-(4-Chlorobenzoylamino)-3-(2-quinolon-3-yl)propionic acid | 150 g |
| Avicel (Trademark for microcrystalline cellulose, manufactured by Asahi Chemical Industries, Ltd.) | 40 g |
| Corn starch | 30 g |
| Magnesium stearate | 2 g |
| Hydroxypropylmethylcellulose | 10 g |
| Polyethylene glycolcellulose | 3 g |
| Castor oil | 40 g |
| Methanol | 40 g |

2-(4-Chlorobenzoylamino)-3-(2-quinolon-3-yl)propionic acid, Avicel, corn starch and magnesium stearate were admixed together and ground, and then compressed into tables with a punch having a diameter of 10 mm. The tables obtained were coated with a film coating agent consisting of hydroxypropylmethylcellulose, polyethylene glycol-6000, castor oil and methanol, to prepare film coated tables.

EXAMPLE OF COATED TABLES

| | |
|---|---|
| 2-(4-Chlorobenzoylamino)-3-(2-quinolon-4-yl)propinoic acid | 150 g |
| Citric acid | 1.0 g |
| Lactose | 33.5 g |
| Dicalcium phosphate | 70.0 g |

-continued

| | |
|---|---|
| Pluronic F-68 | 30.0 g |
| Sodium lauryl sulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dried sodium lauryl sulfate | 3.0 g |
| Dried magnesium stearate | 3.0 g |
| Ethanol | q.s. |

2-(4-Chlorobenzoylamino)-3-(2-quinolon-4-yl)propionic acid, citric acid, lactose, dicalcium phosphate, Pluronic F-68 and sodium lauryl sulfate were admixed together and the obtained mixture was sieved through No. 60 sieve then the sieved mixture was wet granulated with an alcoholic solution containing polyvinylpyrrolidone, Carbowax 1500 and 6000. The granulated product was made in to paste like lump by adding ethanol if necessary. Corn starch was added thereto and the mixture was well mixed until uniform granules were formed. The granules were sieved through No. 1 sieve, and the granules sieved were placed in a tray and dried at 100° C. in an oven for 12–14 hours. The dried granules were sieved through No. 16 sieve, to the sieved granules were added dried sodium lauryl sulfate and dried magnesium stearate, then the whole mixture was mixed well and were compressed into the shape of desired form by using a tablet machine to obtain tablets to be used for the core portions of coated tablets. The core portions were treated with a varnish, and further the treated surface thereof were coated with talc for preventing the surface from the absorption of moisture. The treated surface of core portions were further coated with a primary coating layer, and further coated with a varnish to make a sufficient number of layers for preparing coated tablets for oral administration. In order to make the coated core portions of tablets into complete spherical form and to make the treated surface smoothly, the coated tablets were further coated with primary coating layers and smoothing coating layers. The coated tablets were color coated until the desired color of the surface was obtained. After the coated tablets were dried, the surface therof were polished to make them uniform gloss.

EXAMPLE OF PREPARATION OF INJECTION COMPOSITION

| | |
|---|---|
| 2-(4-Chlorobenzoylamino)-3-(1-methyl-2-quinolon-3-yl)propionic acid | 5.0 g |
| Polyethylene glycol (Molecular weight: (Molecular weight: 4000) | 0.3 g |
| Sodium chloride | 0.9 g |
| Polyoxyethylene sorbitan monooleate | 0.4 g |
| Sodium metabisulfite | 0.1 g |
| Methylparaben | 0.18 g |
| Propylparaben | 0.02 g |
| Distilled water for injection | 100 ml |

Above-mentioned Methylparaben, Propylparaben, sodium metabisulfite and sodium chloride were dissolved in a half amount of the above-mentioned distilled water at 80° C. with stirring. The solution obtained was cooled to 40° C., and the present compound, polyethylene glycol and polyoxyethylene sorbitan monooleate were dissolved, in this order, in the above-mentioned solution. To the solution thus obtained was added the remaining amount of distilled water for injection to make the volume of the injection composition into the predetermined volume, then was sterilized by sterilizing filtration using a suitable filter paper to prepare injection preparation.

PHARMACOLOGICAL TEST (1) Compound to be tested 1. 2-(4-chlorobenzoylamino)-3-(2-quinolon-3-yl)propionic acid
2. 2-Benzoylamino-3-(2-quinolon-3-yl)propionic acid
3. 2-Cyclohexylcarbonylamino-3-(2-quinolon-3-yl)propinoic acid
4. 2-(4-Chlorobenzoylamino)-3-(1-methyl-2-quinolon-3-yl)propionic acid
5. 2-(4-Chlorobenzoylamino)-3-(2-quinolon-4-yl)propionic acid
6. 2-Benzoylamino-3-(2-quinolon-4-yl)propionic acid
7. 2-Benzoylamino-3-(1-methyl-2-quinolon-4-yl)propionic acid
8. 2-(4-Chlorobenzoylamino)-3-(1-propargyl-2-quinolon-4-yl)propionic acid
9. 2-(4-Chlorobenzoylamino)-3-(1-propargyl-2-quinolon-4-yl)propionic acid
10. 2-(4-Chlorobenzoylamino)-3-(1-benzyl-2-quinolon-4-yl)propionic acid
11. 2-(4-Chlorobenzoylamino)-3-(1-n-butyl-2-quinolon-4-yl)propionic acid
12. 2-(4-Chlorobenzoylamino)-3-(8-hydroxy-2-quinolon-5-yl)propionic acid
13. 2-(4-Chlorobenzoylamino)-3-(8-methoxy-2-quinolon-5-yl)propionic acid
14. 2-(4-Chlorobenzoylamino)-3-(8-methyl-2-quinolon-4-yl)propionic acid
15. 4-[2-(4-α-Carboxycyclohexyl-1-β-methylaminocarbonyl)-2-(4-chlorobenzoylamino)ethyl]carbostyril
16. 4-[2-(4-α-Ethoxycarbonylcyclohexyl-1-β-methylaminocarbonyl)-2-(4-chlorobenzoylamino)ethyl]carbostyril
17. 2-(4-α-Aminomethylcyclohexylcarbonylamino)-3-(2-quinolon-4-yl)propionic acid
18. 2-(3-Chlorobenzoylamino)-3-(2-quinolon-4-yl)propionic acid
19. 2-(2-Chlorobenzoylamino)-3-(2-quinolon-4-yl)propionic acid
20. 2-(2,4-Dichlorobenzoylamino)-3-(2-quinolon-4-yl)[pripionic] *propionic* acid
21. 2-(4-Methoxybenzoylamino)-3-(2-quinolon-3-yl)propionic acid
22. 2-(3,4,5-Trimethoxybenzoylamino)-3-(2-quinolon-4-yl)[pripionic] *propionic* acid
23. 2-(2,4-Dimethylbenzoylamino)-3-(2-quinolon-4-yl)[pripionic] *propionic* acid
24. 2-(4-Nitrobenzoylamino)-3-(2-quinolon-4-yl)[pripionic] *propionic* acid
25. 2-(4-Aminobenzoylamino)-3-(2-quinolon-4-yl)[pripionic] *propionic* acid
26. 2-(4-Hydroxybenzoylamino)-3-(2-quinolon-4-yl)propionic acid
27. 2-(4-Chlorobenzylcarbonylamino)-3-(2-quinolon-4-yl)[pripionic] *propionic* acid
28. 2-Benzylcarbonylamino-3-(2-quinolon-4-yl)propionic acid
29. 2-(2-Furoylamino)-3-(2-quinolon-4-yl)propionic acid
30. 2-(3-Pyridylcarbonylamino)-3-(2-quinolon-4-yl)propionic acid
31. 2-(4-Methyl-thioazol-5-ylcarbonylamino)-3-(2-quinolon-4-yl)propionic acid 32. 2-(4-Methylbenzoylamino)-3-(2-quinolon-4-yl)propionic acid
33. 2-(4-Chlorobenzoylamino)-3-(2-quinolon-3-yl)acrylic acid
34. 2-Cyclohexylcarbonylamino-3-(1-ethyl-2-quinolon-4-yl)propionic acid
35. 2-Benzoylamino-3-(1-methyl-2-quinolon-4-yl)propionic acid
36. 2-(4-Chlorobenzenesulfonylamino)-3-(2-quinolon-4-yl)propionic acid
37. 2-(Cyclopropylcarbonylamino)-3-(2-quinolon-4-yl)propionic acid Reference compound:

Sucralfate = sucrose hydrogen sulfate basic aluminum salt (administered in the dosage of 1,000 mg/kg/each administration twice a day, for 9 days).

(2) Method of the test

Under anesthetized with ether, the venter of a rat was incised to take out the stomach. By using a microsyringe, 15 ml of 30%-acetic acid was injected, from the serosa-side, to submucous membrane of the bifurcation of paries anterior ventriculi and vestibule of pylorus. The injected portion of the bifurcation was kept pressing for a few seconds to prevent the leakage of the injected fluid. The incised protion of the venter was sutured, and the rat was fasted for overnight, then a test compound was orally administered in the amount of 10 mg/kg/each administration, twice a day i.e., in the morning and evening, for 9 days. After 4 hours of the final administration, the rat was killed by dislocation of the collum, then the stomach was enucleated from the rat, and was fixated by injecting 10 ml of 1%-formalin solution. The stomach was cut out along the great flexura line and the ulceration area of the stomach (hereinafter referred to as the ulceration index) was measured by using an orthoscopic microscope (magnification: ×10), and the curative ratio of the test compound was calculated from the formula as follows:

$$\left(\begin{array}{c}\text{Curative}\\ \text{ratio}\end{array}\right) = \frac{\left(\begin{array}{c}\text{Ulceration index}\\ \text{of the reference}\\ \text{group}\end{array}\right) - \left(\begin{array}{c}\text{Ulceration index}\\ \text{of the test}\\ \text{compound group}\end{array}\right)}{\left(\begin{array}{c}\text{Ulceration index}\\ \text{of the reference}\\ \text{group}\end{array}\right)}$$

(A rat of the reference group was administered with water or 0.5%-carboxymethylcellulose aqueous solution.)

The results of the test are shown in the following Table.

TABLE

| Test compound No. | Curative ratio (%) |
|---|---|
| 1 | 38.5 |
| 2 | 28.0 |
| 3 | 25.0 |
| 4 | 38.4 |
| 5 | 38.5 |
| 6 | 28.1 |
| 7 | 33.0 |
| 8 | 16.8 |
| 9 | 27.6 |
| 10 | 13.7 |
| 11 | 22.3 |
| 12 | 17.7 |
| 13 | 18.2 |
| 14 | 28.3 |
| 15 | 16.5 |

TABLE-continued

| Test compound No. | Curative ratio (%) |
|---|---|
| 16 | 13.4 |
| 17 | 22.1 |
| 18 | 25.3 |
| 19 | 12.4 |
| 20 | 22.3 |
| 21 | 28.5 |
| 22 | 13.5 |
| 23 | 15.0 |
| 24 | 21.3 |
| 25 | 24.8 |
| 26 | 21.0 |
| 27 | 25.2 |
| 28 | 17.8 |
| 29 | 23.2 |
| 30 | 17.6 |
| 31 | 20.0 |
| 32 | 22.3 |
| 33 | 18.7 |
| 34 | 23.6 |
| 35 | 19.6 |
| 36 | 18.1 |
| 37 | 28.9 |
| Reference compound: | |
| Sucralfate | 29.0 |

What is claimed is:

1. (a) A carbostyril derivative or *a pharmaceutically acceptable* salt thereof represented by the formula

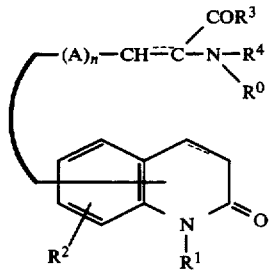

wherein:

$R^1$ is a hydrogen atom, a lower alkyl group, a lower alkenyl group, a lower alkynyl group or a phenyl-lower alkyl group;

$R^2$ is a hydrogen atom, [a halogen atom, a benzoyloxy group, said benzoyloxy group having a halogen atom substituent,] a hydroxyl group, a lower alkyl group or a lower alkoxy group;

$R^3$ is a hydroxyl group, an amino group, said amino group having a cycloalkyl-lower alkyl group substituent, *or* said amino group having a cycloalkyl-lower alkyl group substituent having a carboxy group or a lower alkoxycarbonyl group substituent on the cycloalkyl ring[a lower alkoxy group, a lower alkoxycarbonyl-lower alkoxy group, a benzoyl-lower alkoxy group or a lower alkanoyloxy-lower alkoxy group];

$R^4$ is [a hydrogen atom,] a phenylsulfonyl group, said phenylsulfonyl group having lower alkyl group or halogen atom substituents, [a lower alkyl group, a phenyl-lower alkyl group, said phenyl-lower alkyl group having halogen atom substituents on the phenyl ring,] or a group of the formula —$COR^5$ wherein $R^5$ is [a lower alkyl group, said lower alkyl group having amino group or phenyl-lower alkoxycarbonylamino group substituents,] a cycloalkyl group, said cycloalkyl group having an amino-lower alkyl group or a phenyl-lower alkoxycarbonylamino-lower alkyl group substituent on the cycloalkyl ring, a phenyl group, said phenyl group having 1 to 3 halogen atom, lower alkyl group, lower alkoxy group, nitro group, amino group or hydroxyl group substituents on the phenyl ring, or a 5- or 6-membered unsaturated heterocyclic ring selected from the group consisting of pyridyl, 2-methylpyridyl, 3-ethylpyridyl, 4-butylpyridyl, [thienyl, 2-methylthienyl, 3-propylthienyl, pyrimidyl, 2-pentylpyrimidinyl, pyrrolyl, 3-methyl-pyrrolyl, 1-pyrazinyl, 4-pentyl-1-pyraxinyl, pyrazoylyl, 3-methylpyrazolyl, 4-ethylpyrazolyl, imidazolyl, 2-propylimidazolyl, 4-pentylimidazolyl, pyridazinyl, 4-methylpyridazinyl, pyrazinyl, 2-ethylpyrazinyl, oxazolyl, 4-butyloxazolyl, isoxazolyl, 4H-1,4-oxazinyl,] thiazolyl, 4-methylthiazolyl, 2-ethylthiazolyl, 5-propylthiazolyl, isothiazolyl, 3-methylisothiazolyl, furyl, 3-methylfuryl, *and* 2-ethylfuryl[, 2-methylthianyl, 4-methylthianyl and 4-methylthianyl] groups;

$R^0$ is a hydrogen atom[, a phenylsulfonyl group or said phenylsulfonyl group having lower alkyl group or halogen atom substituents];

A is a lower alkylene group;

n is 0 or 1;

the carbon-carbon bond of —CH---C< is a single or double carbon-carbon *bond, wherein the dashed bond becomes two hydrogen atoms when the carbon-carbon bond is a single* bond;

the carbon-carbon bond between the 3- and 4-positions in the carbostyril skeleton is a single or double bond; and the substitution position of the side-chain of the formula

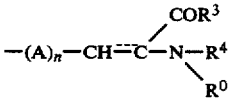

is any one of the 3-, 4-, 5-, 6-[7-] or 8-positions in the carbostyril skeleton[;

(b) a carbostyril derivative represented by the formula

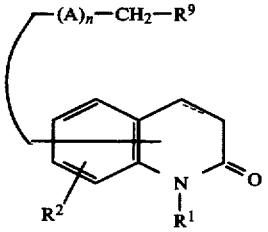

wherein:

$R^1$ is a hydrogen atom, a lower alkyl group, a lower alkenyl group, a lower alkynyl group or phenyl-lower alkyl group;

$R^2$ is a hydrogen atom, a hydroxyl group, a lower alkyl group, a lower alkoxy group, a halogen atom, a benzoyloxy group or said benzoyloxy group having halogen atom substituents;

$R^9$ is a group of the formula

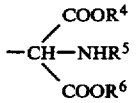

wherein $R^4$ and $R^6$ are lower alkyl groups and $R^5$ is a lower alkanoyl group;

A is a lower alkylene group;

n is 0 or 1;

the carbon-carbon bond between the 3- and 4- positions in the carbostyril skeleton is a single or double bond; and the substitution position of the side-chain of the formula $—(A)_n—CH_2—R^9$ is any one of the 3-, 4-, 5-, 6-, 7-, or 8-positions in the carbostyril skeleton;

provided that when $R^2$ is a hydrogen atom and n is 1, and $R^9$ is a halogen atom, then the substitution position of the side chain of the formula $—(A)_n—CH_2—R^9$ is the 3- or 4-position in the carbostyril skeleton].

[2. A carbostyril derivative represented by the formula

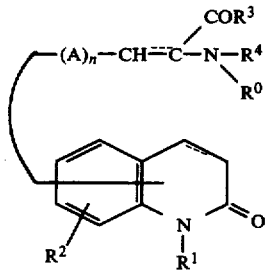

wherein $R^0$, $R^1$, $R^2$, $R^3$, $R^4$, A, n, the carbon-carbon bond in the side-chain, the carbon-carbon bond between the 3- and 4-positions in the carbostyril skeleton and the substitution position of the side-chain are the same as defined in claim 1(a).]

[3. A carbostyril derivative represented by the formula

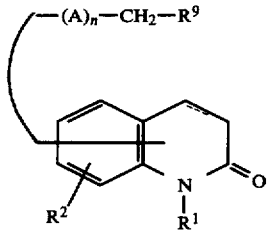

wherein $R^1$, $R^2$, $R^9$, A, n, the carbon-carbon bond in the side-chain, the carbon-carbon bond between the 3- 4-positions in the carbostyril skeleton, and the substituted position of the side-chain are the same as defined in claim 1(b).]

4. The carbostyril derivative according to claim [2] *1*, wherein n is 0.

5. The carbostyril derivative according to claim [2] *1*, wherein n is 1.

[6. The carbostyril derivative according to claim 4, wherein $R^o$ is a hydrogen atom.]

[7. The carbostyril derivative according to claim 4, wherein $R^0$ is a phenylsulfonyl group or said phenylsulfonyl group having lower alkyl group or halogen atom substituents.]

8. The carbostyril derivative according to claim [6] *1*, wherein $R^3$ is a hydroxyl group.

[9. The carbostyril derivative according to claim 6, wherein $R^3$ is a lower alkoxy group, a lower alkoxycarbonyl-lower alkoxy group, a benzoyl-lower alkoxy group or a lower alkanoloxy-lower alkoxy group.]

10. The carbostyril derivative according to claim [6] *1*, wherein $R^3$ is an amino group.

[11. The carbostyril derivative according to claim 8, 9 or 10, wherein $R^4$ is a hydrogen atom.]

12. The carbostyril derivative according to claim 8[, 9] or 10, wherein $R^4$ is [a lower alkyl group, a phenyl-lower alkyl group, said phenyl-lower alkyl group having halogen atom substituents on the phenyl ring,] a phenylsulfonyl group or said phenylsulfonyl group having lower alkyl group or halogen atom substituents.

13. The carbostyril derivative according to claim 8, wherein $R^4$ is a group of the formula —$COR^5$.

[14. The carbostyril derivative according to claim 9, wherein $R^4$ is a group of the formula —$COR^5$.]

15. The carbostyril derivative according to claim 10, wherein $R^4$ is a group of the formula —$COR^5$.

16. The carbostyril derivative according to claim 13 [or 14], wherein $R^5$ is a phenyl group or said phenyl group having 1 to 3 halogen atom, lower alkyl group, lower alkoxy group, nitro group, amino group or hydroxyl group substituents on the phenyl ring.

17. The carbostyril derivative according to claim 16, wherein $R^5$ is a phenyl group having 1 to 3 halogen atom substituents on the phenyl ring.

18. The carbostyril derivative according to claim 13 [or 14], wherein $R^5$ is a cycloalkyl group or said cycloalkyl group having an amino-lower alkyl group or a phenyl-lower alkoxycarbonylamino-lower alkyl group substituent on the cycloalkyl ring.

[19. The carbostyril derivative according to claim 13 or 14, wherein $R^5$ is a lower alkyl group or said lower alkyl group having an amino group or a phenyl-lower alkoxycarbonylamino group substituent.]

20. The carbostyril derivative according to claim 16, wherein $R^2$ is a hydrogen atom.

21. The carbostyril derivative according to claim 16, wherein $R^2$ is a hydroxyl group[, a lower alkyl group, a benzoyloxy group, said benzoyloxy group having halogen atom substituents, a halogen atom] or a lower alkoxy group.

22. The carbostyril derivative according to claim 20, wherein $R^1$ is a hydrogen atom or a lower alkyl group.

23. The carbostyril derivative according to claim 20, wherein $R^1$ is a lower alkenyl group, a lower alkynyl group or a phenyl-lower alkyl group.

24. The carbostyril derivative according to claim 21, wherein the substituted position of the side-chain of the formula

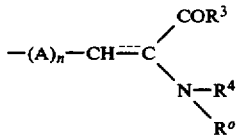

is the 3- or 4-position in the carbostyril skeleton.

25. The carbostyril derivative according to claim 22, wherein the substituted position of the side-chain of the formula

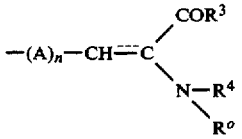

is the 3- or 4-position in the carbostyril skeleton.

26. The carbostyril derivative according to claim 22, wherein the substituted position of the side-chain of the formula

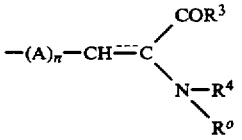

is the 5-, 6-[, 7-] or 8-position in the carbostyril skeleton.

27. The carbostyril derivative according to claim 23, wherein the substituted position of the side-chain of the formula

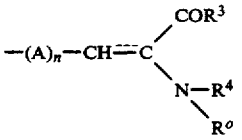

is the 3- or 4-position in the carbostyril skeleton.

28. The carbostyril derivative according to claim 24, wherein the carbon-carbon bond of —CH=C< in the side-chain of the formula

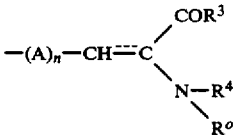

is a single bond.

29. The carbostyril derivative according to claim 25, wherein the carbon-carbon bond of —CH=C< in the side-chain of the formula

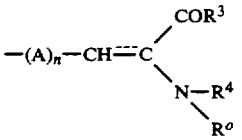

is a single bond.

30. The carbostyril derivative according to claim 27, wherein the carbon-carbon bond of —CH=C< in the side-chain of the formula

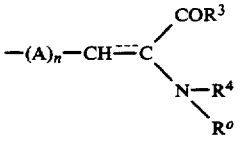

is a single bond.

31. The carbostyril derivative according to claim 25, wherein the carbon-carbon bond of —CH=C< in the side-chain of the formula

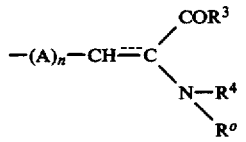

is a double bond.

32. The carbostyril derivative according to claim 29, wherein the carbon-carbon bond between the 3- and 4-positions in the carbostyril skeleton is a double bond.

33. The carbostyril derivative according to claim 30, wherein the carbon-carbon bond between the 3- and 4-positions in the carbostyril skeleton is a double bond.

34. The carbostyril derivative according to claim 29, wherein the carbon-carbon bond between the 3- and 4-positions in the carbostyril skeleton is a single bond.

35. The carbostyril derivative according to claim 30, wherein the carbon-carbon bond between the 3- and 4-positions in the carbostyril skeleton is a single bond.

36. The carbostyril derivative according to claim 17, wherein $R^2$ is a hydrogen atom, $R^1$ is a hydrogen atom or a lower alkyl group, and the substituted position of the side-chain of the formula

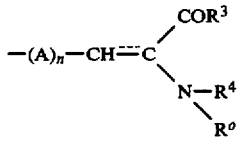

is the 3- or 4-position in the carbostyril skeleton.

37. The carbostyril derivative according to claim 35, wherein the carbon-carbon bond of —CH=C< in the side-chain of the formula

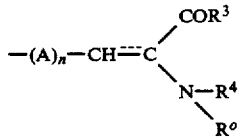

is a single bond, and the carbon-carbon bond between the 3- and 4-positions in the carbostyril skeleton is a double bond.

38. The carbostyril derivative according to claim 35, wherein the carbon-carbon bond of —CH=C< in the side-chain of the formula

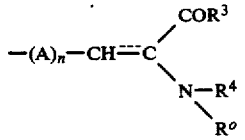

is a single bond, and the carbon-carbon bond between the 3- and 4-positions in the carbostyril skeleton is also a single bond.

39. 2-(4-Chlorobenzolyamino)-3-(2-quinolon-4-yl)propionic acid.

40. 2-(4-Chlorobenzolyamino)-3-(1-methyl-2-quinolon-3-yl)propionic acid.

41. 2-(4-Chlorobenzoylamino)-3-(1-ethyl-2-quinolon-4-yl)propionic acid.

42. 2-Benzolyamino-3-(1-ethyl-2-quinolon-4-yl)propionic acid.

43. A pharmaceutical composition for use in an anti-peptic ulcer agent, which contains the carbostyril derivative as claimed in claim 1(a) as the active ingredient.

44. The carbostyril derivative according to claim 17 or 36, wherein $R^5$ is a phenyl group having a halogen atom as the substituent on the phenyl ring.

45. The carbostyril derivative according to claim 44, wherein the substituted position of the halogen atom is the 2-position in the phenyl ring.

46. The carbostyril derivative according to claim 44, wherein the substituted position of the halogen atom is the 3-position in the phenyl ring.

47. The carbostyril derivative according to claim 44, wherein the substituted position of the halogen atom is the 4-position in the phenyl ring.

* * * * *